United States Patent
Wang et al.

(10) Patent No.: US 11,289,663 B2
(45) Date of Patent: Mar. 29, 2022

(54) ORGANIC SEMICONDUCTING COMPOUNDS

(71) Applicant: Raynergy Tek Incorporation, Hsinchu (TW)

(72) Inventors: Changsheng Wang, Chandler's Ford (GB); William Mitchell, Chandler's Ford (GB)

(73) Assignee: RAYNERGY TEK INCORPORATION, Hsinchu (TW)

( * ) Notice: Subject to any disclaimer, the term of this patent is extended or adjusted under 35 U.S.C. 154(b) by 255 days.

(21) Appl. No.: 16/492,377

(22) PCT Filed: Mar. 6, 2018

(86) PCT No.: PCT/EP2018/055406
§ 371 (c)(1),
(2) Date: Sep. 9, 2019

(87) PCT Pub. No.: WO2018/162447
PCT Pub. Date: Sep. 13, 2018

(65) Prior Publication Data
US 2020/0373502 A1    Nov. 26, 2020

(30) Foreign Application Priority Data

Mar. 9, 2017 (EP) .................... 17160116

(51) Int. Cl.
| | |
|---|---|
| *C07D 209/52* | (2006.01) |
| *H01L 51/00* | (2006.01) |
| *C07D 495/04* | (2006.01) |
| *H01L 51/05* | (2006.01) |
| *H01L 51/42* | (2006.01) |
| *H01L 51/50* | (2006.01) |

(52) U.S. Cl.
CPC ........ *H01L 51/0074* (2013.01); *C07D 495/04* (2013.01); *H01L 51/0566* (2013.01); *H01L 51/4253* (2013.01); *H01L 51/5056* (2013.01); *H01L 51/5072* (2013.01); *H01L 51/5088* (2013.01); *H01L 51/5092* (2013.01)

(58) Field of Classification Search
CPC ............. H01L 51/0074; H01L 51/0566; H01L 51/4253; H01L 51/5056; H01L 51/5072; H01L 51/5088; H01L 51/5092; C07D 495/04; C07D 215/00; C07D 215/38; C07D 215/44; C07D 215/46; C07D 209/52; C07D 217/00
See application file for complete search history.

(56) References Cited

U.S. PATENT DOCUMENTS

| | | |
|---|---|---|
| 8,859,445 B2 | 10/2014 | Cabodi et al. |
| 2015/0255725 A1 | 9/2015 | Mitchell et al. |
| 2015/0303383 A1 | 10/2015 | Takimiya et al. |
| 2017/0062726 A1 | 3/2017 | Choi et al. |

FOREIGN PATENT DOCUMENTS

| | | |
|---|---|---|
| CN | 102260191 A | 11/2011 |
| CN | 102477045 A | 5/2012 |
| CN | 104557968 A | 4/2015 |
| CN | 104769076 A | 7/2015 |
| CN | 104903330 A | 9/2015 |
| CN | 104557968 B | 4/2017 |
| CN | 105838104 B | 11/2017 |
| CN | 105837598 B | 7/2018 |
| EP | 2530085 B1 | 3/2015 |
| JP | 2012-193145 | 10/2012 |
| TW | 201529580 A | 8/2015 |
| WO | WO2011091609 A1 | 8/2011 |
| WO | 14053206 A1 | 4/2014 |

OTHER PUBLICATIONS

Air- and Heat-Stable Planar Tri-p-quinodimethane with Distinct Biradical Characteristics, Zhu et al., J. Am. Chem. Soc. 2011, 133, 16342-16345.*
Planarization, Fusion, and Strain of Carbon-Bridged Phenylenevinylene Oligomers Enhance π-Electron and Charge Conjugation: A Dissectional Vibrational Raman Study, Burrezo et al., J. Am. Chem. Soc. 2015, 137, 3834-3843.*
WO18162447 (PCT/EP2018/055406) International Search report dated Apr. 26, 2018 (pp. 1-127).
TW OA issued on Sep. 22, 2021.
Paula Mayorga Burrezo et al., "Planarization, Fusion, and Strain of Carbon-Bridged Phenylenevinylene Oligomers Enhance π-Electron and Charge Conjugation A Dissectional Vibrational Raman Study", Published: Mar. 2, 2015, 2015, pp. 3834-3843, American Chemical Society.
China Patent Office "Office Action" issued on Dec. 2, 2021, China.
Japan Patent Office "Office Action" issued on Jan. 11, 2022, Japan.

* cited by examiner

*Primary Examiner* — Haidung D Nguyen
(74) *Attorney, Agent, or Firm* — WPAT, PC

(57) ABSTRACT

The invention relates to novel organic semiconducting compounds containing a π-extended ω-disubstituted dicyanomethylene quinoid structure, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, perovskite-based solar cell (PSC) devices, organic photodetectors (OPD), organic field effect transistors (OFET) and organic light emitting diodes (OLED), and to OE, OPV, PSC, OPD, OFET and OLED devices comprising these compounds, compositions or polymer blends.

16 Claims, No Drawings

ORGANIC SEMICONDUCTING COMPOUNDS

TECHNICAL FIELD

The invention relates to novel organic semiconducting compounds containing a π-extended ω-disubstituted dicyanomethylene quinoid structure, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, perovskite-based solar cell (PSC) devices, organic photodetectors (OPD), organic field effect transistors (OFET) and organic light emitting diodes (OLED), and to OE, OPV, PSC, OPD, OFET and OLED devices comprising these compounds, compositions or polymer blends.

BACKGROUND

In recent years, there has been development of organic semiconducting (OSC) materials in order to produce more versatile, lower cost organic electronic (OE) devices. Such materials find application in a wide range of devices or apparatus, including organic field effect transistors (OFETs), organic light emitting diodes (OLEDs), perovskite-based solar cell (PSC) devices, organic photodetectors (OPDs), organic photovoltaic (OPV) cells, sensors, memory elements and logic circuits to name just a few. The organic semiconducting materials are typically present in the electronic device in the form of a thin layer, for example of between 50 and 300 nm thickness.

OSC materials have been attracting remarkable attention for the last two decades mostly due to their lucrative commercial prospects in OE devices manufactured by cost effective solution processing technology at low temperature. It is generally believed that organic and/or polymeric semiconductors have a number of advantages over their inorganic counterparts, such as the potential of fabricating lightweight flexible backplanes, the opportunity to make large area displays using low-cost, high speed solution based fabrication techniques, and their optical and electronic properties being fine-tuneable via rational chemical structure modifications. The main disadvantage is, however, that they still exhibit relatively low device performances and modest thermal, photo and electrical stabilities. Thanks to the intensive structural design and synthetic studies over the past two decades or so, a wide range of novel π-conjugated polymers were made available and their performances in OSC based devices, notably, in thin film transistors (TFTs) have witnessed great improvement, surpassing that of amorphous silicon, in terms of charge carrier mobilities. In the meantime, power conversion efficiencies of organic solar cells fabricated using low bandgap π-conjugated polymers as active electron donor materials have exceeded 10%.

To date, a large number of π-conjugated compounds have been synthesized which can be used as OSC materials in OE devices like OFETs, OPV cells or OPDs. Among these, p-type OSC materials remain overwhelmingly dominant mainly due to the relative ease of synthetic accessibility of building blocks and precursors. In contrast, there have been only a paucity of electron accepting conjugated compounds available, which have shown commercial potential as n-type OSCs. This situation leads to limited choice of complimentary n-type OSCs in manufacturing organic circuits containing CMOS structures.

There is still a need for n-type OSCs for use in OE devices like OPV cells, OPDs and OFETs, which have advantageous properties, in particular good processibility, high solubility in organic solvents, good structural organization and film-forming properties. In addition, the OSC materials should be easy to synthesize, especially by methods suitable for mass production. For use in OPV cells, the OSC materials should especially have a low bandgap, which enables improved light harvesting by the photoactive layer and can lead to higher cell efficiencies, high stability and long lifetime. For use in OFETs the OSC materials should especially have high charge-carrier mobility, high on/off ratio in transistor devices, high oxidative stability and long lifetime.

It was an aim of the present invention to provide new n-type OSCs, which can overcome the drawbacks of the OSCs from prior art, and which provide one or more of the above-mentioned advantageous properties, especially easy synthesis by methods suitable for mass production, good processibility, high stability, long lifetime in OE devices, good solubility in organic solvents, high charge carrier mobility, and a low bandgap. Another aim of the invention was to extend the pool of OSC materials and n-type OSCs available to the expert. Other aims of the present invention are immediately evident to the expert from the following detailed description.

The inventors of the present invention have found that one or more of the above aims can be achieved by providing electron deficient compounds as disclosed and claimed hereinafter, which can be used as n-type OSCs. These compounds contain a π-extended quinoid polycyclic unit that is ω-disubstituted by dicyanomethylene groups, as shown in formula I below.

It has been found that such compounds can be used as n-type organic semiconductors for use in OE devices like OPV cells or OPDs, where they show advantageous properties as described above.

Compounds having a quinoidal structure and being terminated by dicyanomethylene groups have been disclosed in prior art documents, for example in CN102477045A, US2015/0303383 A1, CN105837598A and CN105838104A. However, compounds as disclosed and claimed hereinafter have hitherto not been disclosed in prior art.

SUMMARY

The invention relates to a compound of formula I

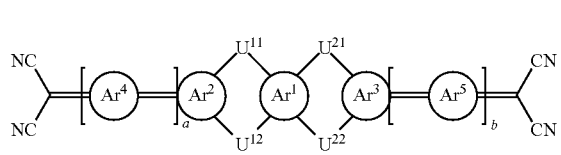

wherein the individual radicals, independently of each other and on each occurrence identically or differently, have the following meanings
one of $U^{11}$ and $U^{12}$ is a C=C double bond and the other is $CR^1R^2$,
one of $U^{21}$ and $U^{22}$ is a C=C double bond and the other is $CR^3R^4$, Ar$^{1-5}$ a quinoidal alicyclic or heterocyclic group, which is optionally part of a larger quinoidal group, has 5 to 30 ring atoms, is mono- or polycyclic, optionally contains fused rings, and is unsubstituted or substituted by one or more identical or different groups R$^1$ or L, R$^{1-4}$ H, F, Cl, CN, straight-chain, branched or cyclic alkyl with 1 to 40 C atoms in which one or more CH$_2$ groups are optionally replaced by —O—, —S—, —C(=O)—, —C(=S)—, —C(=O)—O—, —O—C(=O)—, —NR$^0$—, —SiR$^0$R$^{00}$—, —CF$_2$—, —CR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, and in which one or more CH$_2$ or CH$_3$ groups are optionally replaced by a cationic or anionic group, or straight-chain, branched or cyclic silyl with 1 to 40 Si atoms, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, L F, Cl, —NO$_2$, —CN, —NC, —NCO, —NCS, —OCN, —SCN, R$^0$, OR$^0$, SR$^0$, —C(=O)X$^0$, —C(=O)R$^0$, —C(=O)—OR$^0$, —O—C(=O)—R$^0$, —NH$_2$, —NHR$^0$, —NR$^0$R$^{00}$, —C(=O)NHR$^0$, —C(=O)NR$^0$R$^{00}$, —SO$_3$R$^0$, —SO$_2$R$^0$, —OH, —NO$_2$, —CF$_3$, —SF$_5$, or optionally substituted silyl with 1 to 20 Si atoms, or carbyl or hydrocarbyl with 1 to 30, preferably 1 to 20 C atoms that is optionally substituted and optionally comprises one or more hetero atoms, preferably F, —CN, R$^0$, —OR$^0$, —SR$^0$, —C(=O)—R$^0$, —C(=O)—OR$^0$, —O—C(=O)—R$^0$, —O—C(=O)—OR$^0$, —C(=O)—NHR$^0$, or —C(=O)—NR$^0$R$^{00}$, R$^0$, R$^{00}$ H or straight-chain or branched alkyl with 1 to 20, preferably 1 to 16, C atoms that is optionally fluorinated, X$^0$ halogen, preferably F or Cl, a, b 0 or an integer from 1 to 10, preferably 0, 1, 2 or 3.

The invention further relates to novel synthesis methods for preparing compounds of formula I, and novel intermediates used therein.

The invention further relates to the use of compounds of formula I as semiconductor, preferably as electron acceptor or n-type semiconductor, preferably in a semiconducting material, an electronic or optoelectronic device, or a component of an electronic or optoelectronic device.

The invention further relates to the use of compounds of formula I as dyes or pigments.

The invention further relates to a composition comprising one or more compounds of formula I, and further comprising one or more compounds having one or more of a semiconducting, hole or electron transport, hole or electron blocking, insulating, binding, electrically conducting, photoconducting, photoactive or light emitting property.

The invention further relates to a composition comprising one or more compounds of formula I, and further comprising a binder, preferably an electrically inert binder, very preferably an electrically inert polymeric binder.

The invention further relates to a composition comprising a compound of formula I, and further comprising one or more electron donors or p-type semiconductors, preferably selected from conjugated polymers.

The invention further relates to a composition comprising one or more n-type semiconductors, at least one of which is a compound of formula I, and further comprising one or more p-type semiconductors.

The invention further relates to a composition comprising one or more n-type semiconductors, at least one of which is a compound of formula I, and at least one other of which is a fullerene or fullerene derivative, and further comprising one or more p-type semiconductors, preferably selected from conjugated polymers.

The invention further relates to a bulk heterojunction (BHJ) formed from a composition comprising a compound of formula I as electron acceptor or n-type semiconductor, and one or more compounds which are electron donor or p-type semiconductors, and are preferably selected from conjugated polymers.

The invention further relates to the use of a compound of formula I or a composition as described above and below, as semiconducting, charge transporting, electrically conducting, photoconducting, photoactive or light emitting material.

The invention further relates to the use of a compound of formula I or a composition as described above and below, in an electronic or optoelectronic device, or in a component of such a device or in an assembly comprising such a device.

The invention further relates to a semiconducting, charge transporting, electrically conducting, photoconducting, photoactive or light emitting material, comprising a compound of formula I or a composition as described above and below.

The invention further relates to an electronic or optoelectronic device, or a component thereof, or an assembly comprising it, which comprises a compound of formula I or a composition as described above and below.

The invention further relates to an electronic or optoelectronic device, or a component thereof, or an assembly comprising it, which comprises a semiconducting, charge transporting, electrically conducting, photoconducting or light emitting material as described above and below.

The invention further relates to a formulation comprising one or more compounds of formula I, or comprising a composition or semiconducting material as described above and below, and further comprising one or more solvents, preferably selected from organic solvents.

The invention further relates to the use of a formulation as described above and below for the preparation of an electronic or optoelectronic device or a component thereof.

The invention further relates to an electronic or optoelectronic device or a component thereof, which is obtained through the use of a formulation as described above and below.

The electronic or optoelectronic device includes, without limitation, organic field effect transistors (OFET), organic thin film transistors (OTFT), organic light emitting diodes (OLED), organic light emitting transistors (OLET), organic light emitting electrochemical cell (OLEC), organic photovoltaic devices (OPV), organic photodetectors (OPD), organic solar cells, dye-sensitized solar cells (DSSC), organic photoelectrochemical cells (OPEC), perovskite-based solar cell (PSC) devices, laser diodes, Schottky diodes, photoconductors, photodetectors and thermoelectric devices.

Preferred devices are OFETs, OTFTs, OPVs, PSCs, OPDs and OLEDs, in particular OPDs and BHJ OPVs or inverted BHJ OPVs.

The component of the electronic or optoelectronic device includes, without limitation, charge injection layers, charge transport layers, interlayers, planarising layers, antistatic films, polymer electrolyte membranes (PEM), conducting substrates and conducting patterns.

The assembly comprising an electronic or optoelectronic device includes, without limitation, integrated circuits (IC), radio frequency identification (RFID) tags, security markings, security devices, flat panel displays, backlights of flat panel displays, electrophotographic devices, electrophotographic recording devices, organic memory devices, sensor devices, biosensors and biochips.

In addition the compounds of formula I and compositions as described above and below can be used as electrode materials in batteries, or in components or devices for detecting and discriminating DNA sequences.

Terms and Definitions

As is known to the skilled person a quinone represents a "compound having a fully conjugated cyclic dione structure derived from aromatic or hetero-aromatic compounds by conversion of an even number of —CH= groups into —C(=O)-groups with any necessary rearrangement of double bonds (polycyclic and heterocyclic analogues are included)" (PAC, 1995, 67, 1307). The simplest example is p-benzoquinone.

In prior art the term "quinoidal" is usually understood to mean a compound that is similar to a quinone or in the form of a quinone but excluding the ketone oxygen atoms.

As used herein the terms "quinoid" and "quinoidal" will be understood to mean an unsaturated alicyclic or heterocyclic moiety, or a compound containing such a moiety, which is mono- or polycyclic, fully conjugated, may also be fused with aromatic rings, and contains an even number of two or more $sp^2$ carbon atoms, each of which is chemically connected through an exocyclic C=C double bond to a neighbouring moiety, as shown in formula I, such that the alicyclic or heterocyclic moiety and said neighbouring moieties form an extended $\pi$-conjugated system with a continuous, alternating sequence of C=C double bonds and C—C single bonds.

As used herein, the term "polymer" will be understood to mean a molecule having high relative molecular mass, the structure of which essentially comprises multiple repetitions of units derived, actually or conceptually, from molecules of low relative molecular mass (*Pure Appl. Chem.,* 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.,* 1996, 68, 2291). In a preferred meaning as used herein present invention a polymer will be understood to mean a compound having >1, i.e. at least 2 repeat units, preferably ≥5, very preferably ≥10, repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer", "random polymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a chemical formula depicting for example a substituent, a repeat unit or a polymer, the symbol -* will be understood to mean a single bond to an adjacent group, repeat unit or terminal group. In a ring, like for example a benzene or thiophene ring, an asterisk * will be understood to mean an $sp^2$ carbon atom that forms part of the ring and is bonded to an adjacent group via a single bond.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.,* 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of $R^{22}$ or $R^{23}$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19, Aug. 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with $sp^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, chlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, thioalkyl, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups L, wherein L is selected from F, Cl, —CN, —NC, —NCO, —NCS, —OCN, —SCN, —R°, —OR°, —SR°, —C(=O)X°, —C(=O)R°, —C(=O)—OR°, —O—C(=O)—R°, —NH$_2$, —NHR°, —NR°R$^{00}$, —C(=O)NHR°, —C(=O)NR°R$^{00}$, —SO$_3$R°, —SO$_2$R°, —OH, —NO$_2$, —CF$_3$, —SF$_5$, or optionally substituted silyl, or carbyl or hydrocarbyl with 1 to 40, preferably 1 to 20 C atoms that is optionally substituted and optionally comprises one or more hetero atoms, wherein X° is halogen, preferably F or Cl, and R°, R$^{00}$ denote H or straight-chain or branched alkyl with 1 to 20, preferably 1 to 12 C atoms that is optionally fluorinated.

Preferably L is selected from F, —CN, R°, —OR°, —SR°, —C(=O)—R°, —C(=O)—OR°, —O—C(=O)—R°, —O—C(=O)—OR°, —C(=O)—NHR° and —C(=O)—NR°R$^{00}$.

Further preferably L is selected from F or alkyl, alkoxy, oxaalkyl, thioalkyl, fluoroalkyl, fluoroalkoxy, alkylcarbonyl, alkoxycarbonyl, with 1 to 12 C atoms, or alkenyl or alkynyl with 2 to 12 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3, 4, 5, 6, 7 or 8 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3, 4, 5, 6, 7 or 8 fused or unfused rings, and is optionally substituted with one or more groups L as defined above.

An arylalkyl or heteroarylalkyl group as referred to above and below preferably denotes —$(CH_2)_a$-aryl or —$(CH_2)_a$-heteroaryl, wherein a is an integer from 1 to 6, preferably 1, and "aryl" and "heteroaryl" have the meanings given above and below. A preferred arylalkyl group is benzyl which is optionally substituted by L.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred aryl and heteroaryl groups are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, 2,5-dithiophene-2',5'-diyl, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b]dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl group or an alkoxy group, i.e., where the terminal $CH_2$ group is replaced by —O—, can be straight-chain or branched. It is preferably straight-chain, has 2, 3, 4, 5, 6, 7, 8, 12 or 16 carbon atoms and accordingly is preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one $CH_2$ group is replaced by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly, it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group can either be perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, preferably with 1 to 15 C atoms, in particular 1,1-difluoroalkyl, all of the aforementioned being straight-chain or branched.

Preferably "fluoroalkyl" means a partially fluorinated (i.e. not perfluorinated) alkyl group.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methyl pentyl, 3-methyl pentyl, 2-ethylhexyl, 2-butyloctyl, 2-hexyldecyl, 2-octyldodecyl, 2-propylpentyl, in particular 2-methylbutyl, 2-methylbutoxy, 2-methylpentoxy, 3-methylpentoxy, 2-ethyl-hexoxy, 2-butyloctoxyo, 2-hexyldecoxy, 2-octyldodecoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxy-octoxy, 6-methyloctoxy, 6-methyloctanoyloxy, 5-methyl heptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-ethylhexyl, 2-butyloctyl, 2-hexyldecyl, 2-octyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy, 3-methylbutoxy and 3,7-dimethyloctyl.

In a preferred embodiment, the substituents on an aryl or heteroaryl ring are independently of each other selected from primary, secondary or tertiary alkyl or alkoxy with 1 to 40 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

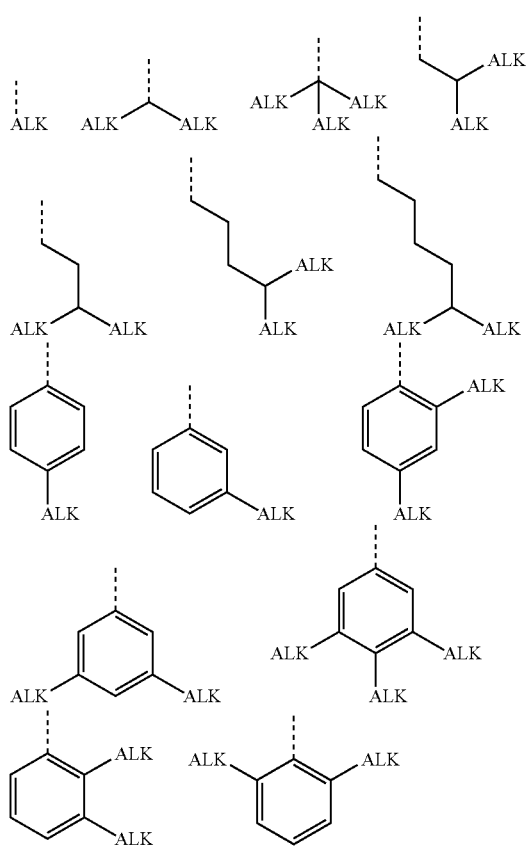

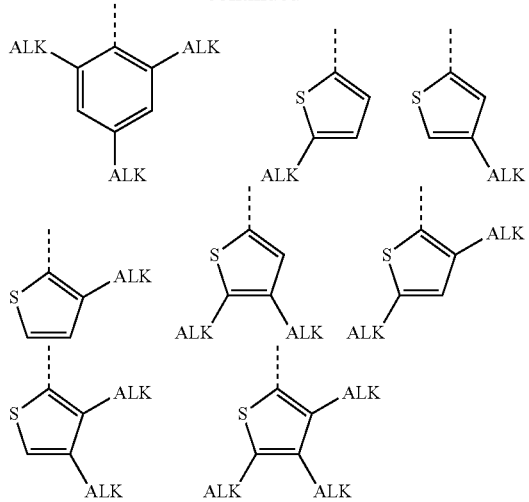

wherein "ALK" denotes optionally fluorinated, preferably linear, alkyl or alkoxy with 1 to 20, preferably 1 to 16 C-atoms, in case of tertiary groups very preferably 1 to 10 C atoms, and the dashed line denotes the link to the ring to which these groups are attached. Especially preferred among these groups are those wherein all ALK subgroups are identical.

As used herein, if an aryl(oxy) or heteroaryl(oxy) group is "alkylated or alkoxylated", this means that it is substituted with one or more alkyl or alkoxy groups having from 1 to 20 C-atoms and being straight-chain or branched and wherein one or more H atoms are optionally substituted by an F atom.

Above and below, $Y^1$ and $Y^2$ are independently of each other H, F, Cl or CN.

As used herein, —CO—, —C(=O)— and —C(O)— will be understood to mean a carbonyl group, i.e. a group having the structure

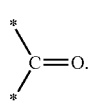

As used herein, C=CR$^1$R$^2$ etc. will be understood to mean a group having the structure

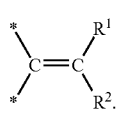

Unless stated otherwise "optionally substituted" without mentioning the substitutent means optionally substituted by L.

As used herein, "halogen" includes F, Cl, Br or I, preferably F, Cl or Br. A halogen atom that represents a substituent on a ring or chain is preferably F or Cl, very preferably F. A halogen atom that represents a reactive group in a monomer is preferably Cl, Br or I, very preferably Br or I.

Above and below the phrase "and its mirror images" means to include a moiety obtainable from another moiety by flipping it at least once vertically and/or horizontally across an external symmetry plane or a symmetry plane extending through the moiety. For example, in case of the moiety

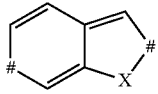

the phrase "and its mirror image" means to include the following moieties

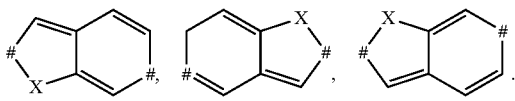

DETAILED DESCRIPTION

The compounds of the present invention are easy to synthesize and exhibit advantageous properties. They show good processibility for the device manufacture process, high solubility in organic solvents, and are especially suitable for large scale production using solution processing methods.

The compounds of formula I are especially suitable as (electron) acceptor or n-type semiconductor, and for the preparation of blends of n-type and p-type semiconductors which are suitable for use in OPD or BHJ OPV devices.

The compounds of formula I are further suitable to replace the fullerene compounds that have hitherto been used as n-type semiconductor in OPV or OPD devices.

Besides, the compounds of formula I show the following advantageous properties:
i) The extended quinoidal structures to yield n-type semiconducting materials of high electron mobility due to the ease of electron injection to release aromatisation energy from the molecules.
ii) The solubility of the compound can easily be optimized by selection of the solubilising groups $R^{1-4}$ on the fused cylopentadiene moieties.
iii) Solubilising alkyl chains in the positions $R^{1-4}$ do also impart ease of synthesis and purification of the intermediates, and most importantly the processibility of the final compounds as semiconducting materials The synthesis of the compounds of formula I can be achieved based on methods that are known to the skilled person and described in the literature, as will be further illustrated herein.

The compounds of formula I are preferably selected from the following formulae

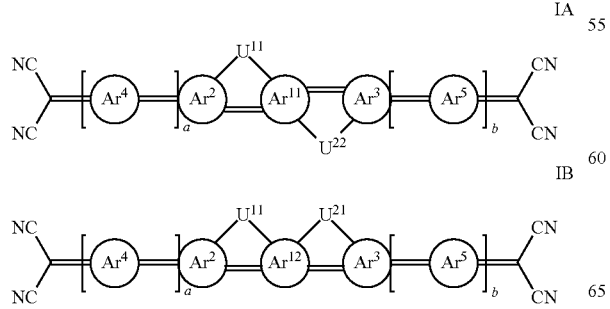

wherein $Ar^{11}$ and $Ar^{12}$ have one of the meanings given for $Ar^1$ in formula I, and $Ar^{2-5}$, $U^{11}$, $U^{21}$, $U^{22}$, a, b have the meanings given in formula I.

Preferably $Ar^2$, $Ar^3$, $Ar^4$ and $Ar^5$ in formula I and its subformulae denote a quinoidal alicyclic or heterocyclic group that has 5 to 30 ring atoms, is mono-, di-, tri-, tetra-, penta- or hexacyclic, optionally contains fused rings, and is unsubstituted or substituted by one or more identical or different groups $R^1$ or L as defined above.

Preferably $Ar^1$, $Ar^{11}$ and $Ar^{12}$ in formula I and its subformulae denote a quinoidal alicyclic or heterocyclic group, which is part of a larger quinoidal group formed together with $Ar^2$ and $Ar^3$, has 5 to 30 ring atoms, is mono-, di-, tri-, tetra-, penta- or hexacyclic, optionally contains fused rings, and is unsubstituted or substituted by one or more identical or different groups $R^1$ or L as defined above.

In a preferred embodiment of the present invention, $Ar^1$ in formula I and $Ar^{11}$ in formula IA are selected from the following formulae and their mirror images:

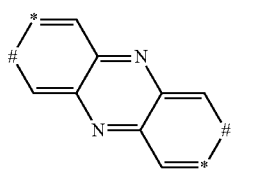
(9A)
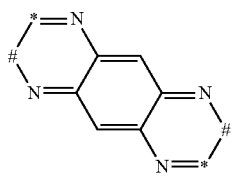
(10A)
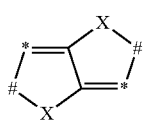
(11A)
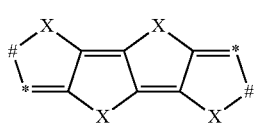
(12A)
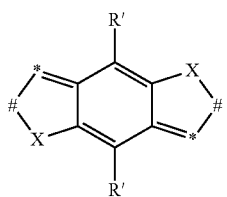
(13A)
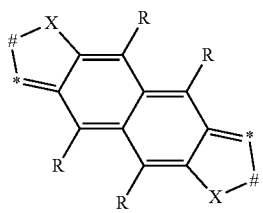
(14A)
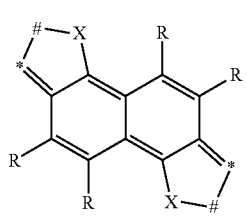
(15A)
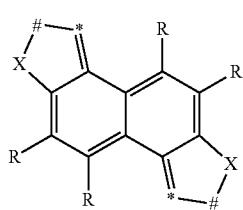
(16A)
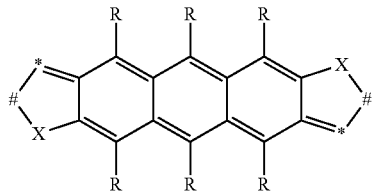
(17A)
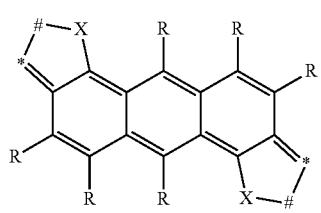
(18A)
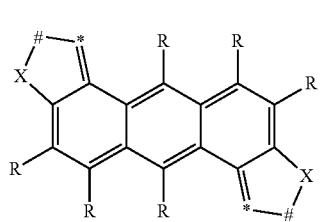
(19A)
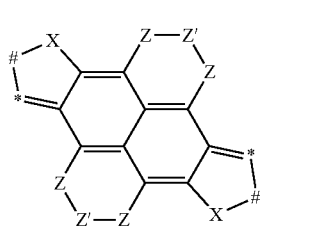
(20A)
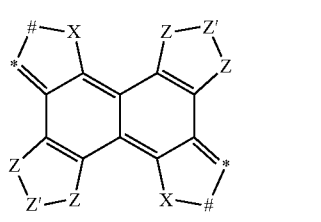
(21A)
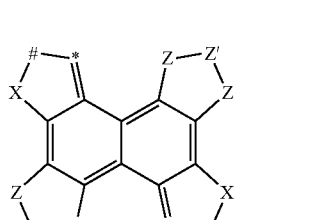
(22A)
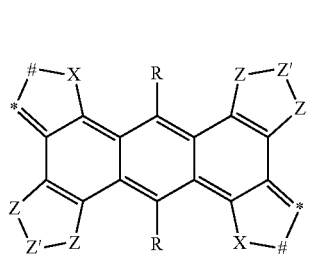
(23A)

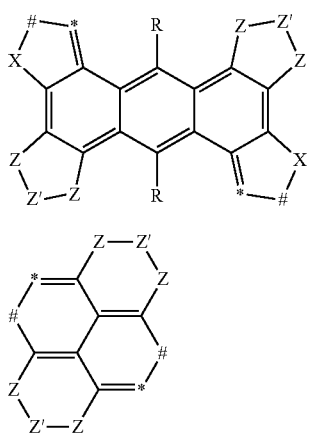 (24A)

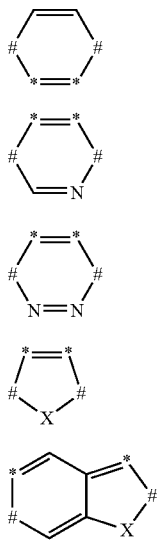 (25A)

wherein the individual radicals, independently of each other and on each occurrence identically or differently, have the following meanings
X O, S, Se or Te,
R, R' one of the meanings of $R^1$ or L as defined above and below,
an $sp^2$ carbon atom that is linked to the adjacent group in formula I, IA or IB via a C=C double bond, and
* an $sp^2$ carbon atom that is linked to the adjacent group in formula I, IA or IB via a C—C single bond,
Z, Z' O, S, Se, Te, C(=O), NR, =N— or =CR—, wherein at least one of Z and Z' is different from =N— and =CR—.

Preferred groups $Ar^1$ and $Ar^{11}$ are selected from the above formulae 1A-25A and their mirror images wherein X is S.

Very preferred groups $Ar^1$ and $Ar^{11}$ are selected from formula 1A, 5A, 11A, 13A, 15A and 25A, wherein in formula 11A and 15A preferably X is S, in formula 13A preferably X is S and R' is different from H, and in formula 25A preferably Z is C=O and Z' is NR.

In another preferred embodiment of the present invention, $Ar^1$ in formula I and $Ar^{12}$ in formula IB are selected from the following formulae and their mirror images:

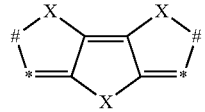 (1B)

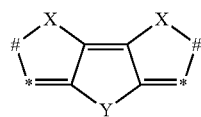 (2B)

(3B)

(4B)

(5B)

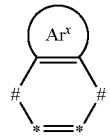 (6B)

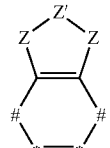 (7B)

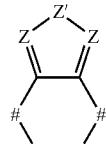 (8B)

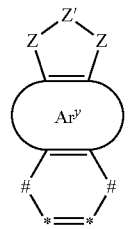 (9B)

(10B)

(11B)

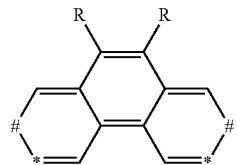 (12B)

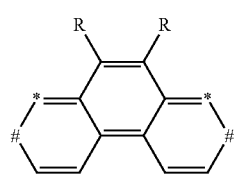 (13B)

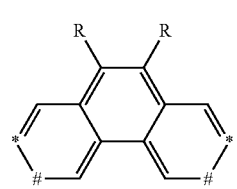 (14B)

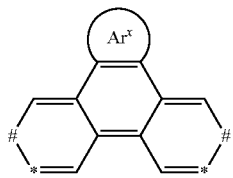
(15B)

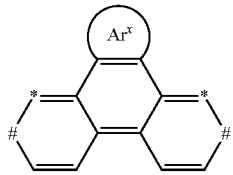
(16B)

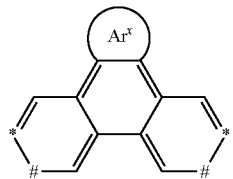
(17B)

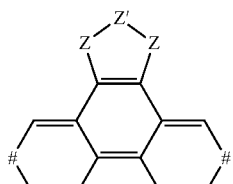
(18B)

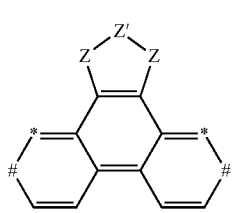
(19B)

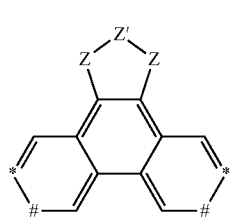
(20B)

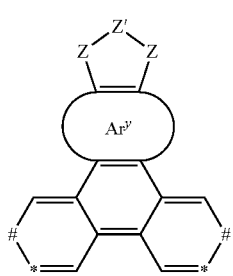
(21B)

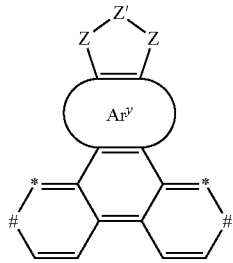
(22B)

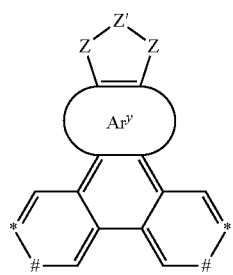
(23B)

wherein the individual radicals, independently of each other and on each occurrence identically or differently, have the following meanings X, Z, Z', R, # and * have the meanings or preferred meanings as given above and below, $Ar^x$, $Ar^y$ a fused 5- or 6-membered aromatic ring wherein one or more CH groups are optionally replaced by O, S, Se, Te, =N—, NR or C(=O), and one or more H atoms are optionally replaced by $R^1$ or L, Y $CR^1R^2$, $SiR^1R^2$, $GeR^1R^2$, NR, C(=O) or S(=O), with $R^1$ and $R^2$ being as defined above.

Very preferred groups $Ar^1$ and $Ar^{12}$ are selected from the above formulae 1 B-23B and their mirror images wherein X is S and Y is $CR^1R^2$.

Preferred groups $Ar^x$ are selected from the following formulae

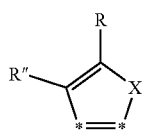
(X1)

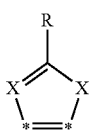
(X2)

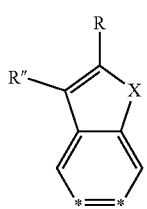
(X3)

-continued (X4)
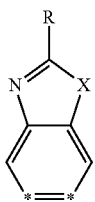

wherein X, R and * have the meanings or preferred meanings as given above and below, R'' has one of the meanings of R and is preferably H.

Preferred groups Ar^y are selected from the following formulae

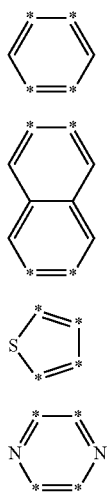

(Y1)

(Y2)

(Y3)

(Y4)

wherein * has the meaning as given above.

Very preferred groups $Ar^{12}$ are selected from formula 1B, 4B, 6B, 7B, 8B, 9B, 10B and 11B. Therein preferably $Ar^x$ is of formula X1 or X2, $Ar^y$ is of formula Y1 or Y3, X is S, Y is $CR^1R^2$ or NR, Z' is NR, =N— or =CR—, Z is =N— or C(=O), or one of the two groups Z is =N— or =CR— and the other is O or S.

In a preferred embodiment of the present invention, $Ar^2$ and $Ar^3$ in formula I, IA and IB are selected from the following formulae and their mirror images:

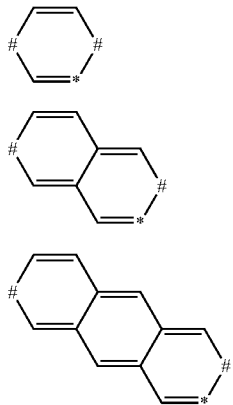

(1C)

(2C)

(3C)

-continued

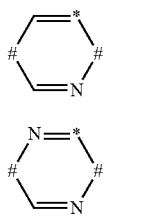

(4C)

(5C)

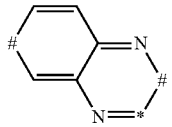

(6C)

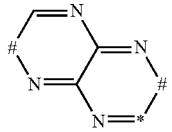

(7C)

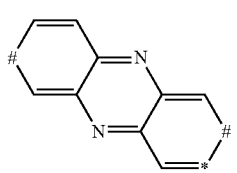

(8C)

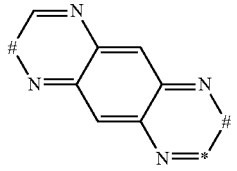

(9C)

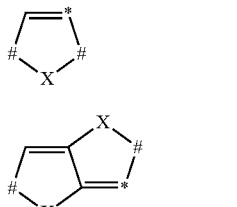

(10C)

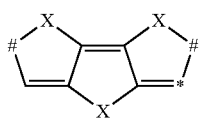

(11C)

(12C)

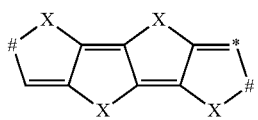

(13C)

(14C)

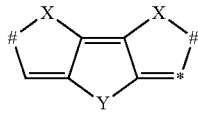

(15C)

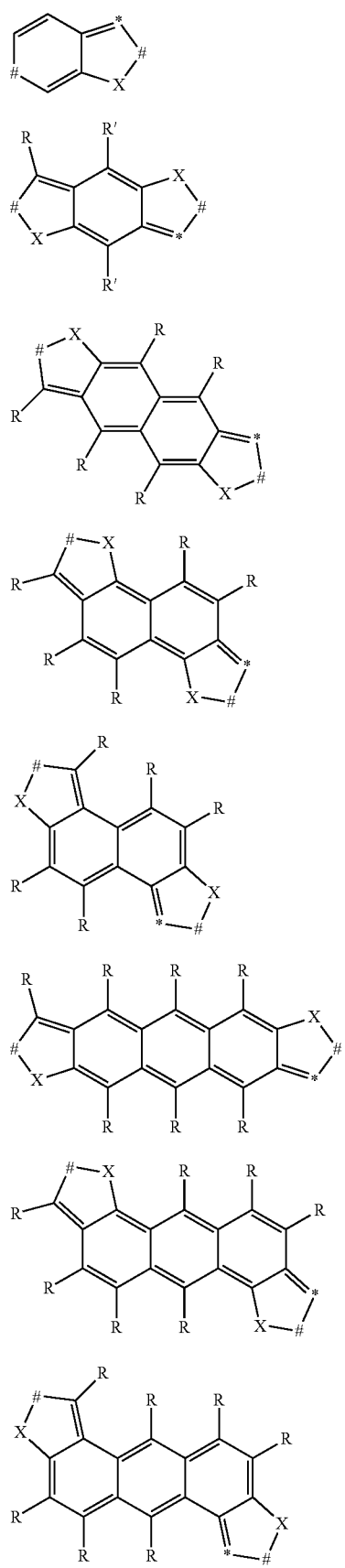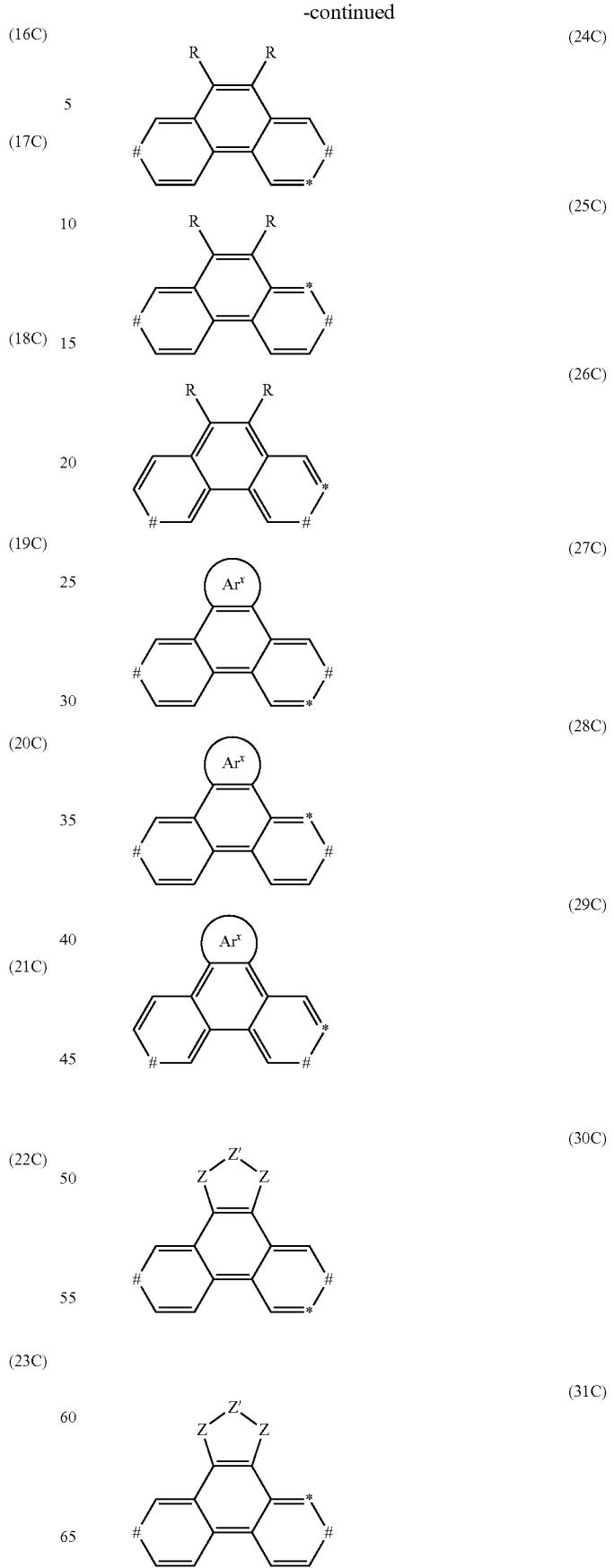

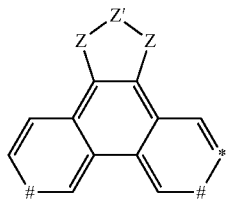 (32C)

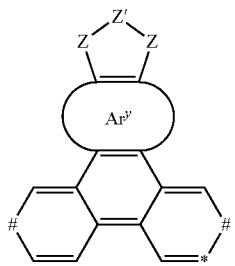 (33C)

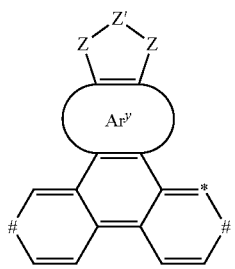 (34C)

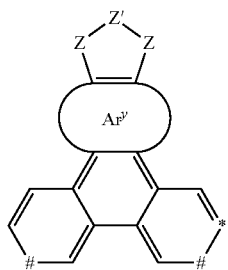 (35C)

wherein Ar$^x$, Ar$^y$, R, R', X, Y, Z, Z', # and * have the meanings or preferred meanings as given above and below.

Very preferred groups Ar$^2$ and Ar$^3$ are selected from the above formulae 1C-35C and their mirror images wherein X is S and Y is CR$^1$R$^2$ or NR.

Particularly preferred groups Ar$^2$ and Ar$^3$ are selected from formula 10, 110, 12C, 13C, 15C and 16C, wherein preferably X is S.

In a preferred embodiment of the present invention, Ar$^4$ and Ar$^5$ in formula I, IA and IB are selected from the following formulae and their mirror images:

 (1D)

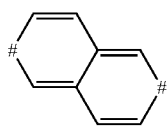 (2D)

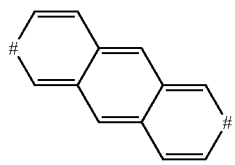 (3D)

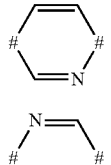 (4D)

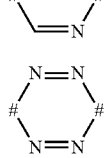 (5D)

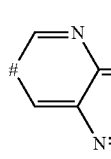 (6D)

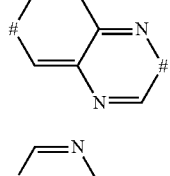 (7D)

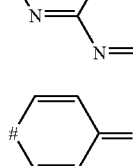 (8D)

(9D)

(10D)

(11D)

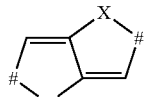 (12D)

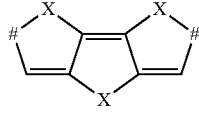 (13D)

(14D)

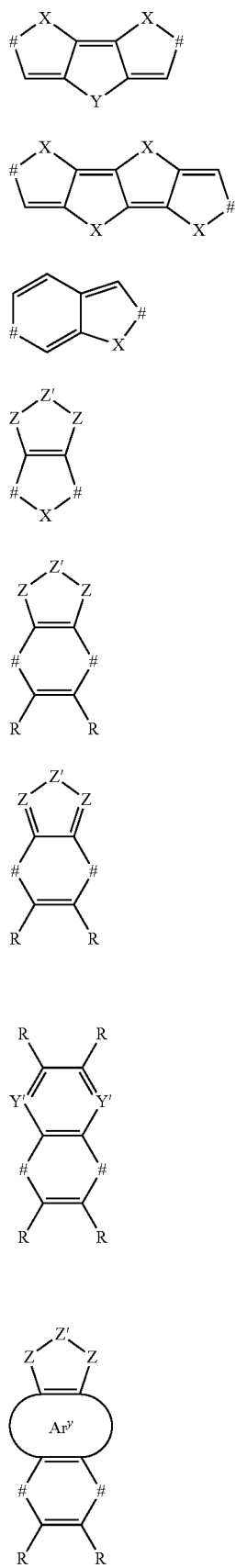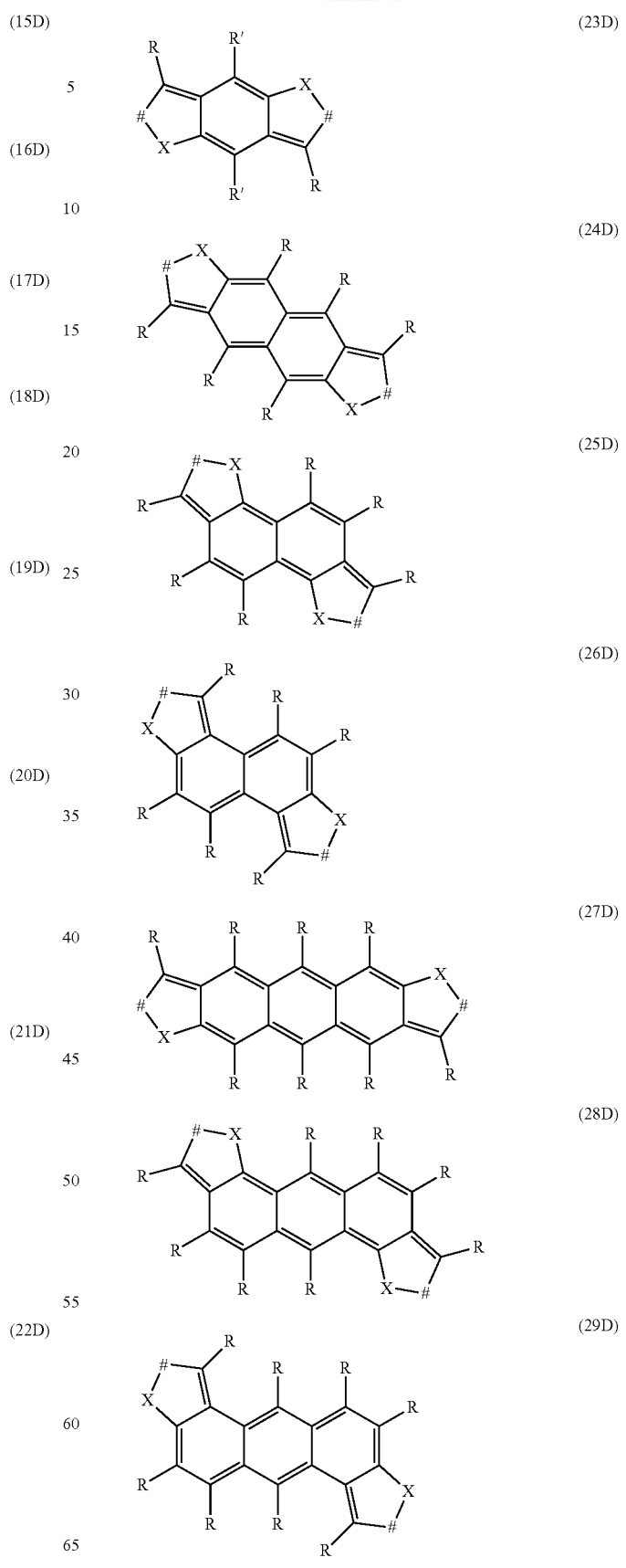

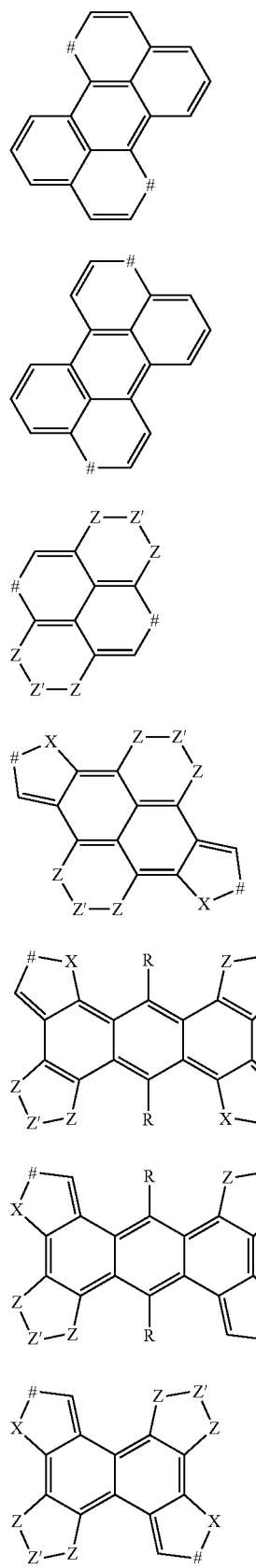
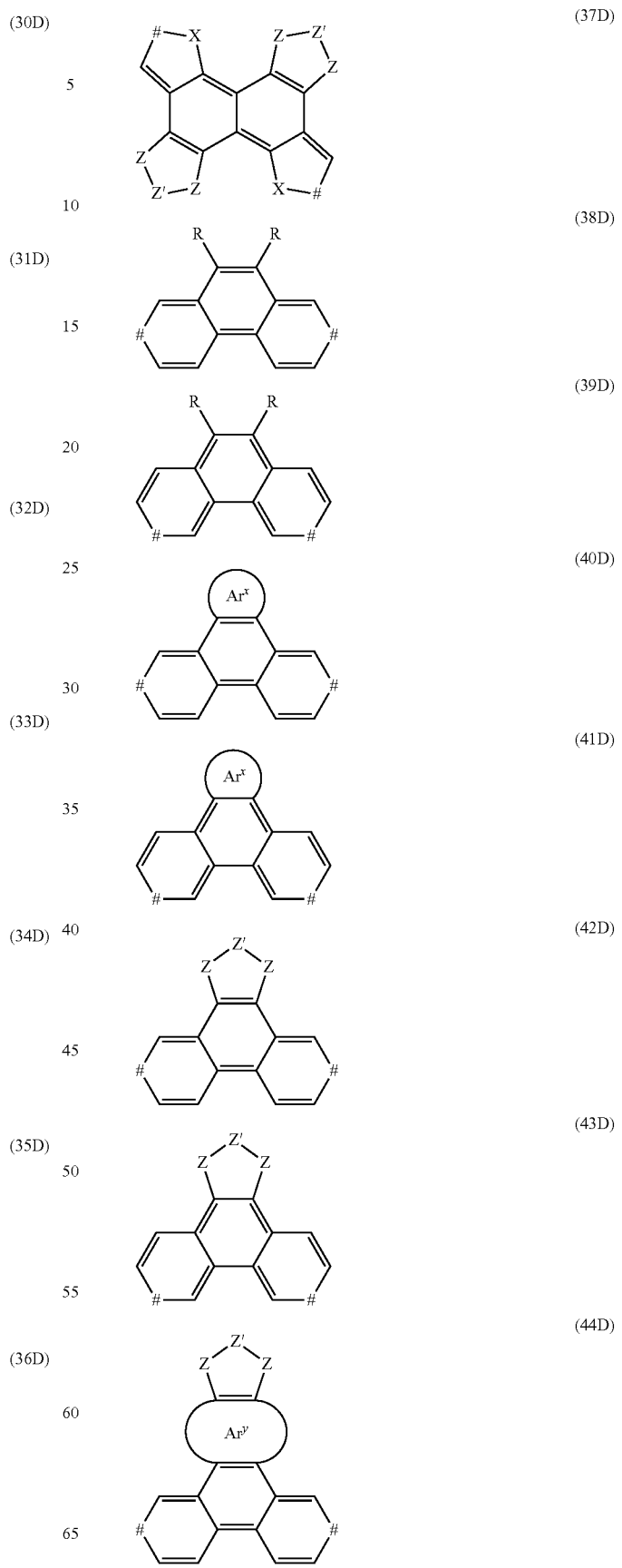

(45D)

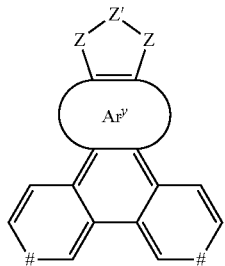

wherein Ar$^x$, Ar$^y$, R, R', X, Y, Z, Z', # and * have the meanings or preferred meanings as given above and below, and Y' denotes N or CR Very preferred groups Ar$^4$ and Ar$^5$ are selected from the above formulae 1 D-45D and their mirror images wherein X is S and Y is CR$^1$R$^2$ or NR.

Further preferred groups Ar$^4$ and Ar$^5$ are selected from formulae 1 D, 5D, 12D, 13D, 17D, 18D, 19D, 20D, 21 D, 22D and 23D and their subformulae, wherein X is preferably S.

Very preferred groups Ar$^4$ and Ar$^5$ are selected from the following subformulae and their mirror images:

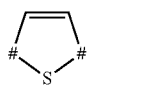 (12D1)

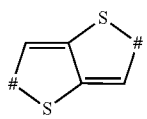 (13D1)

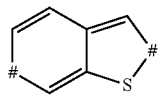 (17D1)

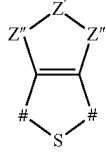 (18D1)

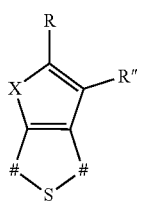 (18D2)

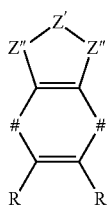 (19D1)

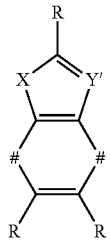 (19D2)

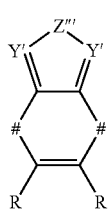 (20D1)

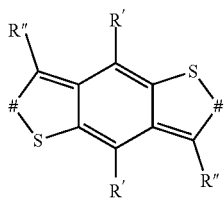 (23D1)

wherein R, R", X, Y' and # have the meanings or preferred meanings as given above and below and Z" and Z' have one of the meanings given for Z. Therein preferably R' is different from H, R" is H, X is S, Y' is N, Z' is NR and Z" is C(=O), or Z' is =N— or =CR— and one of the two groups Z" is =N— or CR and the other is O or S, Z''' is NR, O or S.

Very preferred groups of formula 18D1, 18D2, 19D1, 19D2 and 20D1 are selected from the following subformulae and their mirror images:

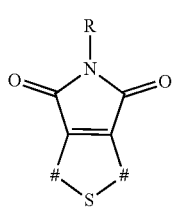 (18D1a)

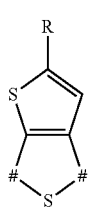 (18D2a)

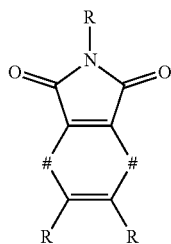

(19D1a)

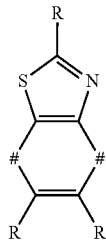

(19D2a)

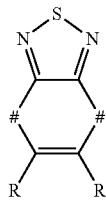

(20D1a)

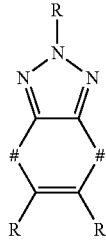

(20D1b)

wherein R and # have the meanings or preferred meanings as given above.

In a preferred embodiment the present invention the compounds of formula I and its subformulae and the groups $Ar^{1-5}$, $Ar^{11}$ and $Ar^{12}$ do not contain a cyclic and fused $sp^3$ carbon atom, i.e. an $sp^3$ carbon atom which is part of two fused rings and is not a spiro carbon atom.

In a preferred embodiment of the present invention, $R^{1-4}$ in formula I, IA, IB and their subformulae are selected from F, Cl or straight-chain or branched alkyl, alkoxy, sulfanylalkyl, sulfonylalkyl, alkylcarbonyl, alkoxycarbonyl and alkylcarbonyloxy, each having 1 to 40, preferably 1 to 20, C atoms and being unsubstituted or substituted by one or more F atoms.

In another preferred embodiment of the present invention, $R^{1-4}$ in formula I, IA, IB and their subformulae are selected from mono- or polycyclic aryl or heteroaryl, each of which is optionally substituted with one or more groups L as defined in formula I and has 4 to 30 ring atoms, and wherein two or more rings may be fused to each other or connected with each other by a covalent bond.

In a preferred embodiment of the present invention, one or more, preferably all, groups R in formula 1A-25A, 1 B-23B, 1C-35C, 1 D-45D and their subformulae are H.

In another preferred embodiment of the present invention, at least one of the groups R in formula 1A-25A, 1 B-23B, 1C-35C, 1D-45D and their subformulae is different from H.

In formula 13A, 17C and 23D preferably R is H and R' is different from H.

In a preferred embodiment of the present invention, R and R' in formulae 1A-25A, 1 B-23B, 1C-35C, 1D-45D and their subformulae, when being different from H, are selected from F, Cl or straight-chain or branched alkyl, alkoxy, sulfanylalkyl, sulfonylalkyl, alkylcarbonyl, alkoxycarbonyl and alkylcarbonyloxy, each having 1 to 40, preferably 1 to 20, C atoms and being unsubstituted or substituted by one or more F atoms.

In another preferred embodiment of the present invention, R and R' in formulae 1A-25A, 1 B-23B, 1C-35C, 1D-45D and their subformulae, when being different from H, are selected from aryl or heteroaryl, each of which is optionally substituted with one or more groups L as defined in formula I and has 4 to 30 ring atoms.

Preferred aryl and heteroaryl groups $R^{1-4}$, R and R' are selected from the following formulae.

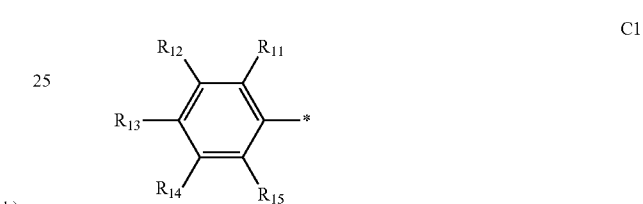

C1

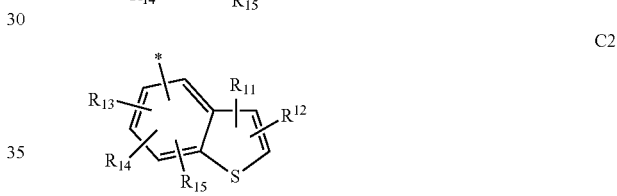

C2

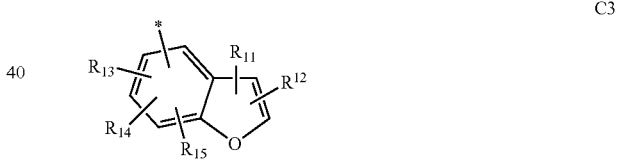

C3

C4

C5

C6

C7

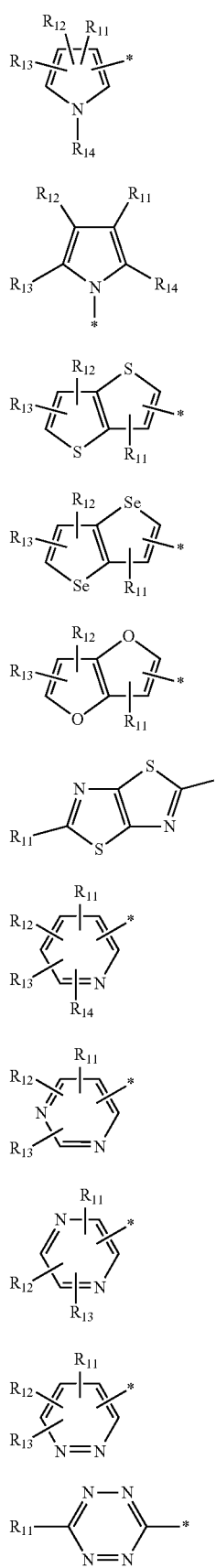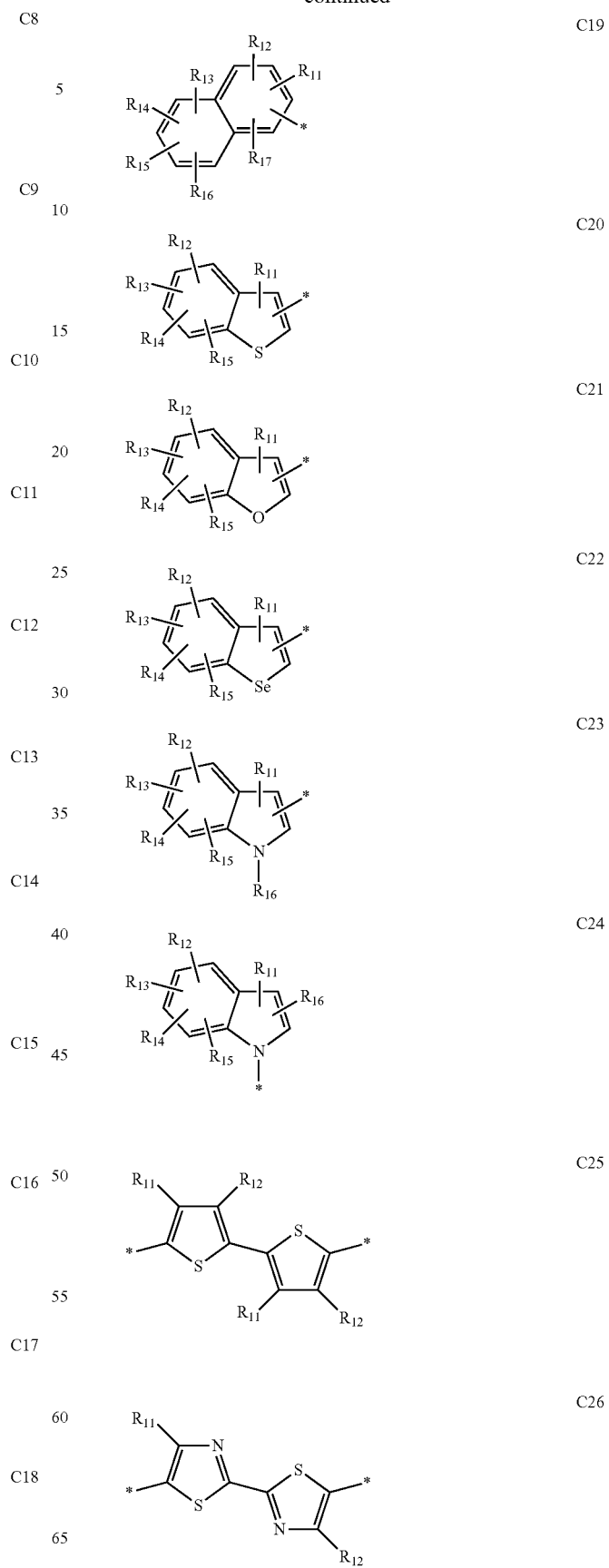

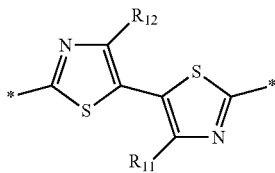

C27 wherein $R^{11-17}$, independently of each other, and on each occurrence identically or differently, denote H or have one of the meanings given for L in formula I or one of its preferred meanings as given above and below.

Very preferred aryl and heteroaryl groups $R^{1-4}$, R and R' are selected from the following formulae

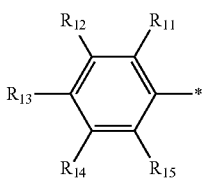

C1-1

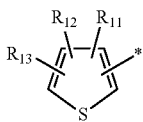

C4-1

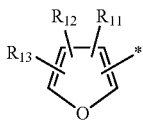

C5-1

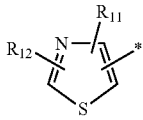

C7-1

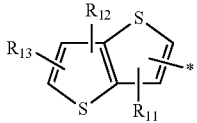

C10-1 wherein $R^{11-15}$ are as defined above.

In another preferred embodiment one or more of $R^{1-4}$, R or R' denote a straight-chain, branched or cyclic alkyl group with 1 to 50, preferably 2 to 50, very preferably 2 to 30, more preferably 2 to 24, most preferably 2 to 16 C atoms, in which one or more $CH_2$ or $CH_3$ groups are replaced by a cationic or anionic group.

The cationic group is preferably selected from the group consisting of phosphonium, sulfonium, ammonium, uronium, thiouronium, guanidinium or heterocyclic cations such as imidazolium, pyridinium, pyrrolidinium, triazolium, morpholinium or piperidinium cation.

Preferred cationic groups are selected from the group consisting of tetraalkylammonium, tetraalkylphosphonium, N-alkylpyridinium, N,N-dialkylpyrrolidinium, 1,3-dialkylimidazolium, wherein "alkyl" preferably denotes a straight-chain or branched alkyl group with 1 to 12 C atoms.

Further preferred cationic groups are selected from the group consisting of the following formulae

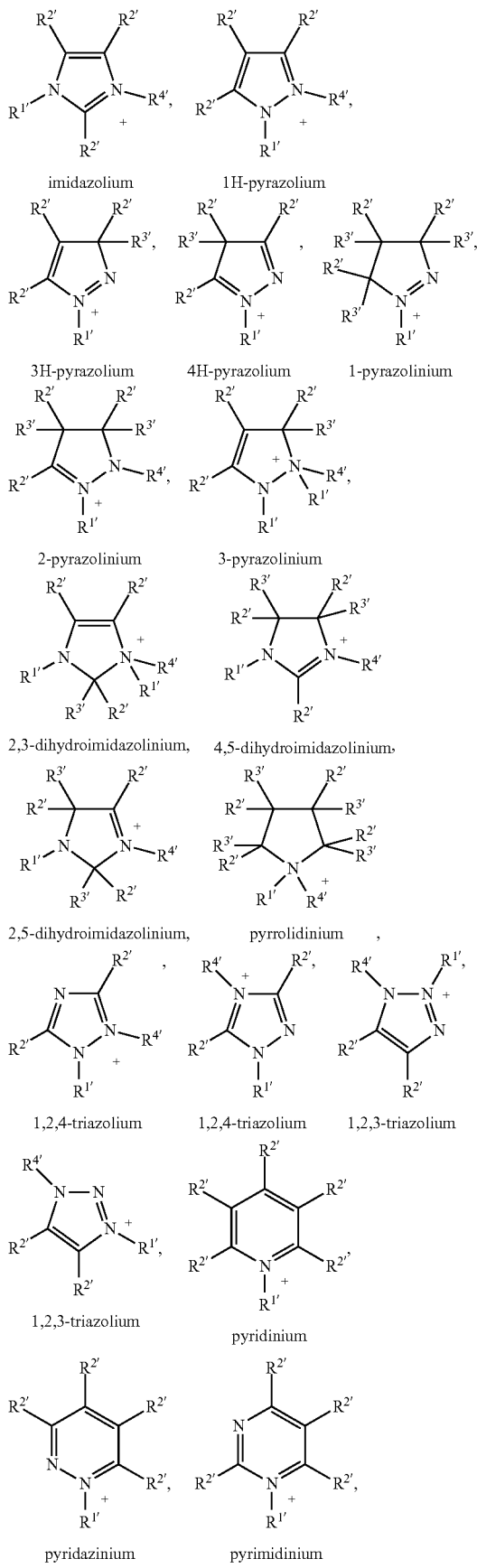

-continued

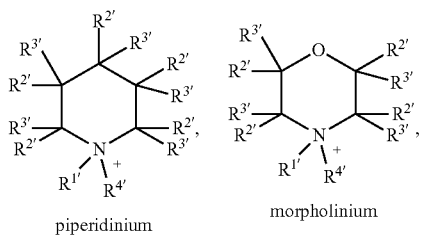
piperidinium  morpholinium

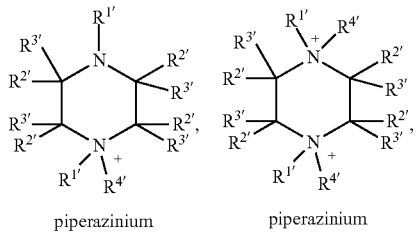
piperazinium  piperazinium

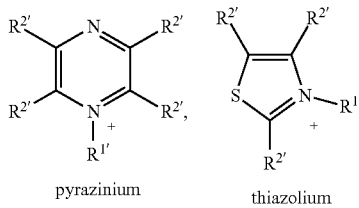
pyrazinium  thiazolium

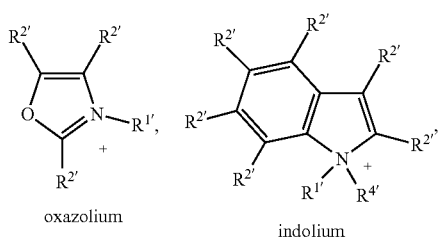
oxazolium  indolium

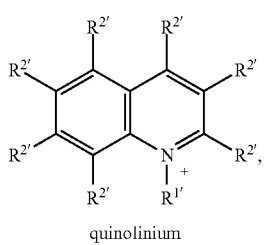
quinolinium

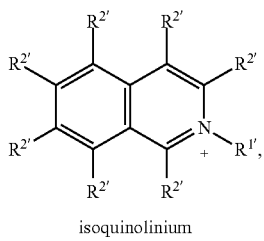
isoquinolinium

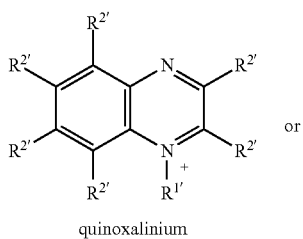
quinoxalinium

-continued

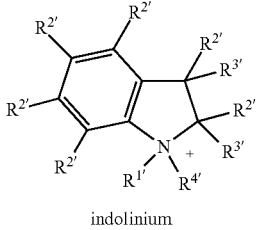
indolinium wherein $R^{1'}$, $R^{2'}$, $R^{3'}$ and $R^{4'}$ denote, independently of each other, H, a straight-chain or branched alkyl group with 1 to 12 C atoms or non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents L as defined above, or denote a link to the respective group $R^{1-9}$.

In the above cationic groups of the above-mentioned formulae any one of the groups $R^{1'}$, $R^{2'}$, $R^{3'}$ and $R^{4'}$ (if they replace a $CH_3$ group) can denote a link to the respective group $R^{1-9}$, or two neighbored groups $R^{1'}$, $R^{2'}$, $R^{3'}$ or $R^{4'}$ (if they replace a $CH_2$ group) can denote a link to the respective group $R^{1-9}$.

The anionic group is preferably selected from the group consisting of borate, imide, phosphate, sulfonate, sulfate, succinate, naphthenate or carboxylate, very preferably from phosphate, sulfonate or carboxylate.

Further preferred compounds of formula I and its subformulae are selected from the following preferred embodiments or any combination thereof:

a and b are 0, a and b are 1, 2 or 3, one of a and b is 0 and the other is 1, 2 or 3, $U^{11}$, $U^{12}$, $U^{21}$, $U^{22}$, when being different from a C=C double bond, denote $CR^1R^2$ or $SiR^1R^2$, preferably $CR^1R^2$, X is S, Y is $CR^1R^2$ or NR, Z is =N— or C(=O), or one group Z is =N— or =CR— and the other is O or S, Z' is NR, =N— or =CR—, all substituents R are H, in formula 17C and 23D R is H and R' is different from H, $R^{1-4}$ are different from H, $R^{1-4}$ are selected from F, Cl or straight-chain or branched alkyl, alkoxy, sulfanylalkyl, sulfonylalkyl, alkylcarbonyl, alkoxycarbonyl and alkylcarbonyloxy, each having 1 to 40, preferably 1 to 20, C atoms and being unsubstituted or substituted by one or more F atoms, preferably from F, or alkyl or alkoxy having 1 to 16 C atoms that is optionally fluorinated, $R^{1-4}$ are selected from aryl or heteroaryl, each of which is optionally substituted with one or more groups L as defined in formula I and has 4 to 30 ring atoms, preferably from phenyl that is optionally substituted, preferably in 4-position, with alkyl or alkoxy having 1 to 30 C atoms, preferably 1 to 16 C atoms, very preferably 4-alkylphenyl wherein alkyl is C1-16 alkyl, most preferably 4-methylphenyl or 4-hexylphenyl, L' is H, L, L' denote F, Cl, CN, NO$_2$, or alkyl or alkoxy with 1 to 16 C atoms that is optionally fluorinated, R is H, at least one R is different from H, when R is different from H it is selected from F, Cl or straight-chain or branched alkyl, alkoxy, sulfanylalkyl, sulfonylalkyl, alkylcarbonyl, alkoxycarbonyl and alkylcarbonyloxy, each having 1 to 40, preferably 1 to 20, C atoms and being unsubstituted or substituted by one or more F atoms, without being perfluorinated, preferably from F, or alkyl or alkoxy having 1 to 16 C atoms that is optionally fluorinated, R' is selected from F, Cl or straight-chain or branched alkyl, alkoxy, sulfanylalkyl, sulfonylalkyl, alkylcarbonyl, alkoxycarbonyl and alkylcarbonyloxy, each having 1 to 40, preferably 1 to 20, C atoms and being unsubstituted or substituted by one or more F atoms, without being perfluorinated, preferably from F, or alkyl or alkoxy having 1 to 16 C atoms that is optionally fluorinated, R' is selected from aryl or heteroaryl, each of which is optionally substituted with one or more groups L as defined in formula I and has 4 to 30 ring atoms, preferably from phenyl that is optionally substituted.

Preferred compounds of formula I and IA are selected from the following subformulae

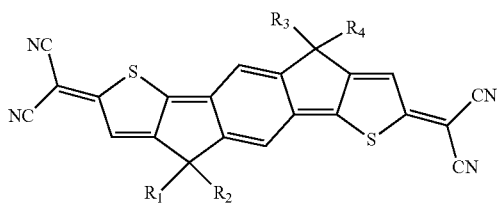

I1

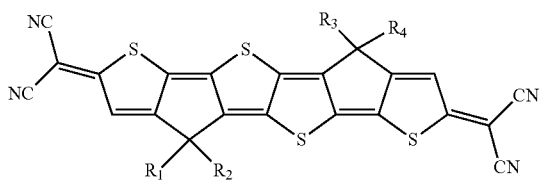

I2

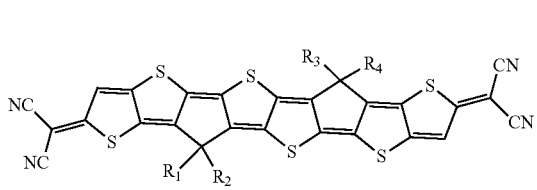

I4

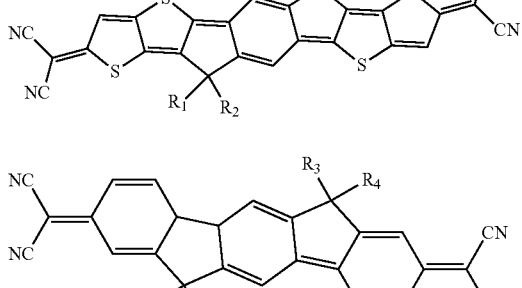

I3

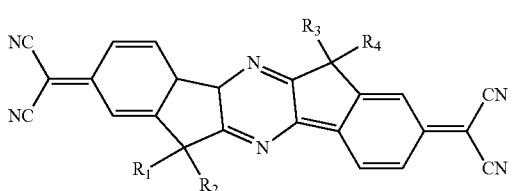

I6

I5

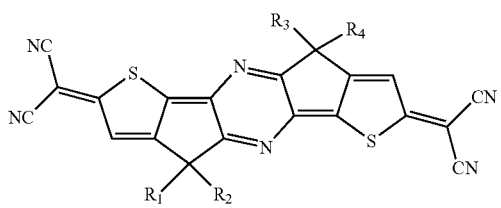

I7

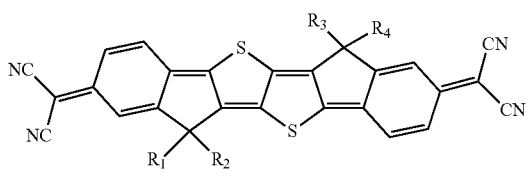

I8

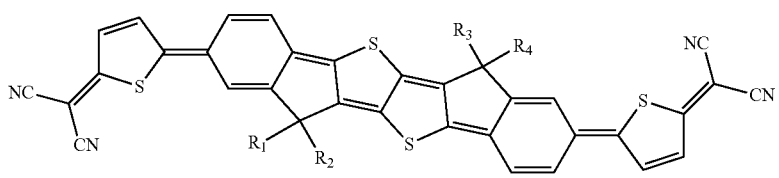

I9

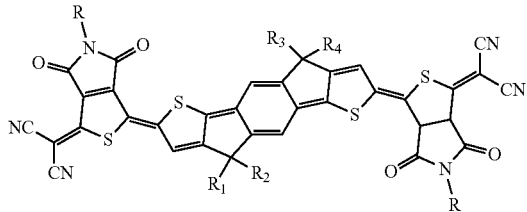

I10

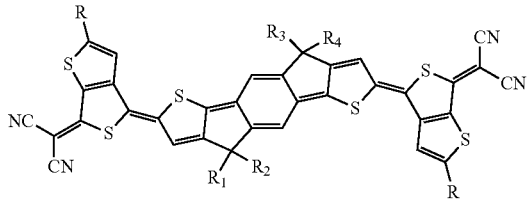

I11

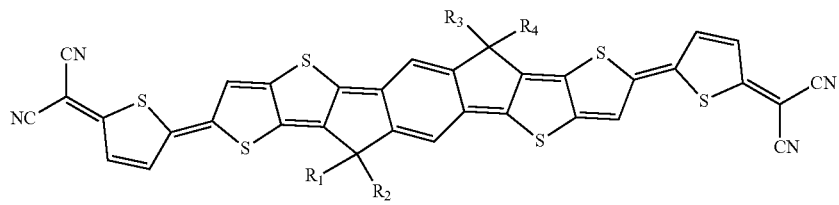
I12
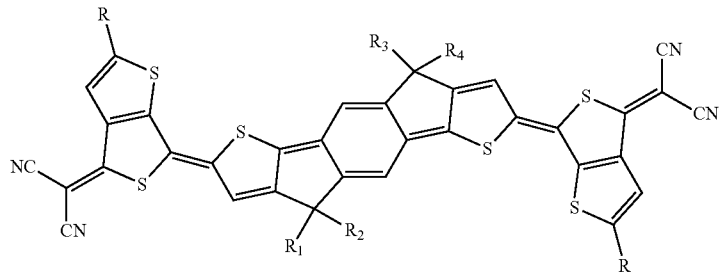
I13
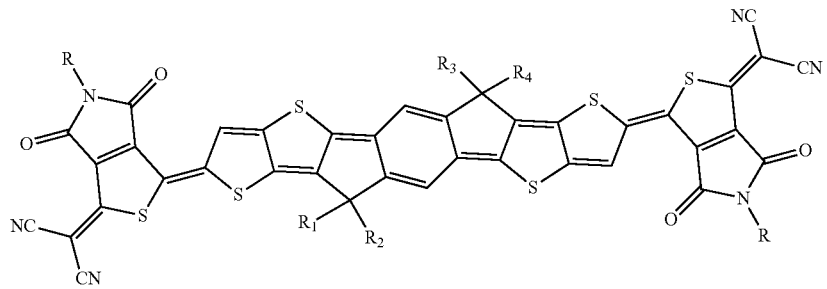
I14
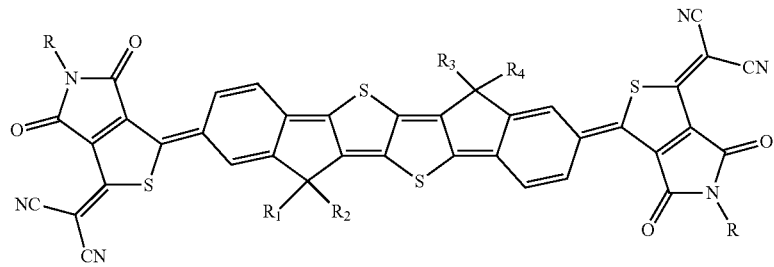
I15
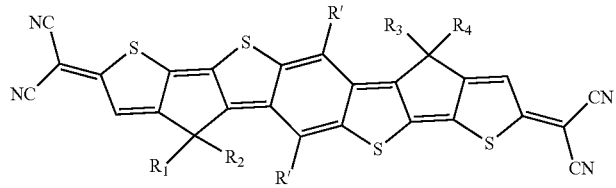
I16
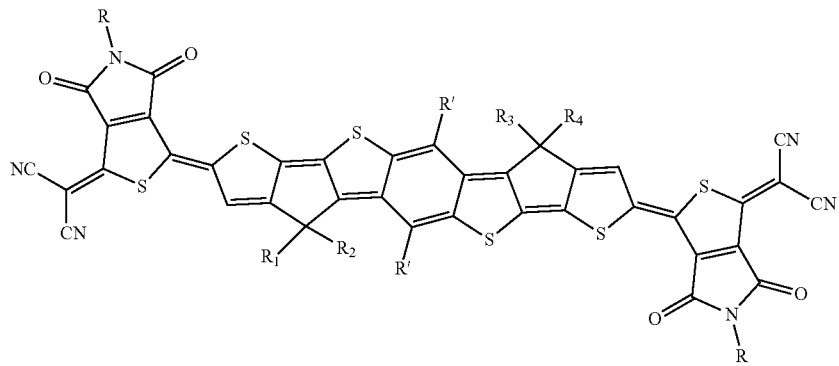
I17

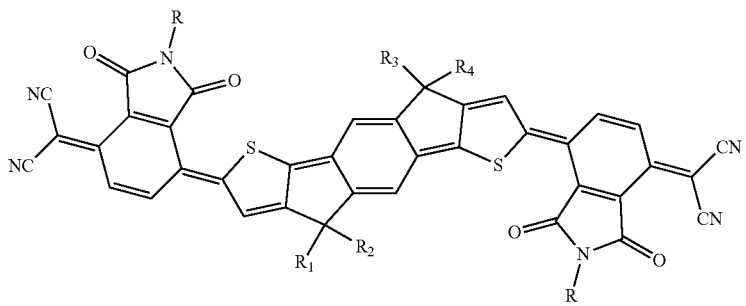

I18

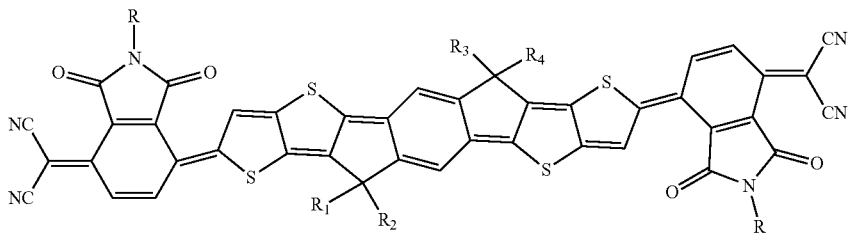

I19

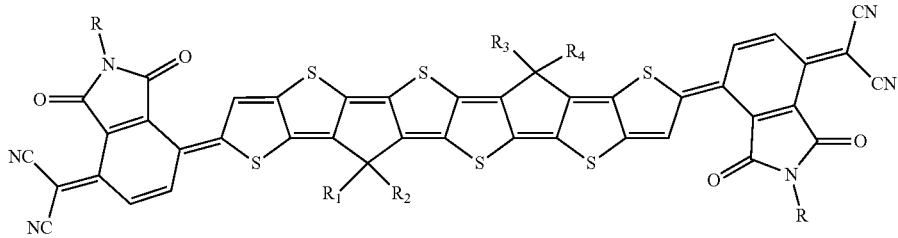

I20 wherein $R^{1-4}$, $R^5$, R and R' have the meanings given above and below.

Preferably in formulae I1-I20 R is selected from alkyl or alkoxy having 1 to 40, preferably 1 to 20, C atoms that is optionally fluorinated.

Preferably in formulae I1-I20 $R^{1-4}$ and R' are selected from alkyl or alkoxy having 1 to 40, preferably 1 to 20, C atoms that is optionally fluorinated.

Further preferably in formulae I1-I20 $R^{1-4}$ and R' are selected from aryl or heteroaryl having 4 to 30 ring atoms that is mono- or polycyclic, optionally contains fused rings, and optionally substituted with one or more groups L as defined in formula I, preferably from phenyl that is optionally substituted, preferably in 4-position, with alkyl or alkoxy having 1 to 40, preferably 1 to 20, C atoms or from thiophene that is optionally substituted, preferably in 5-position, with alkyl or alkoxy having 1 to 40, preferably 1 to 20, C atoms.

Another embodiment of the invention relates to a composition comprising a compound of formula I, and further comprising one or more electron donors or p-type semiconductors, preferably selected from conjugated polymers.

In a first preferred embodiment the electron donor or p-type semiconductor is a conjugated polymer that comprises at least one electron donating unit ("donor unit") and at least one electron accepting unit ("acceptor unit"), and optionally at least one spacer unit separating a donor unit from an acceptor unit,
wherein each donor and acceptor units is directly connected to another donor or acceptor unit or to a spacer unit, and wherein all of the donor, acceptor and spacer units are selected from arylene or heteroarylene that has from 5 to 20 ring atoms, is mono- or polycyclic, optionally contains fused rings, are is unsubstituted or substituted by one or more identical or different groups L as defined above.

Preferably the spacer units, if present, are located between the donor and acceptor units such that a donor unit and an acceptor unit are not directly connected to each other.

Preferred conjugated polymers comprise, very preferably consist of, one or more units of the formula U1 and one or more units of the formula U2

-(D-Sp)-    U1

-(A-Sp)-    U2 wherein D denotes a donor unit, A denotes an acceptor unit and Sp denotes a spacer unit, all of which are selected from arylene or heteroarylene that has from 5 to 20 ring atoms, is mono- or polycyclic, optionally contains fused rings, are is unsubstituted or substituted by one or more identical or different groups L as defined above.

Very preferred are polymers of formula Pi and Pii

-[(D-Sp)$_x$-(A-Sp)$_y$]$_n$-    Pi

-[(D-A)$_x$-(A-Sp)$_y$]$_n$-    Pii wherein A, D and Sp are as defined in formula U1 and U2, x denotes the molar fraction of the units (D-Sp) or (D-A), y denotes the molar fraction of the units (A-Sp), x and y are each, independently of one another >0 and <1, with x+y=1, and n is an integer >1.

In the polymers of formula P1 and P2 and their subformulae, x and y are preferably from 0.1 to 0.9, very preferably from 0.3 to 0.7, most preferably from 0.4 to 0.6.

Preferred donor units or units D are selected from the following formulae
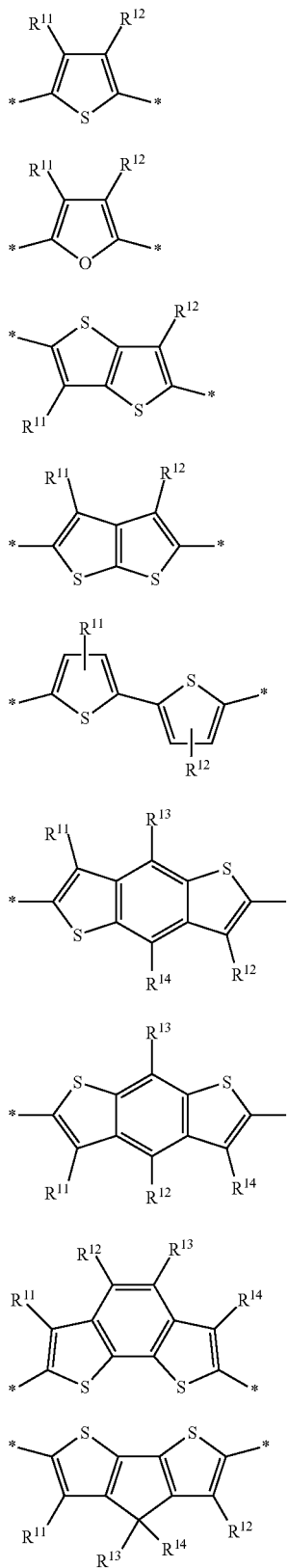
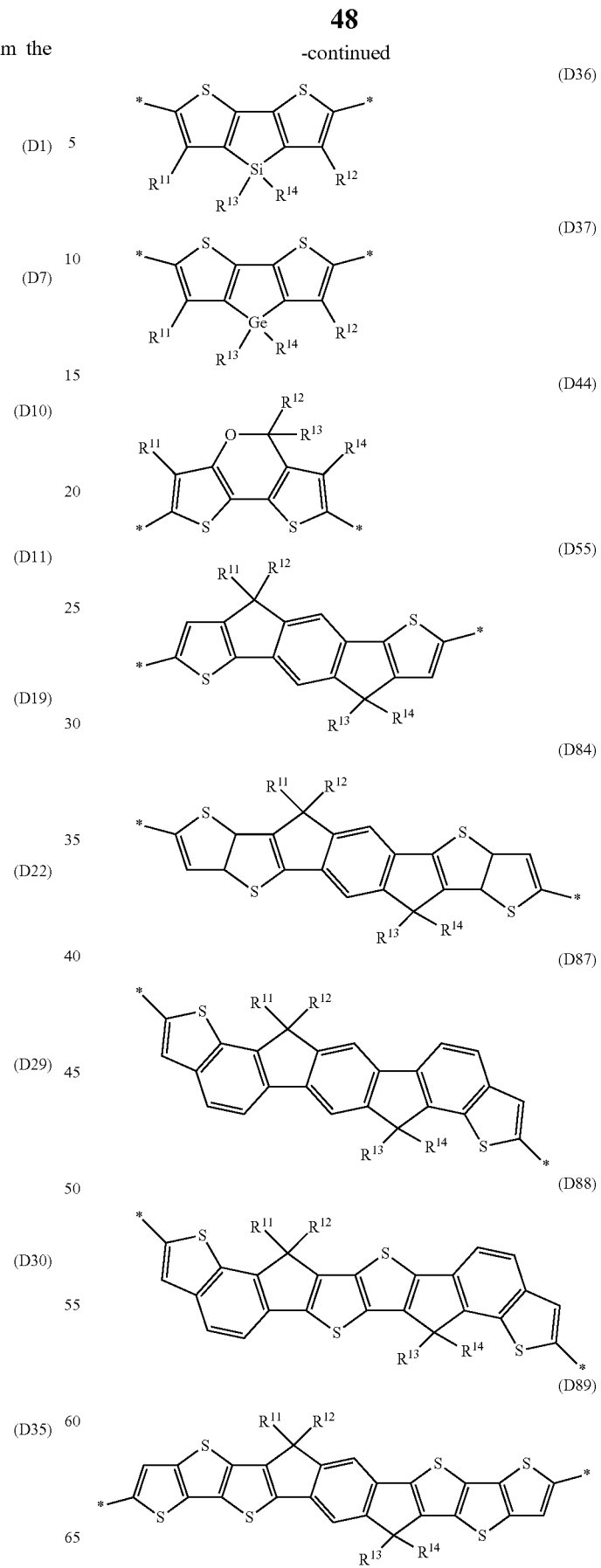

-continued
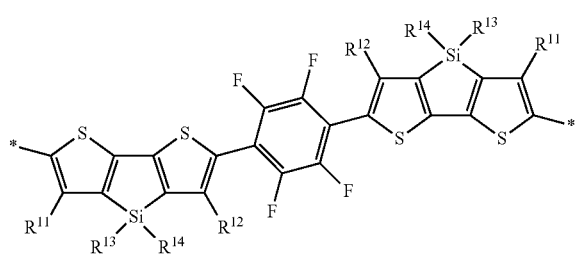
(D93)
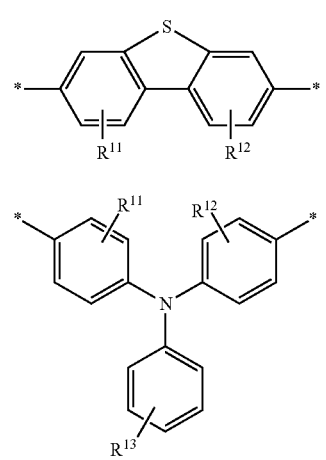
(D106)
(D111)
(D140)
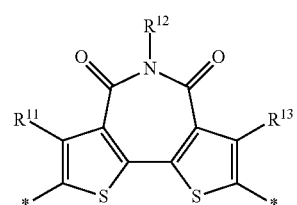
(D141)
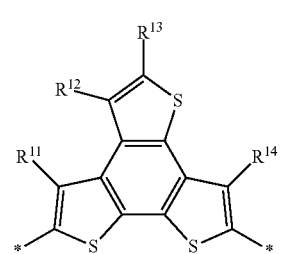
(D146)
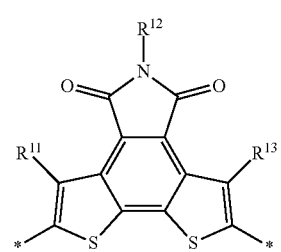
(D147)
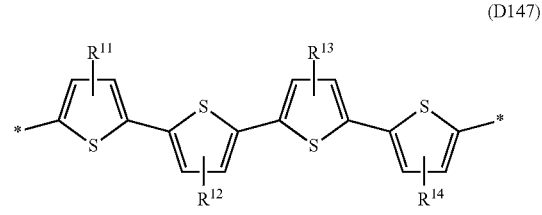
wherein $R^{11}$, $R^{12}$, $R^{13}$, $R^{14}$ independently of each other denote H or have one of the meanings of L as defined above.
Preferred acceptor units or units A are selected from the following formulae
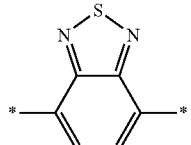
(A1)
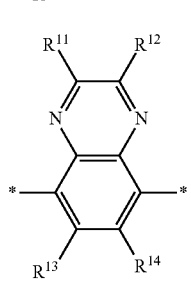
(A6)
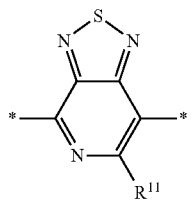
(A7)
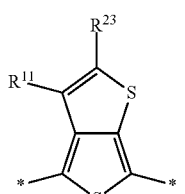
(A15)
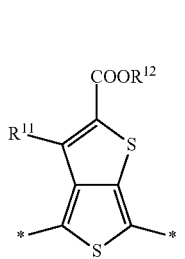
(A16)
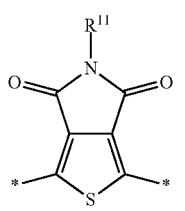
(A20)

-continued
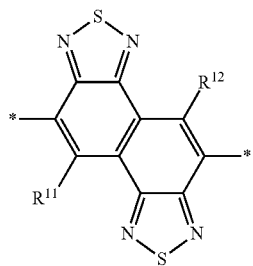
(A74)
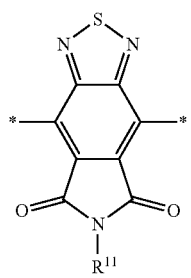
(A88)
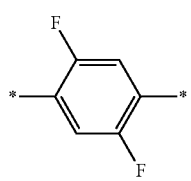
(A92)
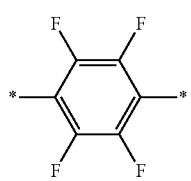
(A94)
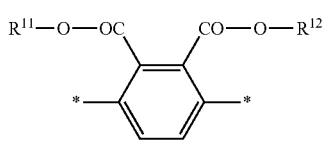
(A98)
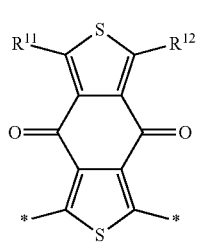
(A99)
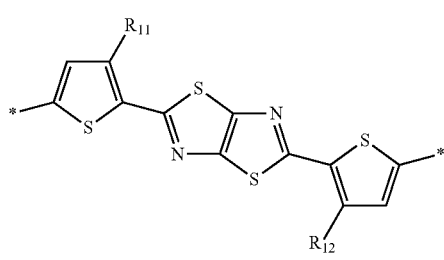
(A100)
wherein $R^{11}$, $R^{12}$, $R^{13}$, $R^{14}$ independently of each other denote H or have one of the meanings of L as defined above.
Preferred spacer units or units Sp are selected from the following formulae
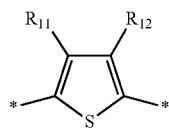
Sp1
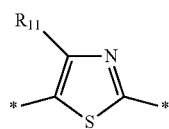
Sp2
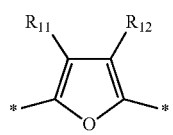
Sp3
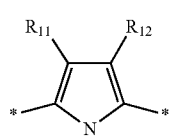
Sp4
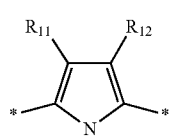
Sp5
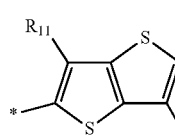
Sp6
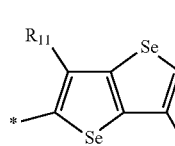
Sp7
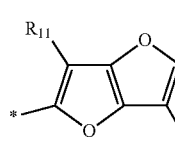
Sp8
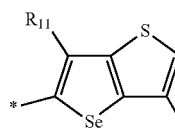
Sp9

-continued

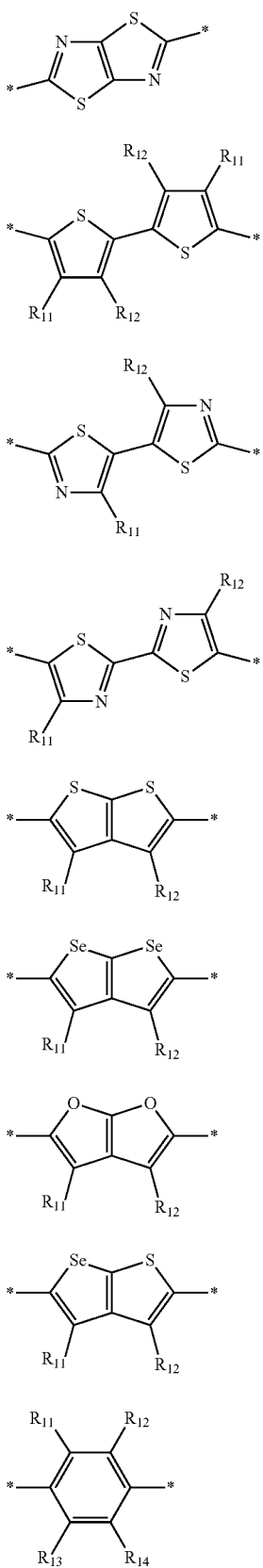

wherein $R^{11}$, $R^{12}$, $R^{13}$, $R^{14}$ independently of each other denote H or have one of the meanings of L as defined above.

In the formulae Sp1 to Sp17 preferably $R^{11}$ and $R^{12}$ are H. In formula Sp18 preferably $R^{11-14}$ are H or F.

Preferably the conjugated polymer contains, preferably consists of a) one or more donor units selected from the group consisting of the formulae D1, D7, D10, D11, D19, D22, D29, D30, D35, D36, D37, D44, D55, D84, D87, D88, D89, D93, D106, D111, D140, D141, D146, and D147 and/or b) one or more acceptor units selected from the group consisting of the formulae A1, A6, A7, A15, A16, A20, A74, A88, A92, A94, A98, A99 and A100, and c) optionally one or more spacer units selected from the group consisting of the formulae Sp1-Sp18, very preferably of the formulae Sp1, Sp6, Sp11 and Sp14, wherein the spacer units, if present, are preferably located between the donor and acceptor units such that a donor unit and an acceptor unit are not directly connected to each other.

In a second preferred embodiment the compound of formula I is a conjugated polymer that comprises, preferably consists of one or more, preferably one, two, three or four, distinct repeating units D, and one or more, preferably one, two or three, distinct repeating units A.

Preferably the conjugated polymer according to this second preferred embodiment contains from one to six, very preferably one, two, three or four distinct units D and from one to six, very preferably one, two, three or four distinct units A, wherein d1, d2, d3, d4, d5 and d6 denote the molar ratio of each distinct unit D, and a1, a2, a3, a4, a5 and a6 denote the molar ratio of each distinct unit A, and each of d1, d2, d3, d4, d5 and d6 is from 0 to 0.6, and d1+d2+d3+d4+d5+d6 is from 0.2 to 0.8, preferably from 0.3 to 0.7, and each of a1, a2, a3, a4, a5 and a6 is from 0 to 0.6, and a1+a2+a3+a4+a5+d6 is from 0.2 to 0.8, preferably from 0.3 to 0.7, and d1+d2+d3+d4+d5+d6+a1+a2+a3+a4+a5+a6 is from 0.8 to 1, preferably 1.

Preferably the conjugated polymer according to this second preferred embodiment contains, preferably consists of a) one or more donor units selected from the group consisting of the formulae D1, D7, D10, D11, D19, D22, D29, D30, D35, D36, D37, D44, D55, D84, D87, D88, D89, D93, D106, D111, D140, D141, D146, and D147 and/or b) one or more acceptor units selected from the group consisting of the formulae A1, A6, A7, A15, A16, A20, A74, A88, A92, A94, A98, A99 and A100.

In the above conjugated polymers, like those of formula P and its subformulae, the total number of repeating units n is preferably from 2 to 10,000. The total number of repeating units n is preferably ≥5, very preferably ≥10, most preferably ≥50, and preferably ≤500, very preferably 1,000, most preferably ≤2,000, including any combination of the aforementioned lower and upper limits of n.

The conjugated polymers are preferably statistical or random copolymers.

Very preferred conjugated polymers are selected from the following subformulae

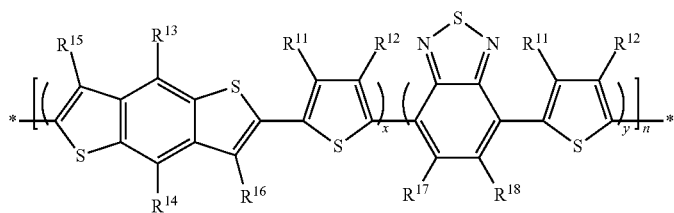 P1
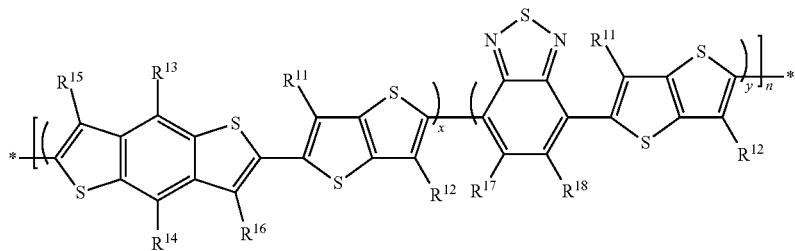 P2
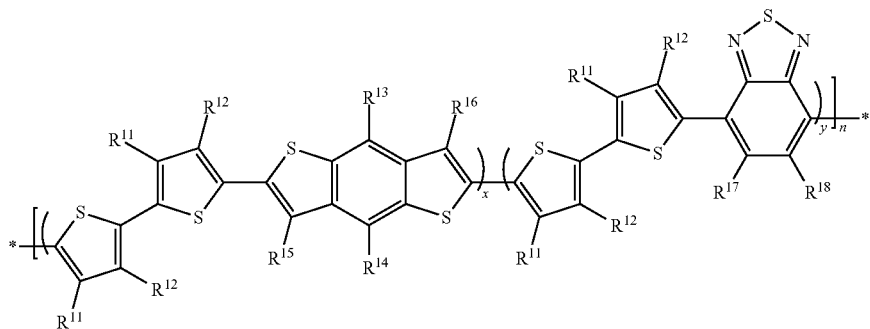 P3
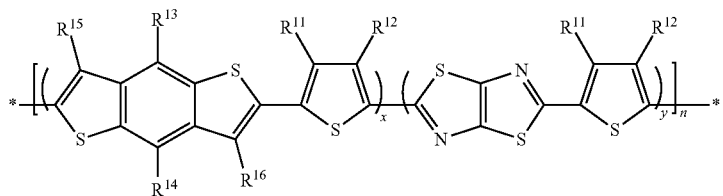 P4
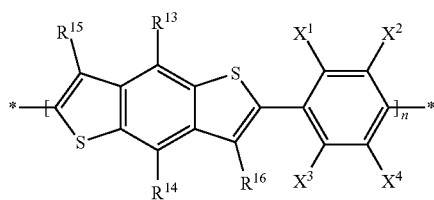 P5
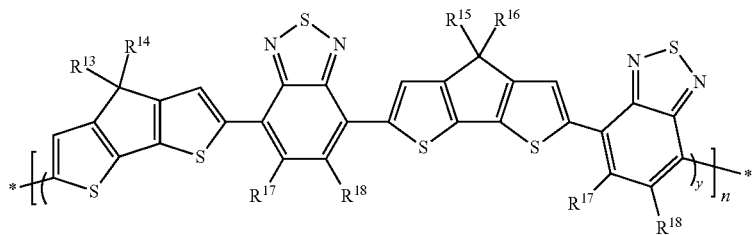 P6

-continued
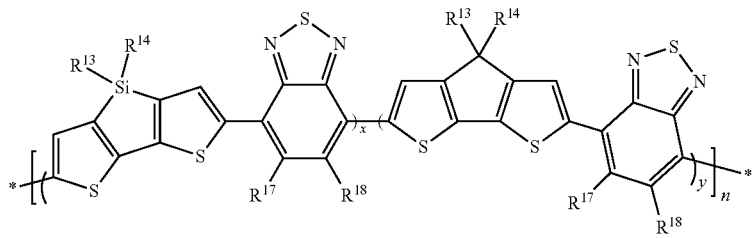
P7
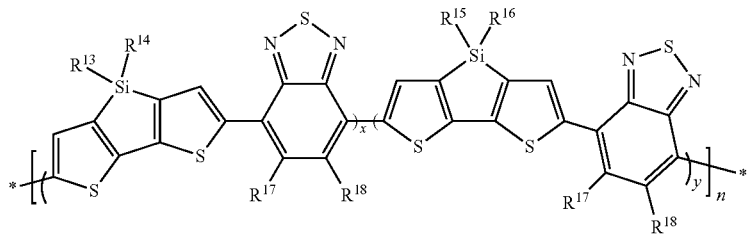
P8
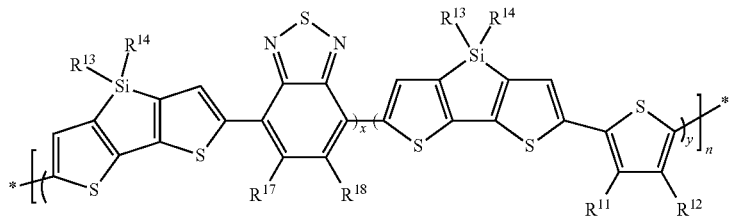
P9
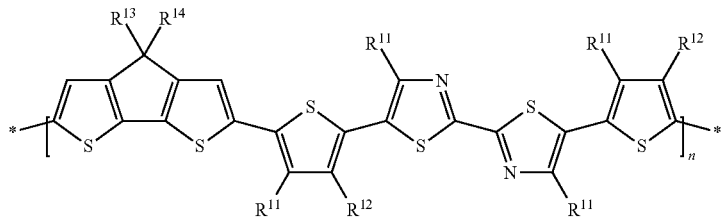
P10
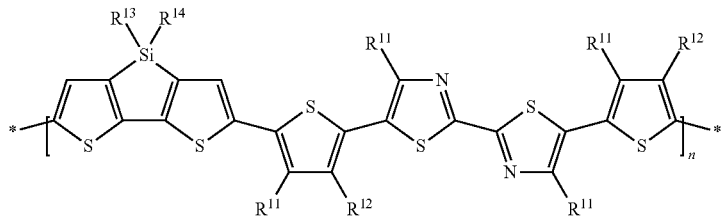
P11
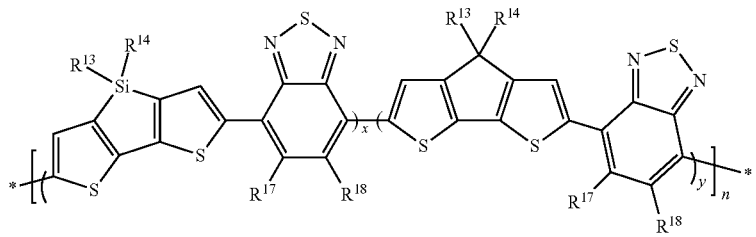
P12

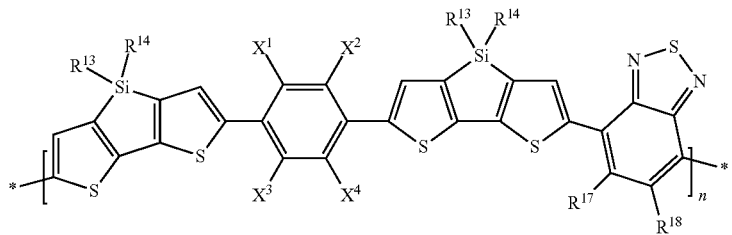 P13
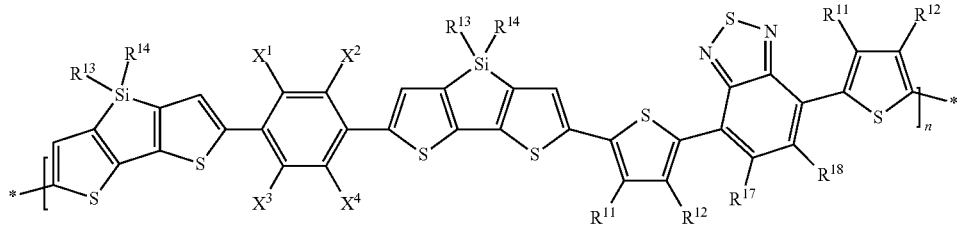 P14
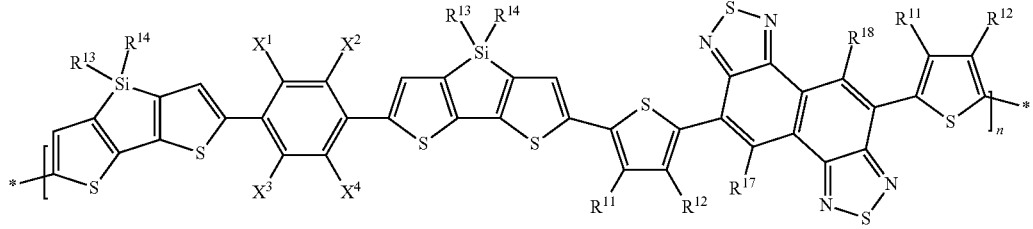 P15
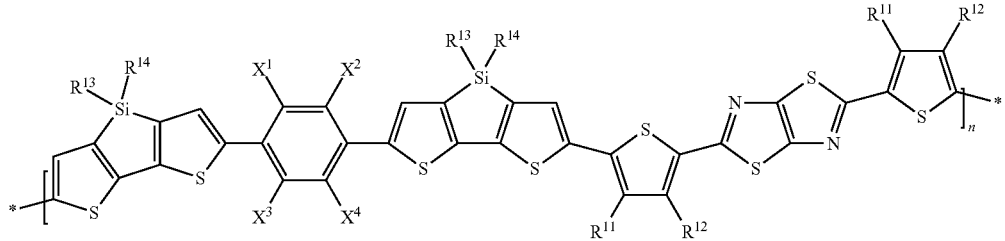 P16
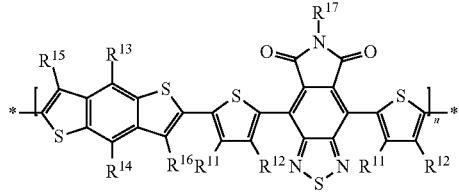 P18
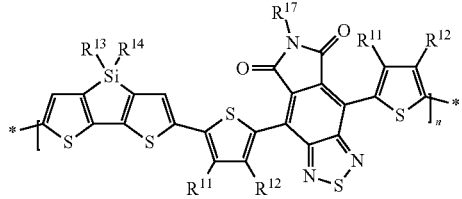 P17
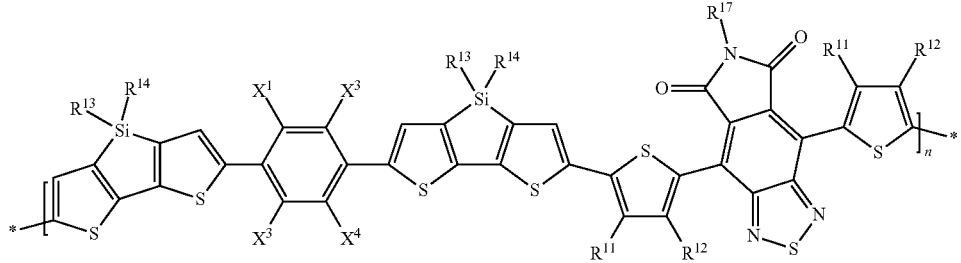 P19

-continued
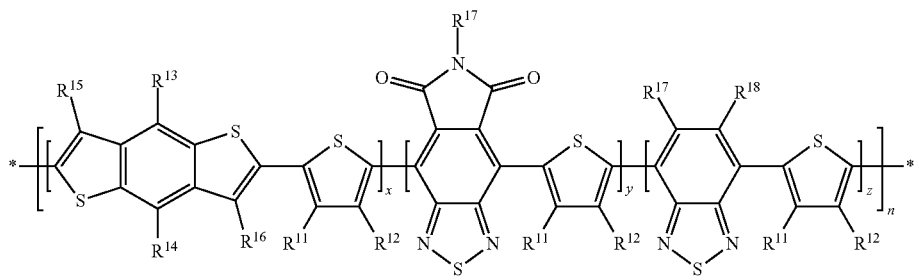
P20
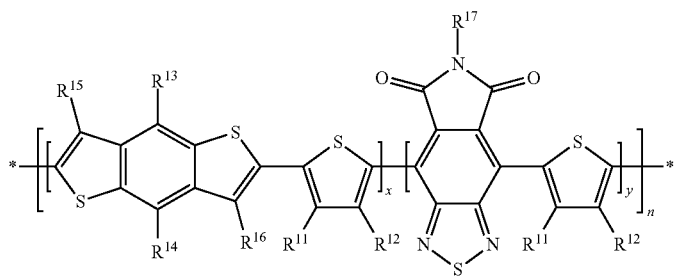
P21
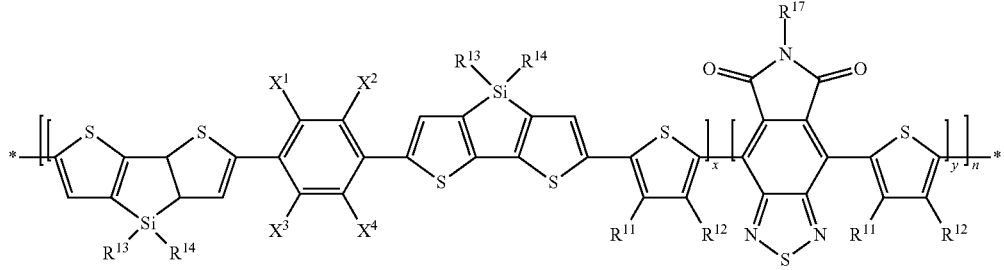
P22
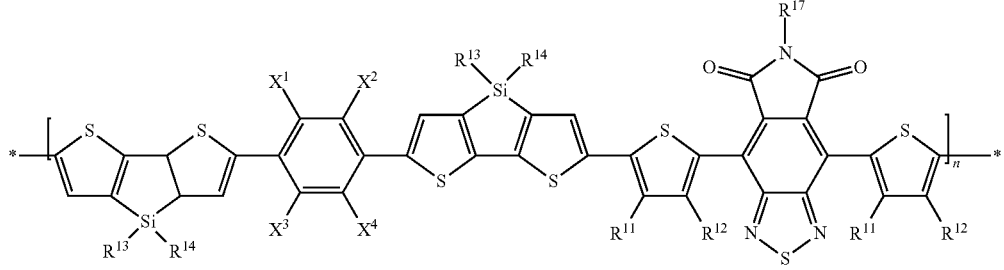
P23
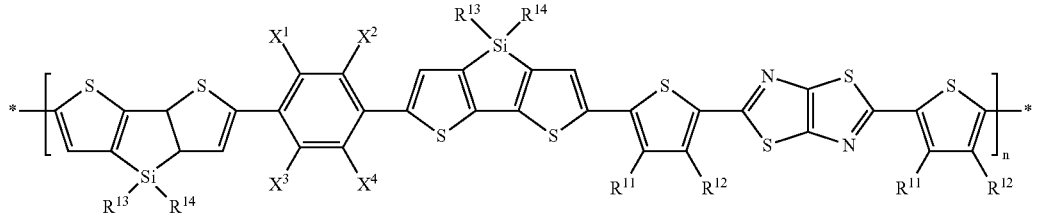
P24
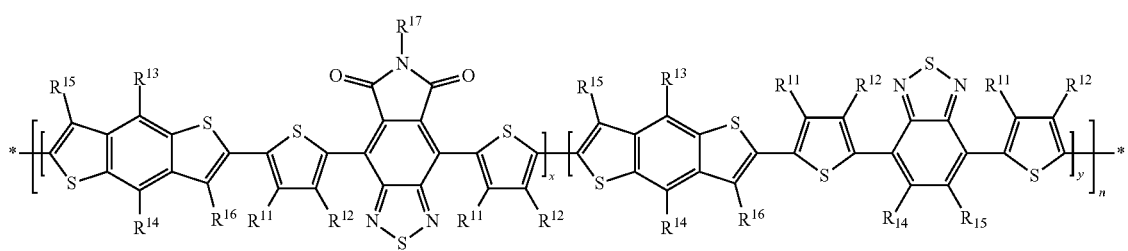
P25

-continued
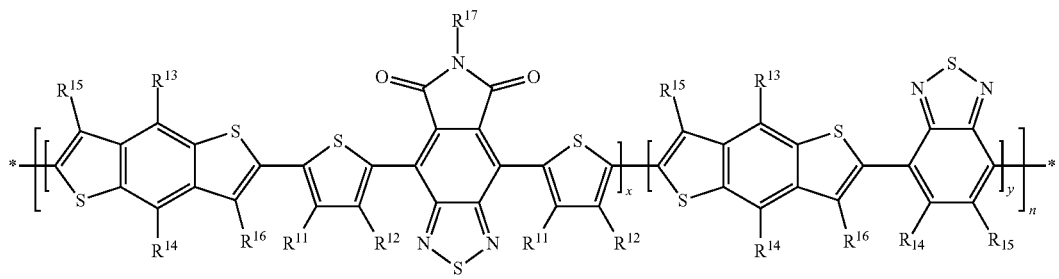
P26
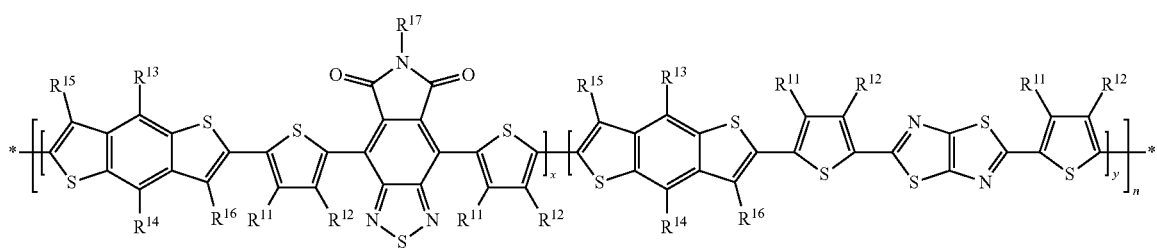
P27
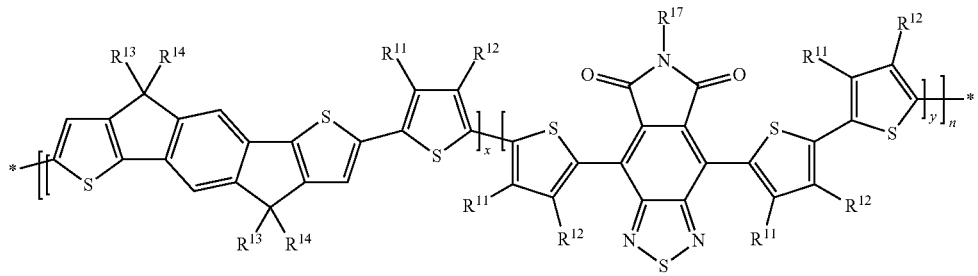
P28
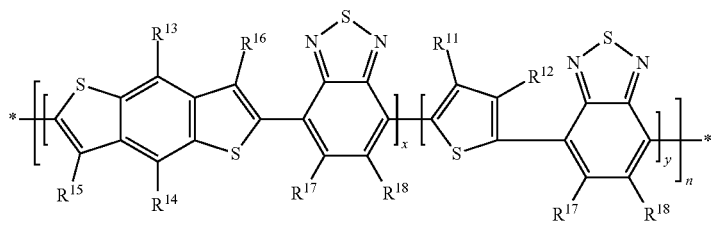
P29
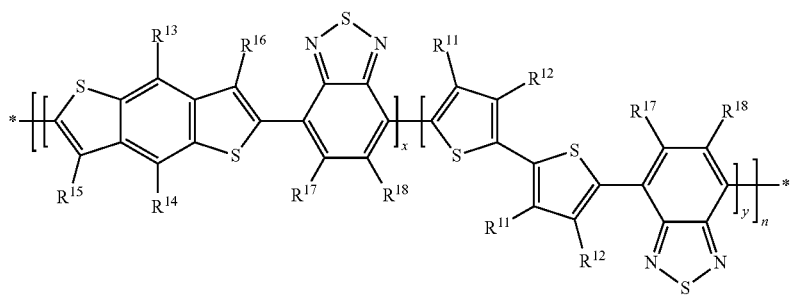
P30

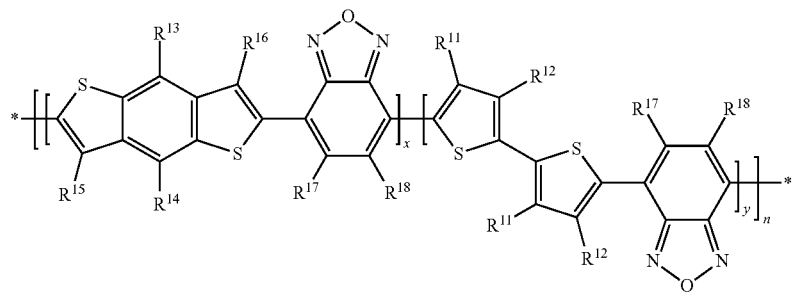
P31
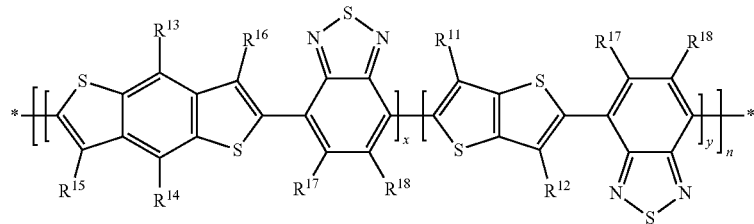
P32
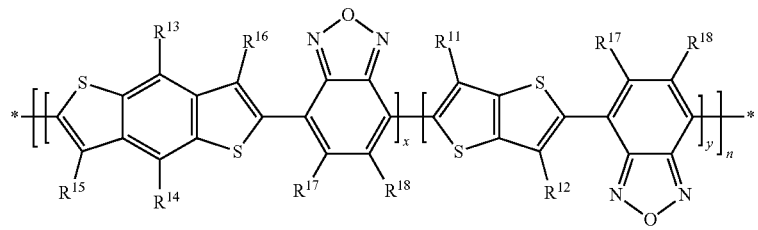
P33
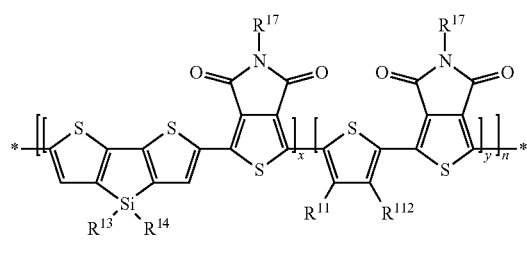
P34
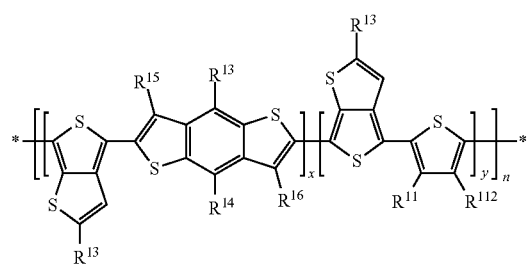
P35
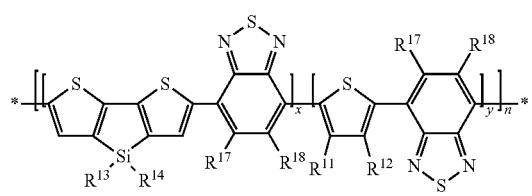
P36
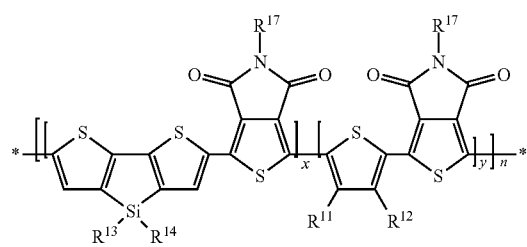
P37

-continued
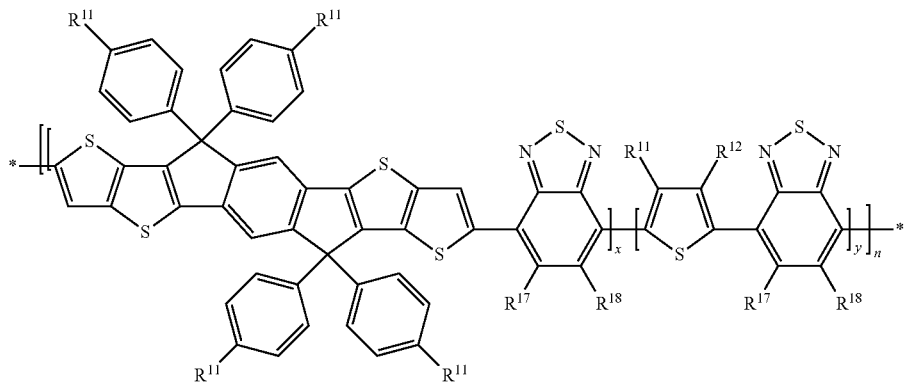
P38
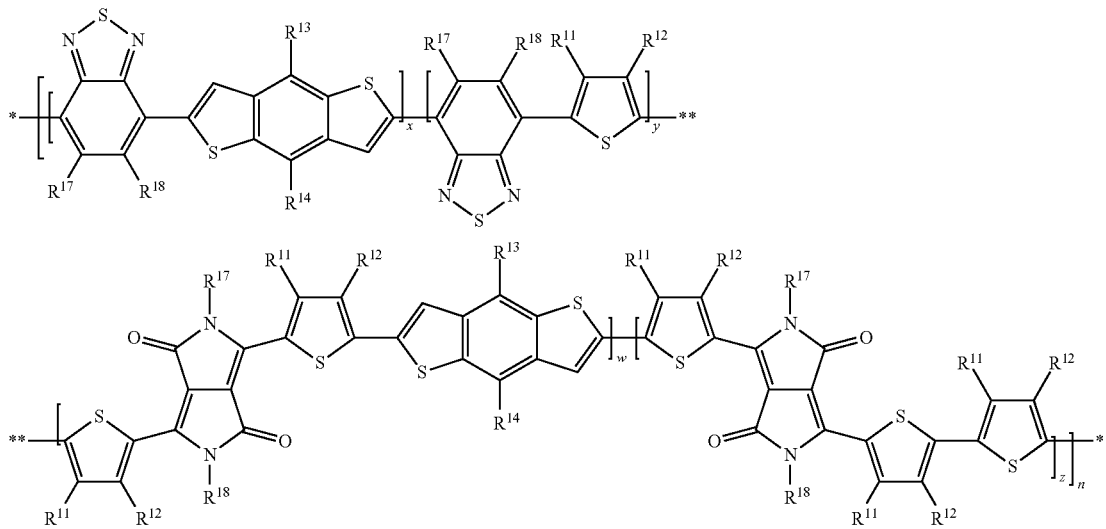
P39
P40
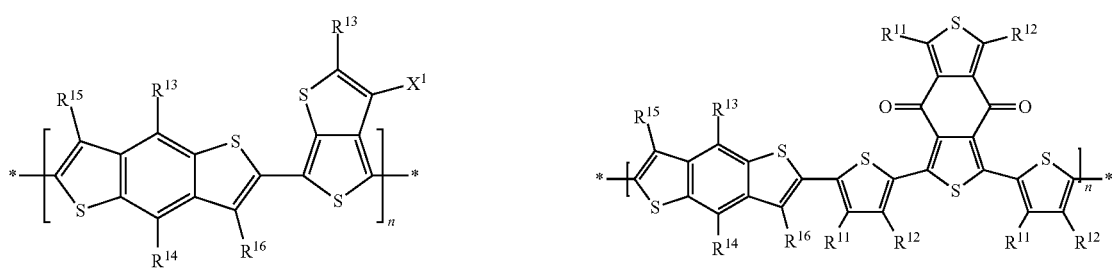
P41 P42
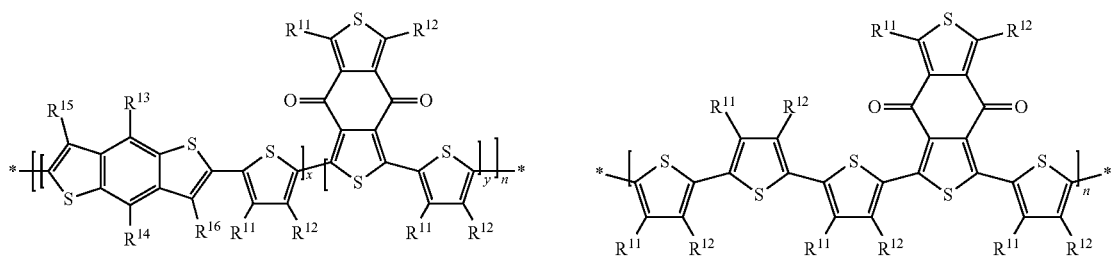
P43

-continued
P44
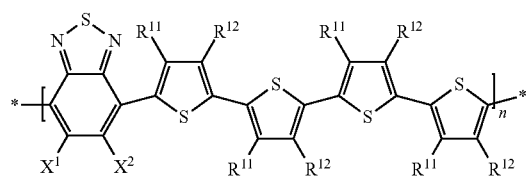
P45
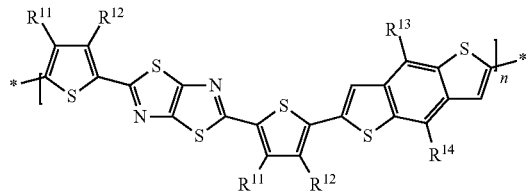
P46
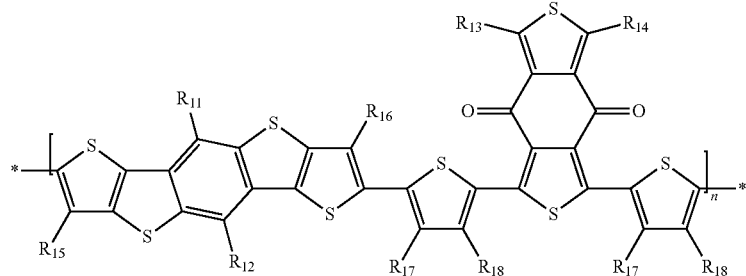
P47
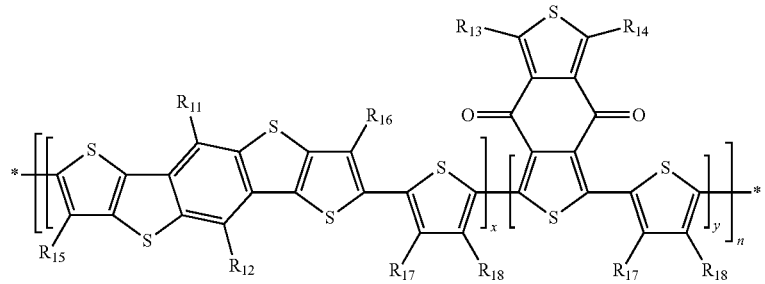
P48
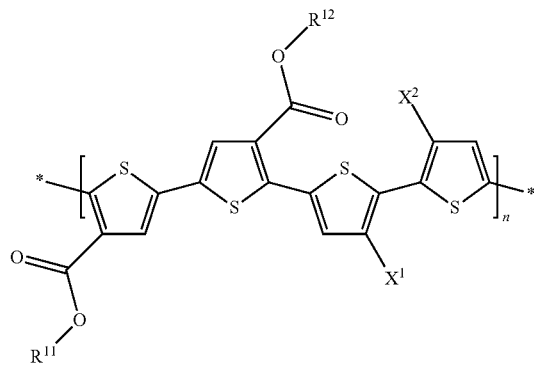
P49
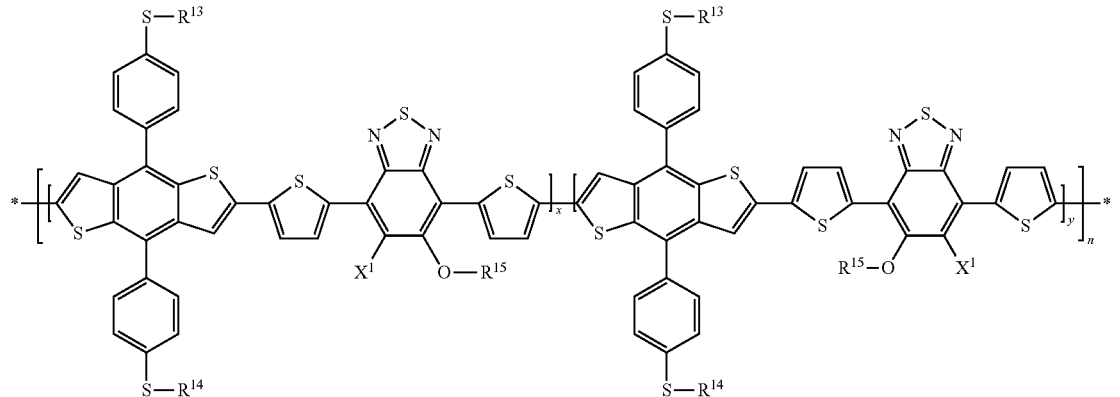

wherein $R^{11-17}$, x, y and n are as defined above, w and z have one of the meanings given for y, x+y+w+z=1, $R^{18}$ and $R^{19}$ have one of the meanings given for $R^{11}$, and $X^1$, $X^2$, $X^3$ and $X^4$ denote H, F or Cl.

In the formulae P1-P49 preferably one or more of $X^1$, $X^2$, $X^3$ and $X^4$ denote F, very preferably all of $X^1$, $X^2$, $X^3$ and $X^4$ denote F or $X^1$ and $X^2$ denote H and $X^3$ and $X^4$ denote F.

In the formulae P1-P49, preferably $R^{11}$ and $R^{12}$ are H. Further preferably $R^{11}$ and $R^{12}$, when being different from H, denote straight-chain or branched alkyl with 1 to 40, preferably 1 to 20, C atoms that is optionally fluorinated.

In the formulae P1-P49, preferably $R^{15}$ and $R^{16}$ are H, and $R^{13}$ and $R^{14}$ are different from H.

In the formulae P1-P49, preferably $R^{13}$, $R^{14}$, $R^{15}$ and $R^{16}$, when being different from H, are selected from the following groups:

the group consisting of straight-chain or branched alkyl, alkoxy or sulfanylalkyl with 1 to 40, preferably 1 to 20, C atoms that is optionally fluorinated, the group consisting of straight-chain or branched alkylcarbonyl or alkylcarbonyloxy with 2 to 40, preferably 2 to 20, C atoms, that is optionally fluorinated.

In the formulae P1-P49, preferably $R^{17}$ and $R^{18}$, when being different from H, are selected from the following groups:

the group consisting of straight-chain or branched alkyl, alkoxy or sulfanylalkyl with 1 to 40, preferably 1 to 20, C atoms that is optionally fluorinated, the group consisting of straight-chain or branched alkylcarbonyl or alkylcarbonyloxy with 2 to 40, preferably 2 to 20, C atoms, that is optionally fluorinated.

the group consisting of F and Cl.

Further preferred are conjugated polymers selected of formula PT $$R^{31}\text{-chain-}R^{32} \quad\quad PT$$

wherein "chain" denotes a polymer chain selected of formula Pi, Pii or P1-P49, and $R^{31}$ and $R^{32}$ have independently of each other one of the meanings of $R^{11}$ as defined above, or denote, independently of each other, H, F, Br, Cl, I, —CH$_2$Cl, —CHO, —CR'=CR"$_2$, —SiR'R"R'", —SiR'X'X", —SiR'R"X', —SnR'R"R'", —BR'R", —B(OR')(OR"), —B(OH)$_2$, —O—SO$_2$—R', —C≡CH, —C≡C—SiR'$_3$, —ZnX' or an endcap group, X' and X" denote halogen, R', R" and R'" have independently of each other one of the meanings of $R^0$ given in formula I, and preferably denote alkyl with 1 to 16 C atoms, and two of R', R" and R'" may also form a cyclosilyl, cyclostannyl, cycloborane or cycloboronate group with 2 to 20 C atoms together with the respective hetero atom to which they are attached.

Preferred endcap groups $R^{31}$ and $R^{32}$ are H, $C_{1-20}$ alkyl, or optionally substituted $C_{6-12}$ aryl or $C_{2-10}$ heteroaryl, very preferably H, phenyl or thiophene.

The compounds of formula I and the conjugated polymers of formula P and PT can be synthesized according to or in analogy to methods that are known to the skilled person and are described in the literature. Other methods of preparation can be taken from the examples.

For example, the compounds of the present invention can be suitably prepared by aryl-aryl coupling reactions, such as Yamamoto coupling, Suzuki coupling, Stille coupling, Sonogashira coupling, Heck coupling or Buchwald coupling. The educts can be prepared according to methods which are known to the person skilled in the art.

Preferred aryl-aryl coupling methods used in the synthesis methods as described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in *J. Chem. Soc., Chem. Commun.*, 1977, 683-684. Yamamoto coupling is described in for example in T. Yamamoto et al., *Prog. Polym. Sci.*, 1993, 17, 1153-1205, or WO 2004/022626 A1. Stille coupling is described for example in Z. Bao et al., *J. Am. Chem. Soc.*, 1995, 117, 12426-12435 and C—H activation is described for example in M. Leclerc et al, *Angew. Chem. Int. Ed.*, 2012, 51, 2068-2071. For example, when using Yamamoto coupling, educts having two reactive halide groups are preferably used. When using Suzuki coupling, educts having two reactive boronic acid or boronic acid ester groups or two reactive halide groups are preferably used. When using Stille coupling, educts having two reactive stannane groups or two reactive halide groups are preferably used. When using Negishi coupling, educts having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol$_3$P)$_4$. Preferred Pd(II) salts include palladium acetate, i.e. Pd(OAc)$_2$. Alternatively the Pd(0) complex can be prepared by mixing a Pd(0) dibenzylideneacetone complex, for example tris(dibenzyl-ideneacetone)dipalladium(0), bis(dibenzylideneacetone)palladium(0), or Pd(II) salts e.g. palladium acetate, with a phosphine ligand, for example triphenylphosphine, tris(ortho-tolyl)phosphine or tri(tert-butyl)phosphine. Suzuki coupling is performed in the presence of a base, for example sodium carbonate, potassium carbonate, cesium carbonate, lithium hydroxide, potassium phosphate or an organic base such as tetraethylammonium carbonate or tetraethylammonium hydroxide. Yamamoto coupling employs a Ni(0) complex, for example bis(1,5-cyclooctadienyl) nickel(0).

As alternatives to halogens as described above, leaving groups of formula —O—SO$_2$Z$^0$ can be used wherein Z$^0$ is an alkyl or aryl group, preferably $C_{1-10}$ alkyl or $C_{6-12}$ aryl. Particular examples of such leaving groups are tosylate, mesylate and triflate.

The compounds of formula I and its subformulae can be synthesized by methods that are known to the person skilled in the art and described in the literature, for example by the methods as illustrated in the synthesis schemes below or in analogy thereto. An especially suitable and preferred synthesis method is exemplarily shown in Scheme 1, wherein $R^{1-4}$ and $Ar^{1-3}$ are as defined in formula I and $A^{1-3}$ denote the corresponding non-quinoidal form of $Ar^{1-3}$.

Scheme 1

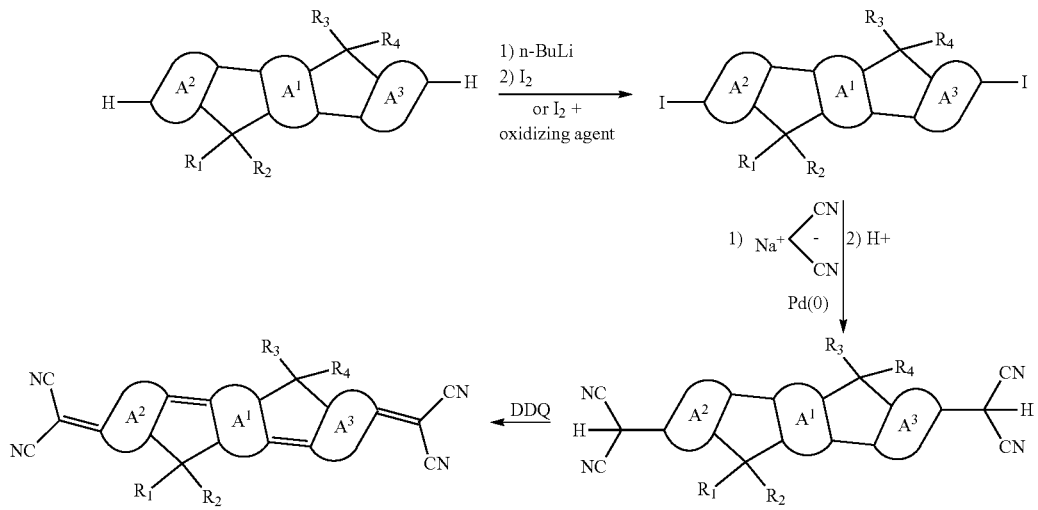

Novel methods of preparing compounds of formula I as described above and below are another aspect of the invention.

The compounds of formula I can also be used in compositions, for example together with monomeric or polymeric compounds having charge-transport, semiconducting, electrically conducting, photoconducting and/or light emitting semiconducting properties, or for example with compounds having hole blocking or electron blocking properties for use as interlayers or charge blocking layers in PSCs or OLEDs.

Thus, another aspect of the invention relates to a composition comprising one or more compounds of formula I and one or more small molecule compounds and/or polymers having one or more of a charge-transport, semiconducting, electrically conducting, photoconducting, hole blocking and electron blocking property.

These compositions blends can be prepared by conventional methods that are described in prior art and known to the skilled person. Typically the compounds and/or polymers are mixed with each other or dissolved in suitable solvents and the solutions combined.

Another aspect of the invention relates to a formulation comprising one or more compounds of formula I or compositions as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, chlorobenzene, o-dichlorobenzene, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetraline, 2-methylthiophene, 3-methylthiophene, decaline, indane, methyl benzoate, ethyl benzoate, mesitylene and/or mixtures thereof.

The concentration of the compounds or polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38 (496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The compounds of formula I can also be used in patterned OSC layers in the devices as described above and below. For applications in modern microelectronics it is generally desirable to generate small structures or patterns to reduce cost (more devices/unit area), and power consumption. Patterning of thin layers comprising a compound according to the present invention can be carried out for example by photolithography, electron beam lithography or laser patterning.

For use as thin layers in electronic or electrooptical devices the compounds, compositions or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound of formula I by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent(s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 m Pa·s.

The compositions and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The compounds according to the present invention are useful as charge transport, semiconducting, electrically conducting, photoconducting or light emitting materials in optical, electrooptical, electronic, electroluminescent or photoluminescent components or devices. In these devices, the compounds of the present invention are typically applied as thin layers or films.

Thus, the present invention also provides the use of the semiconducting compound or composition or layer in an electronic device. The compound or composition may be used as a high mobility semiconducting material in various devices and apparatus. The compound or composition may be used, for example, in the form of a semiconducting layer or film. Accordingly, in another aspect, the present invention provides a semiconducting layer for use in an electronic device, the layer comprising a compound or composition according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising compound or composition or organic semiconducting layer according to the present invention. Especially preferred devices are OFETs, TFTs, ICs, logic circuits, capacitors, RFID tags, OLEDs, OLETs, OPEDs, OPVs, PSCs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV, PSC and OPD devices, in particular PSC, OPD and bulk heterojunction (BHJ) OPV devices. In an OFET, for example, the active semiconductor channel between the drain and source may comprise the compound or composition of the invention. As another example, in an OLED device, the charge (hole or electron) injection or transport layer may comprise the compound or composition of the invention.

For use in the photoactive layer of OPV or OPD devices the compounds according to the present invention are preferably used in a composition that comprises or contains, more preferably consists of, one or more p-type (electron donor) semiconductors and one or more n-type (electron acceptor) semiconductors.

The n-type semiconductor is for example constituted by a compound of formula I.

The p-type semiconductor is preferably a conjugated polymer as defined above.

The composition can also comprise a compound of formula I as n-type semiconductor, a p-type semiconductor like a conjugated polymer, and a second n-type semiconductor, which is preferably a fullerene or substituted fullerene.

The fullerene is for example an indene-$C_{60}$-fullerene bisadduct like ICBA, or a (6,6)-phenyl-butyric acid methyl ester derivatized methano $C_{60}$ fullerene, also known as "PCBM-$C_{60}$" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g. a $C_{61}$ fullerene group, a $C_{70}$ fullerene group, or a $C_{71}$ fullerene group, or an organic polymer (see for example Coakley, K. M. and McGehee, M. D. Chem. Mater. 2004, 16, 4533).

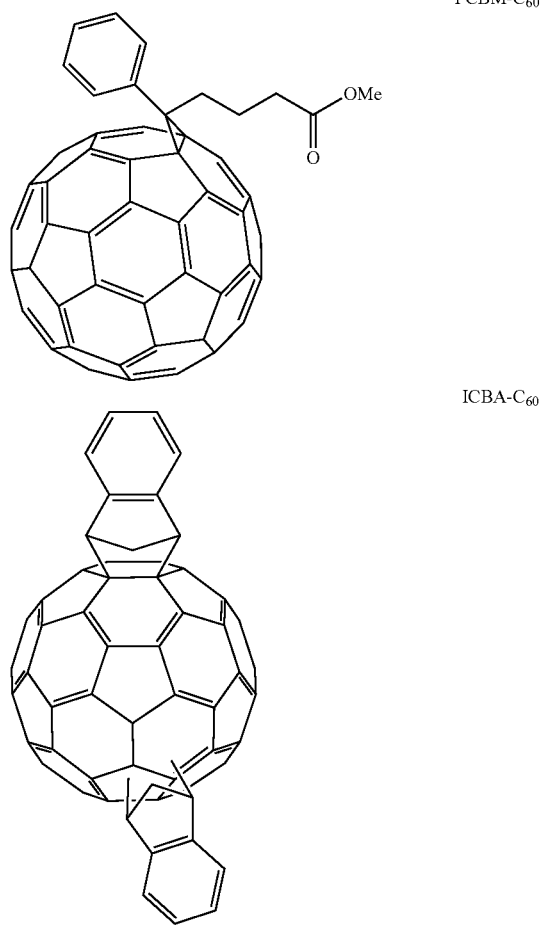

PCBM-$C_{60}$

ICBA-$C_{60}$

Preferably the fullerene is PCBM-C60, PCBM-C70, bis-PCBM-C60, bis-PCBM-070, ICMA-c60 (1',4'-dihydro-naphtho[2',3':1,2][5,6]fullerene-C60), ICBA, oQDM-C60 (1',4'-dihydro-naphtho[2',3':1,9][5,6]fullerene-C60-lh), or bis-oQDM-060.

The OPV or OPD device preferably further comprises a first transparent or semi-transparent electrode on a transparent or semi-transparent substrate on one side of the photoactive layer, and a second metallic or semi-transparent electrode on the other side of the photoactive layer.

Further preferably the OPV or OPD device comprises, between the photoactive layer and the first or second electrode, one or more additional buffer layers acting as hole transporting layer and/or electron blocking layer, which comprise a material such as metal oxide, like for example, ZTO, $MoO_x$, $NiO_x$, a conjugated polymer electrolyte, like for example PEDOT:PSS, a conjugated polymer, like for example polytriarylamine (PTAA), an insulating polymer, like for example nafion, polyethyleneimine or polystyrene-sulphonate, an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, $ZnO_x$, $TiO_x$, a salt, like for example LiF, NaF, CsF, a conjugated polymer electrolyte, like for example poly[3-(6-trimethylammoniumhexyl)thiophene], poly(9,9-bis(2-ethylhexyl)-fluorene]-b-poly[3-(6-trimethylammoniumhexyl)thiophene], or poly[(9,9-bis(3'-(N,N-dimethylamino)propyl)-2,7-fluorene)-alt-2,7-(9,9-dioctylfluorene)] or an organic compound, like for example tris(8-quinolinolato)-aluminium(III) ($Alq_3$), 4,7-diphenyl-1,10-phenanthroline.

In a composition according to the present invention comprising a compound of formula I and a conjugated polymer, the ratio polymer:compound of formula I is preferably from 5:1 to 1:5 by weight, more preferably from 1:1 to 1:3 by weight, most preferably 1:1 to 1:2 by weight.

The composition according to the present invention may also comprise a polymeric binder, preferably from 5 to 95% by weight. Examples of binder include polystyrene (PS), polydimethylsilane (PDMS), polypropylene (PP) and polymethylmethacrylate (PMMA).

A binder to be used in the formulation as described before, which is preferably a polymer, may comprise either an insulating binder or a semiconducting binder, or mixtures thereof, may be referred to herein as the organic binder, the polymeric binder or simply the binder.

Preferably, the polymeric binder comprises a weight average molecular weight in the range of 1000 to 5,000,000 g/mol, especially 1500 to 1,000,000 g/mol and more preferable 2000 to 500,000 g/mol. Surprising effects can be achieved with polymers having a weight average molecular weight of at least 10000 g/mol, more preferably at least 100000 g/mol.

In particular, the polymer can have a polydispersity index $M_w/M_n$ in the range of 1.0 to 10.0, more preferably in the range of 1.1 to 5.0 and most preferably in the range of 1.2 to 3.

Preferably, the inert binder is a polymer having a glass transition temperature in the range of −70 to 160° C., preferably 0 to 150° C., more preferably 50 to 140° C. and most preferably 70 to 130° C. The glass transition temperature can be determined by measuring the DSC of the polymer (DIN EN ISO 11357, heating rate 10° C. per minute).

The weight ratio of the polymeric binder to the OSC compound, like that of formula I, is preferably in the range of 30:1 to 1:30, particularly in the range of 5:1 to 1:20 and more preferably in the range of 1:2 to 1:10.

According to a preferred embodiment the binder preferably comprises repeating units derived from styrene monomers and/or olefin monomers. Preferred polymeric binders can comprise at least 80%, preferably 90% and more preferably 99% by weight of repeating units derived from styrene monomers and/or olefins.

Styrene monomers are well known in the art. These monomers include styrene, substituted styrenes with an alkyl substituent in the side chain, such as a-methylstyrene and α-ethylstyrene, substituted styrenes with an alkyl substituent on the ring such as vinyltoluene and p-methylstyrene, halogenated styrenes such as monochlorostyrenes, dichlorostyrenes, tribromostyrenes and tetrabromostyrenes.

Olefin monomers consist of hydrogen and carbon atoms. These monomers include ethylene, propylene, butylenes, isoprene and 1,3-butadiene.

According to a preferred embodiment of the present invention, the polymeric binder is polystyrene having a weight average molecular weight in the range of 50,000 to 2,000,000 g/mol, preferably 100,000 to 750,000 g/mol, more preferably in the range of 150,000 to 600,000 g/mol and most preferably in the range of 200,000 to 500,000 g/mol.

Further examples of suitable binders are disclosed for example in US 2007/0102696 A1. Especially suitable and preferred binders are described in the following.

The binder should preferably be capable of forming a film, more preferably a flexible film.

Suitable polymers as binders include poly(1,3-butadiene), polyphenylene, polystyrene, poly(α-methylstyrene), poly (α-vinylnaphtalene), poly(vinyltoluene), polyethylene, cis-polybutadiene, polypropylene, polyisoprene, poly(4-methyl-1-pentene), poly (4-methylstyrene), poly (chorotrifluoroethylene), poly(2-methyl-1,3-butadiene), poly(p-xylylene), poly(α-α-α'-α' tetrafluoro-p-xylylene), poly[1,1-(2-methyl propane)bis(4-phenyl)carbonate], poly (cyclohexyl methacrylate), poly(chlorostyrene), poly(2,6-dimethyl-1,4-phenylene ether), polyisobutylene, poly(vinyl cyclohexane), poly(vinylcinnamate), poly(4-vinylbiphenyl), 1,4-polyisoprene, polynorbornene, poly(styrene-block-butadiene); 31% wt styrene, poly(styrene-block-butadiene-block-styrene); 30% wt styrene, poly(styrene-co-maleic anhydride) (and ethylene/butylene) 1-1.7% maleic anhydride, poly(styrene-block-ethylene/butylene-block-styrene) triblock polymer 13% styrene, poly(styrene-block-ethylene-propylene-block-styrene) triblock polymer 37% wt styrene, poly(styrene-block-ethylene/butylene-block-styrene) triblock polymer 29% wt styrene, poly(l-vinylnaphtalene), poly(l-vinyl pyrrolidone-co-styrene) 64% styrene, poly(l-vinylpyrrolidone-co-vinyl acetate) 1.3:1, poly(2-chlorostyrene), poly(2-vinylnaphtalene), poly(2-vinylpyridine-co-styrene) 1:1, poly(4,5-Difluoro-2,2-bis(CF3)-1,3-dioxole-co-tetrafluoroethylene) Teflon, poly(4-chlorostyrene), poly (4-methyl-1-pentene), poly(4-methylstyrene), poly(4-vinylpyridine-co-styrene) 1:1, poly(alpha-methylstyrene), poly(butadiene-graft-poly(methyl acrylate-co-acrylonitrile)) 1:1:1, poly(butyl methacrylate-co-isobutyl methacrylate) 1:1, poly(butyl methacrylate-co-methyl methacrylate) 1:1, poly(cyclohexylmethacrylate), poly(ethylene-co-1-butene-co-1-hexene) 1:1:1, poly(ethylene-co-ethylacrylate-co-maleic anhydride); 2% anhydride, 32% ethyl acrylate, poly (ethylene-co-glycidyl methacrylate) 8% glycidyl methacrylate, poly(ethylene-co-methyl acrylate-co-glycidyl meth-acrylate) 8% glycidyl metha-crylate 25% methyl acrylate, poly(ethylene-co-octene) 1:1, poly(ethylene-co-propylene-co-5-methylene-2-norbornene) 50% ethylene, poly(ethylene-co-tetrafluoroethylene) 1:1, poly(isobutyl methacrylate), poly(isobutylene), poly(methyl methacrylate)-co-(fluorescein O-methacrylate) 80% methyl methacrylate, poly(methyl methacrylate-co-butyl methacrylate) 85% methyl methacrylate, poly(methyl methacrylate-co-ethyl acrylate) 5% ethyl acrylate, poly(propylene-co-butene) 12% 1-butene, poly(styrene-co-allyl alcohol) 40% allyl alcohol, poly(styrene-co-maleic anhydride) 7% maleic anhydride, poly(styrene-co-maleic anhydride) cumene terminated (1.3:1), poly(styrene-co-methyl methacrylate) 40% styrene, poly(vinyltoluene-co-alpha-methylstyrene) 1:1, poly-2-vinylpyridine, poly-4-vinylpyridine, poly-alpha-pinene, polymethylmethacrylate, polybenzylmethacrylate, polyethylmethacrylate, polyethylene, polyethylene terephthalate, polyethylene-co-ethylacrylate 18% ethyl acrylate, polyethylene-co-vinylacetate 12% vinyl acetate, polyethylene-graft-maleic anhydride 0.5% maleic anhydride, polypropylene, polypropylene-graft-maleic anhydride 8-10% maleic anhydride, polystyrene poly(styrene-block-ethylene/butylene-block-styrene) graft maleic anhydride 2% maleic anhydride 1:1:1 others, poly(styrene-block-butadiene) branched 1:1, poly(styrene-block-butadiene-block-styrene), 30% styrene, poly(styrene-block-isoprene) 10% wt styrene, poly(styrene-block-isoprene-block-styrene) 17% wt styrene, poly(styrene-co-4-chloromethylstyrene-co-4-methoxymethylstyrene 2:1:1, polystyrene-co-acrylonitrile 25% acrylonitrile, polystyrene-co-alpha-methylstyrene 1:1, polystyrene-co-butadiene 4% butadiene, polystyrene-co-butadiene 45% styrene, polystyrene-co-chloromethylstyrene 1:1, polyvinylchloride, polyvinylcinnamate, polyvinylcyclohexane, polyvinylidenefluoride, polyvinylidenefluoride-co-hexafluoropropylene assume 1:1, poly(styrene-block-ethylene/propylene-block-styrene) 30% styrene, poly(styrene-block-ethylene/propylene-block-styrene) 18% styrene, poly (styrene-block-ethylene/propylene-block-styrene) 13% styrene, poly(styrene-block ethylene block-ethylene/propylene-block styrene) 32% styrene, poly(styrene-block ethylene block-ethylene/propylene-block styrene) 30% styrene, poly(styrene-block-ethylene/butylene-block-styrene) 31% styrene, poly(styrene-block-ethylene/butylene-block-styrene) 34% styrene, poly(styrene-block-ethylene/butylene-block-styrene) 30% styrene, poly(styrene-block-ethylene/butylene-block-styrene) 60%, styrene, branched or non-branched polystyrene-block-polybutadiene, polystyrene-block(polyethylene-ran-butylene)-block-polystyrene, polystyrene-block-polybutadiene-block-polystyrene, polystyrene-(ethylene-propylene)-diblock-copolymers (e.g. KRATON®-G1701E, Shell), poly(propylene-co-ethylene) and poly(styrene-co-methylmethacrylate).

Preferred insulating binders to be used in the formulations as described before are polystryrene, poly(α-methylstyrene), polyvinylcinnamate, poly(4-vinylbiphenyl), poly(4-methylstyrene), and polymethyl methacrylate. Most preferred insulating binders are polystyrene and polymethyl methacrylate.

The binder can also be selected from crosslinkable binders, like e.g. acrylates, epoxies, vinylethers, thiolenes etc. The binder can also be mesogenic or liquid crystalline.

The organic binder may itself be a semiconductor, in which case it will be referred to herein as a semiconducting binder. The semiconducting binder is still preferably a binder of low permittivity as herein defined. Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility of at least $10^{-5}$ $cm^2V^{-1}s^{-1}$, more preferably at least $10^{-4}$ $cm^2V^{-1}s^{-1}$.

A preferred semiconducting binder comprises a homopolymer or copolymer (including block-copolymer) containing arylamine (preferably triarylamine).

To produce thin layers in BHJ OPV devices the compounds, compositions and formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letterpress printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the mixture of a compound of formula I and a polymer must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetraline, 2-methylthiophene, 3-methylthiophene, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
optionally a substrate,
a high work function electrode, preferably comprising a metal oxide, like for example ITO, serving as anode,
an optional conducting polymer layer or hole transport layer, preferably comprising an organic polymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
optionally a layer having electron transport properties, for example comprising LiF or PFN,
a low work function electrode, preferably comprising a metal like for example aluminium, serving as cathode,
wherein at least one of the electrodes, preferably the anode, is transparent to visible light, and
wherein the n-type semiconductor is a compound of formula I.

A second preferred OPV device according to the invention is an inverted OPV device and comprises the following layers (in the sequence from bottom to top):
optionally a substrate,
a high work function metal or metal oxide electrode, comprising for example ITO, serving as cathode,
a layer having hole blocking properties, preferably comprising a metal oxide like $TiO_x$ or $Zn_x$, or a poly (ethyleneimine),
a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
an optional conducting polymer layer or hole transport layer, preferably comprising an organic polymer or polymer blend, for example of PEDOT:PSS, nafion or a substituted triaryl amine derivative like for example TBD or NBD,
an electrode comprising a high work function metal like for example silver, serving as anode,
wherein at least one of the electrodes, preferably the cathode, is transparent to visible light, and
wherein the n-type semiconductor is a compound of formula I.

In the OPV devices of the present invention the p-type and n-type semiconductor materials are preferably selected from the materials, like the compound/polymer/fullerene systems, as described above When the photoactive layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater*, 2004, 14(10), 1005. An optional annealing step may be then necessary to optimize blend morpohology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Fréchet et al. *J. Am. Chem. Soc.*, 2010, 132, 7595-7597.

Another preferred embodiment of the present invention relates to the use of a compound or composition according to the present invention as dye, hole transport layer, hole blocking layer, electron transport layer and/or electron blocking layer in a DSSC or a PSC, and to a DSSC or PSC comprising a compound or composition according to the present invention.

DSSCs and PSCs can be manufactured as described in the literature, for example in Chem. Rev. 2010, 110, 6595-6663, Angew. Chem. Int. Ed. 2014, 53, 2-15 or in WO2013171520A1

A preferred OE device according to the invention is a solar cell, preferably a PSC, comprising the light absorber which is at least in part inorganic as described below.

In a solar cell comprising the light absorber according to the invention there are no restrictions per se with respect to the choice of the light absorber material which is at least in part inorganic.

The term "at least in part inorganic" means that the light absorber material may be selected from metalorganic complexes or materials which are substantially inorganic and possess preferably a crystalline structure where single positions in the crystalline structure may be allocated by organic ions.

Preferably, the light absorber comprised in the solar cell according to the invention has an optical band-gap ≤2.8 eV and ≥0.8 eV.

Very preferably, the light absorber in the solar cell according to the invention has an optical band-gap ≤2.2 eV and ≥1.0 eV.

The light absorber used in the solar cell according to the invention does preferably not contain a fullerene. The chemistry of fullerenes belongs to the field of organic chemistry. Therefore fullerenes do not fulfil the definition of being "at least in part inorganic" according to the invention.

Preferably, the light absorber which is at least in part inorganic is a material having perovskite structure or a material having 2D crystalline perovskite structure.

The term "perovskite" as used above and below denotes generally a material having a perovskite crystalline structure or a 2D crystalline perovskite structure.

The term perovskite solar cell (PSC) means a solar cell comprising a light absorber which is a material having perovskite structure or a material having 2D crystalline perovskite structure.

The light absorber which is at least in part inorganic is without limitation composed of a material having perovskite crystalline structure, a material having 2D crystalline perovskite structure (e.g. CrystEngComm, 2010,12, 2646-2662), $Sb_2S_3$ (stibnite), $Sb_2(S_xSe_{(x-1)})_3$, $PbS_xSe_{(x-1)}$, $CdS_xSe_{(x-1)}$, ZnTe, CdTe, $ZnS_xSe_{(x-1)}$, InP, FeS, $FeS_2$, $Fe_2S_3$, $Fe_2SiS_4$, $Fe_2GeS_4$, $Cu_2S$, CuInGa, $CuIn(Se_xS_{(1-x)})_2$, $Cu_3Sb_xBi_{(x-1)}$, $(S_ySe_{(y-1)})_3$, $Cu_2SnS_3$, $SnS_xSe_{(x-1)}$, $Ag_2S$, $AgBiS_2$, BiSI, BiSeI, $Bi_2(S_xSe_{(x-1)})_3$, $BiS_{(1-x)}Se_xI$, $WSe_2$, AlSb, metal halides (e.g. $BiI_3$, $Cs_2SnI_6$), chalcopyrite (e.g. $CuIn_xGa_{(1-x)}(S_ySe_{(1-y)})_2$), kesterite (e.g. $Cu_2ZnSnS_4$, $Cu_2ZnSn(Se_xS_{(1-x)})_4$, $Cu_2Zn(Sn_{1-x}Ge_x)S_4$) and metal oxide (e.g. CuO, $Cu_2O$) or a mixture thereof.

Preferably, the light absorber which is at least in part inorganic is a perovskite.

In the above definition for light absorber, x and y are each independently defined as follows: (0≤x≤1) and (0≤y≤1).

Very preferably, the light absorber is a special perovskite namely a metal halide perovskite as described in detail above and below. Most preferably, the light absorber is an organic-inorganic hybrid metal halide perovskite contained in the perovskite solar cell (PSC).

In one particularly preferred embodiment of the invention, the perovskite denotes a metal halide perovskite with the formula $ABX_3$,
where
A is a monovalent organic cation, a metal cation or a mixture of two or more of these cations
B is a divalent cation and
X is F, Cl, Br, I, $BF_4$ or a combination thereof.

Preferably, the monovalent organic cation of the perovskite is selected from alkylammonium, wherein the alkyl group is straight chain or branched having 1 to 6 C atoms, formamidinium or guanidinium or wherein the metal cation is selected from $K^+$, $Cs^+$ or $Rb^+$.

Suitable and preferred divalent cations B are $Ge^{2+}$, $Sn^{2+}$ or $Pb^{2+}$.

Suitable and preferred perovskite materials are $CsSnI_3$, $CH_3NH_3Pb(I_{1-x}Cl_x)_3$, $CH_3NH_3PbI_3$, $CH_3NH_3Pb(I_{1-x}Br_x)_3$, $CH_3NH_3Pb(I_{1-x}(BF_4)_x)_3$, $CH_3NH_3Sn(I_{1-x}Cl_x)_3$, $CH_3NH_3SnI_3$ or $CH_3NH_3Sn(I_{1-x}Br_x)_3$ wherein x is each independently defined as follows: (0<x≤1).

Further suitable and preferred perovskites may comprise two halides corresponding to formula $Xa_{(3-x)}Xb_{(x)}$, wherein Xa and Xb are each independently selected from Cl, Br, or I, and x is greater than 0 and less than 3.

Suitable and preferred perovskites are also disclosed in WO 2013/171517, claims 52 to 71 and claims 72 to 79, which is entirely incorporated herein by reference. The materials are defined as mixed-anion perovskites comprising two or more different anions selected from halide anions and chalcogenide anions. Preferred perovskites are disclosed on page 18, lines 5 to 17. As described, the perovskite is usually selected from $CH_3NH_3PbBrI_2$, $CH_3NH_3PbBrCl_2$, $CH_3NH_3PbIBr_2$, $CH_3NH_3PbICl_2$, $CH_3NH_3SnF_2Br$, $CH_3NH_3SnF_2I$ and $(H_2N=CH-NH_2)PbI_{3z}Br_{3(1-z)}$, wherein z is greater than 0 and less than 1.

The invention further relates to a solar cell comprising the light absorber, preferably a PSC, as described above and below, wherein the compound of formula I is employed as a layer between one electrode and the light absorber layer.

The invention further relates to a solar cell comprising the light absorber, preferably a PSC, as described above and below, wherein the compound of formula I is comprised in an electron-selective layer.

The electron selective layer is defined as a layer providing a high electron conductivity and a low hole conductivity favoring electron-charge transport.

The invention further relates to a solar cell comprising the light absorber, preferably a PSC, as described above and below, wherein the compound of formula I is employed as electron transport material (ETM) or as hole blocking material as part of the electron selective layer.

Preferably, the compound of formula I is employed as electron transport material (ETM).

In an alternative preferred embodiment, the compound of formula I is employed as hole blocking material.

The device architecture of a PSC device according to the invention can be of any type known from the literature.

A first preferred device architecture of a PSC device according to the invention comprises the following layers (in the sequence from bottom to top):

optionally a substrate which, in any combination, can be flexible or rigid and transparent, semi-transparent or non-transparent and electrically conductive or non-conductive;

a high work function electrode, preferably comprising a doped metal oxide, for example fluorine-doped tin oxide (FTO), tin-doped indium oxide (ITO), or aluminium-doped zinc oxide;

an electron-selective layer which comprises one or more electron-transporting materials, at least one of which is a compound of formula I, and which, in some cases, can also be a dense layer and/or be composed of nanoparticles, and which preferably comprises a metal oxide such as $TiO_2$, $ZnO_2$, $SnO_2$, $Y_2O_5$, $Ga_2O_3$, $SrTiO_3$, $BaTiO_3$ or combinations thereof;

optionally a porous scaffold which can be conducting, semi-conducting or insulating, and which preferably comprises a metal oxide such as $TiO_2$, $ZnO_2$, $SnO_2$, $Y_2O_5$, $Ga_2O_3$, $SrTiO_3$, $BaTiO_3$, $Al_2O_3$, $ZrO_2$, $SiO_2$ or combinations thereof, and which is preferably composed of nanoparticles, nanorods, nanoflakes, nanotubes or nanocolumns;

a layer comprising a light absorber which is at least in part inorganic, particularly preferably a metal halide perovskite as described above which, in some cases, can also be a dense or porous layer and which optionally partly or fully infiltrates into the underlying layer;

optionally a hole selective layer, which comprises one or more hole-transporting materials, and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris(bis(trifluoromethylsulfonyl)imide)), which can enhance the properties of the hole selective layer, for example the electrical conductivity, and/or facilitate its processing;

and a back electrode which can be metallic, for example made of Au, Ag, Al, Cu, Ca, Ni or combinations thereof, or non-metallic and transparent, semi-transparent or non-transparent.

A second preferred device architecture of a PSC device according to the invention comprises the following layers (in the sequence from bottom to top):

optionally a substrate which, in any combination, can be flexible or rigid and transparent, semi-transparent or non-transparent and electrically conductive or non-conductive;

a high work function electrode, preferably comprising a doped metal oxide, for example fluorine-doped tin oxide (FTO), tin-doped indium oxide (ITO), or aluminium-doped zinc oxide;

optionally a hole injection layer which, for example, changes the work function of the underlying electrode, and/or modifies the surface of the underlying layer and/or helps to planarize the rough surface of the underlying layer and which, in some cases, can also be a monolayer;

optionally a hole selective layer, which comprises one or more hole-transporting materials and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris(bis(trifluoromethylsulfonyl)imide)), which can enhance the properties of the hole selective layer, for example the electrical conductivity, and/or facilitate its processing;

a layer comprising a light absorber which is at least in part inorganic, particularly preferably a metal halide perovskite as described or preferably described above;

an electron-selective layer, which comprises one or more electron-transporting materials, at least one of which is a compound of formula I and which, in some cases, can also be a dense layer and/or be composed of nanoparticles, and which, for example, can comprise a metal oxide such as $TiO_2$, $ZnO_2$, $SnO_2$, $Y_2O_5$, $Ga_2O_3$, $SrTiO_3$, $BaTiO_3$ or combinations thereof, and/or which can comprise a substituted fullerene, for example [6,6]-phenyl C61-butyric acid methyl ester, and/or which can comprise a molecular, oligomeric or polymeric electron-transport material, for example 2,9-Dimethyl-4,7-diphenyl-1,10-phenanthroline, or a mixture thereof;

and a back electrode which can be metallic, for example made of Au, Ag, Al, Cu, Ca, Ni or combinations thereof, or non-metallic and transparent, semi-transparent or non-transparent.

To produce electron selective layers in PSC devices according to the invention, the compounds of formula I, optionally together with other compounds or additives in the form of blends or mixtures, may be deposited by any suitable method. Liquid coating of devices is more desirable than vacuum deposition techniques. Solution deposition methods are especially preferred. Formulations comprising the compounds of formula I enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot die coating or pad printing. For the fabrication of PSC devices and modules, deposition techniques for large area coating are preferred, for example slot die coating or spray coating.

Formulations that can be used to produce electron selective layers in optoelectronic devices according to the invention, preferably in PSC devices comprise one or more compounds of formula I or preferred embodiments as described above in the form of blends or mixtures optionally together with one or more further electron transport materials and/or hole blocking materials and/or binders and/or other additives as described above and below, and one or more solvents.

The formulation may include or comprise, essentially consist of or consist of the said necessary or optional constituents as described above or below. All compounds or components which can be used in the formulations are either known or commercially available, or can be synthesised by known processes.

The formulation as described before may be prepared by a process which comprises:

(i) first mixing a compound of formula I, optionally a binder or a precursor of a binder as described before, optionally a further electron transport material, optionally one or more further additives as described above and below and a solvent or solvent mixture as described above and below and (ii) applying such mixture to a substrate; and optionally evaporating the solvent(s) to form an electron selective layer according to the present invention.

In step (i) the solvent may be a single solvent for the compound of formula I and the organic binder and/or further electron transport material may each be dissolved in a separate solvent followed by mixing the resultant solutions to mix the compounds.

Alternatively, the binder may be formed in situ by mixing or dissolving a compound of formula I in a precursor of a binder, for example a liquid monomer, oligomer or cross-linkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer. If a preformed binder is used it may be dissolved together with the compound formula I in a suitable solvent as described before, and the solution deposited for example by dipping, spraying, painting or printing it on a substrate to form a liquid layer and then removing the solvent to leave a solid layer. It will be appreciated that solvents are chosen which are able to dissolve all ingredients of the formulation, and which upon evaporation from the solution blend give a coherent defect free layer.

Besides the said components, the formulation as described before may comprise further additives and processing assistants. These include, inter alia, surface-active substances (surfactants), lubricants and greases, additives which modify the viscosity, additives which increase the conductivity, dispersants, hydrophobicising agents, adhesion promoters, flow improvers, antifoams, deaerating agents, diluents, which may be reactive or unreactive, fillers, assistants, processing assistants, dyes, pigments, stabilisers, sensitisers, nanoparticles and inhibitors.

Additives can be used to enhance the properties of the electron selective layer and/or the properties of any of the neighbouring layers and/or the performance of the optoelectronic device according to the invention. Additives can also be used to facilitate the deposition, the processing or the formation of the electron selective layer and/or the deposition, the processing or the formation of any of the neighbouring layers. Preferably, one or more additives are used which enhance the electrical conductivity of the electron selective layer and/or passivate the surface of any of the neighbouring layers.

Suitable methods to incorporate one or more additives include, for example exposure to a vapor of the additive at atmospheric pressure or at reduced pressure, mixing a solution or solid containing one or more additives and a material or a formulation as described or preferably described before, bringing one or more additives into contact with a material or a formulation as described before, by thermal diffusion of one or more additives into a material or a formulation as described before, or by ion-implantantion of one or more additives into a material or a formulation as described before.

Additives used for this purpose can be organic, inorganic, metallic or hybrid materials. Additives can be molecular compounds, for example organic molecules, salts, ionic liquids, coordination complexes or organometallic compounds, polymers or mixtures thereof. Additives can also be particles, for example hybrid or inorganic particles, preferably nanoparticles, or carbon based materials such as fullerenes, carbon nanotubes or graphene flakes.

Examples for additives that can enhance the electrical conductivity are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid)), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$), cations (e.g. $H^+$, $Li^+$, $Na^+$, $K^+$, $Rb^+$, $Cs^+$, $Co^{3+}$ and $Fe^{3+}$), $O_2$, redox active salts (e.g. $XeOF_4$, $(NO_2^+)(SbF_6^-)$, $(NO_2^+)(SbCl_6^-)$, $(NO_2^+)(BF_4^-)$, $NOBF_4$, $NOPF_6$, $AgClO_4$, $H_2IrCl_6$ and $La(NO_3)_3 \cdot 6H_2O$), strongly electron-accepting organic molecules (e.g. 2,3,5,6-tetrafluoro-7,7,8,8-tetracyanoquinodimethane (F4-TCNQ)), transition metal oxides (e.g. $WO_3$, $Re_2O_7$ and $MoO_3$), metal-organic complexes of cobalt, iron, bismuth and molybdenum, (p-$BrC_6H_4)_3NSbCl_6$, bismuth (III) tris(trifluoroacetate), $FSO_2OOSO_2F$, acetylcholine, $R_4N^+$, (R is an alkyl group), $R_4P^+$ (R is a straight-chain or branched alkyl group 1 to 20), $R_6As^+$ (R is an alkyl group), $R_3S^+$ (R is an alkyl group) and ionic liquids (e.g. 1-Ethyl-3-methylimidazolium bis(trifluoromethylsulfonyl)imide). Suitable cobalt complexes beside of tris(2-(1H-pyrazol-1-yl)-4-tert-butylpyridine)-cobalt(III) tris(bis(trifluoromethylsulfonyl)imide)) are cobalt complex salts as described in WO 2012/114315, WO 2012/114316, WO 2014/082706, WO 2014/082704, EP 2883881 or JP 2013-131477.

Suitable lithium salts are beside of lithium bis(trifluoromethylsulfonyl)imide, lithium tris(pentafluoroethyl)trifluorophosphate, lithium dicyanamide, lithium methylsulfate, lithium trifluormethanesulfonate, lithium tetracyanoborate, lithium dicyanamide, lithium tricyanomethide, lithium thiocyanate, lithium chloride, lithium bromide, lithium iodide, lithium hexafluoroposphate, lithium tetrafluoroborate, lithium perchlorate, lithium hexafluoroantimonate, lithium hexafluoroarsenate or a combination of two or more. A preferred lithium salt is lithium bis(trifluoromethylsulfonyl) imide.

Preferably, the formulation comprises from 0.1 mM to 50 mM, preferably from 5 to 20 mM of the lithium salt.

Suitable device structures for PSCs comprising a compound formula I and a mixed halide perovskite are described in WO 2013/171517, claims 52 to 71 and claims 72 to 79, which is entirely incorporated herein by reference.

Suitable device structures for PSCs comprising a compound formula and a dielectric scaffold together with a perovskite are described in WO 2013/171518, claims 1 to 90 or WO 2013/171520, claims 1 to 94 which are entirely incorporated herein by reference.

Suitable device structures for PSCs comprising a compound of formula I, a semiconductor and a perovskite are described in WO 2014/020499, claims 1 and 3 to 14, which is entirely incorporated herein by reference The surface-increasing scaffold structure described therein comprises nanoparticles which are applied and/or fixed on a support layer, e.g. porous $TiO_2$.

Suitable device structures for PSCs comprising a compounds of formula and comprising a planar heterojunction are described in WO 2014/045021, claims 1 to 39, which is entirely incorporated herein by reference. Such a device is characterized in having a thin film of a light-absorbing or light-emitting perovskite disposed between n-type (electron conducting) and p-type (hole-conducting) layers. Preferably, the thin film is a compact thin film.

The invention further relates to a method of preparing a PSC as described above or below, the method comprising the steps of:
  providing a first and a second electrode;
  providing an electron selective layer comprising a compound of formula I.

The invention relates furthermore to a tandem device comprising at least one device according to the invention as described above and below. Preferably, the tandem device is a tandem solar cell.

The tandem device or tandem solar cell according to the invention may have two semi-cells wherein one of the semi cells comprises the compounds, oligomers or polymers in the active layer as described or preferably described above. There exists no restriction for the choice of the other type of semi cell which may be any other type of device or solar cell known in the art.

There are two different types of tandem solar cells known in the art. The so called 2-terminal or monolithic tandem solar cells have only two connections. The two subcells (or synonymously semi cells) are connected in series. Therefore, the current generated in both subcells is identical (current matching). The gain in power conversion efficiency is due to an increase in voltage as the voltages of the two subcells add up. The other type of tandem solar cells is the so called 4-terminal or stacked tandem solar cell. In this case, both subcells are operated independently. Therefore, both subcells can be operated at different voltages and can also generate different currents. The power conversion efficiency of the tandem solar cell is the sum of the power conversion efficiencies of the two subcells.

The invention furthermore relates to a module comprising a device according to the invention as described before or preferably described before.

The compounds and compositions of the present invention can also be used as dye or pigment in other applications, for example as an ink dye, laser dye, fluorescent marker, solvent dye, food dye, contrast dye or pigment in coloring paints, inks, plastics, fabrics, cosmetics, food and other materials.

The compounds and compositions of the present invention are also suitable for use in the semiconducting channel of an OFET. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound and compositions according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these OFETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
  a source electrode,
  a drain electrode,
  a gate electrode,
  a semiconducting layer,
  one or more gate insulator layers,
  optionally a substrate.
wherein the semiconductor layer preferably comprises a compound of formula I.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the compounds and compositions (hereinafter referred to as "materials") according to the present invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The materials according to the present invention may be employed in one or more of the charge transport layers and/or in the emission layer, corresponding to their electrical and/or optical properties. Furthermore their use within the emission layer is especially advantageous, if the materials according to the present invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the materials according to the present invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of the materials according to the present invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and ClSO$_3$H), transition metal compounds (e.g., FeCl$_3$, FeOCl, Fe(ClO$_4$)$_3$, Fe(4-CH$_3$C$_6$H$_4$SO$_3$)$_3$, TiCl$_4$, ZrCl$_4$, HfCl$_4$, NbF$_5$, NbCl$_5$, TaCl$_5$, MoF$_5$, MoCl$_5$, WF$_5$, WCl$_6$, UF$_6$ and LnCl$_3$ (wherein Ln is a lanthanoid), anions (e.g., Cl$^-$, Br$^-$, I$^-$, I$_3^-$, HSO$_4^-$, SO$_4^{2-}$, NO$_3^-$, ClO$_4^-$, BF$_4^-$, PF$_6^-$, AsF$_6^-$, SbF$_6^-$, FeCl$_4^-$, Fe(CN)$_6^{3-}$, and anions of various sulfonic acids, such as aryl-SO$_3^-$). When holes are used as carriers, examples of dopants are cations (e.g., H$^+$, Li$^+$, Na$^+$, K$^+$, Rb$^+$ and Cs$^+$), alkali metals (e.g., Li, Na, K, Rb, and Cs), alkaline-earth metals (e.g., Ca, Sr, and Ba), O$_2$, XeOF$_4$, (NO$_2^+$) (SbF$_6^-$), (NO$_2^+$) (SbCl$_6^-$), (NO$_2^+$) (BF$_4^-$), AgClO$_4$, H$_2$IrCl$_6$, La(NO$_3$)$_3$.6H$_2$O, FSO$_2$OOSO$_2$F, Eu, acetylcholine, R$_4$N$^+$, (R is an alkyl group), R$_4$P$^+$ (R is an alkyl group), R$_6$As$^+$ (R is an alkyl group), and R$_3$S$^+$ (R is an alkyl group).

The conducting form of the materials according to the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The materials according to the present invention may also be suitable for use in organic plasmon-emitting diodes (OPEDs), as described for example in Koller et al., *Nat. Photonics*, 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material.

The materials according to the present invention having mesogenic or liquid crystalline properties can form oriented anisotropic films as described above, which are especially useful as alignment layers to induce or enhance alignment in a liquid crystal medium provided onto said anisotropic film.

According to another use, the materials according to the present invention are suitable for use in liquid crystal (LC) windows, also known as smart windows.

The materials according to the present invention may also be combined with photoisomerisable compounds and/or chromophores for use in or as photoalignment layers, as described in US 2003/0021913 A1.

According to another use, the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius.

The invention will now be described in more detail by reference to the following examples, which are illustrative only and do not limit the scope of the invention.

Example 1

Compound 1 was prepared as follows.

2,7-Diodo-4,4,9,9-tetrahexadecyl-4,9-dihydro-s-indaceno[1,2-b:5,6-b']dithiophene (1,1)

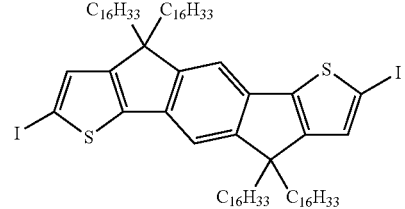

(1.1)

Iodine (2.094 g; 8.25 mmol) and (diacetoxyiodo)benzene (2.958 g; 9.00 mmol) were added successively to a stirred solution of 4,4,9,9-tetrahexadecyl-4,9-dihydro-s-indaceno [1,2-b:5,6-b']dithiophene (8.731 g; 7.50 mmol) in chloroform, dry (300 cm$^3$) at 40° C., and the mixture was stirred at this temperature for 4 h. The solvent was removed by rota evaporation in vacuo and the residue was triturated with acetone. An orange solid precipitate was collected by suction filtration and washed with acetone, methanol and acetone. The crude product was then dissolved in cyclohexane and the solution was filtered through a silica plug (10 g). The plug was eluted with cyclohexane. The filtrated was concentrated to nearly dryness then crashed with acetone. The solid was collected by suction filtration, washed with acetone, air-dried to yield the product as a cream colour powder (9.69 g, 93%). $^1$H NMR (400 MHz, Chloroform-d) δ 7.11 (s, 1H), 7.05 (s, 1H), 1.91-1.79 (m, 2H), 1.73 (td, J=13.0, 12.6, 4.7 Hz, 2H), 1.27-0.95 (m, 52H), 0.81 (t, J=6.8 Hz, 6H), 0.77-0.61 (m, 4H). $^{13}$C NMR (101 MHz, CDCl$_3$) δ 155.83, 152.54, 146.71, 135.44, 131.20, 113.32, 73.33, 54.24, 38.97, 31.94, 29.92, 29.71, 29.67, 29.63, 29.58, 29.37, 29.30, 24.09, 22.70, 14.13.

2,7-Dicyanomethylene-4,4,9,9-tetrahexadecyl-4,9-dihydro-s-indaceno[1,2-b:5,6-b']dithiophenequinone (1)

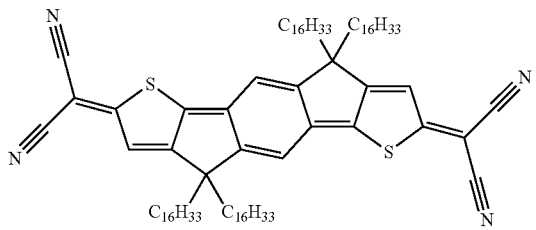

To a solution of malononitrile (0.661 g; 10.0 mmol) in N,N-dimethylformamide anhydrous (40 cm$^3$) was added sodium hydride 60% dispersion (0.400 g; 10.0 mmol) solid in fractions. The mixture was degassed and stirred at 20° C. for 20 minutes. 2,7-Diiodo-4,4,9,9-tetrahexadecyl-4,9-dihydro-s-indaceno[1,2-b:5,6-b]dithiophene (1.416 g; 1.00 mmol) and tetrakis(triphenylphosphino)palladium (116 mg; 0.100 mmol) were added under nitrogen. The mixture was further degassed for an additional 10 minutes then stirred at 110° C. for 20 hours to yield a dark-red clear solution. The solution was cooled to 20° C. 10% HCl (50 cm$^3$) was added slowly. The brownish yellow precipitate was collected by suction filtration. The solid was dissolved in dichloromethane (50 cm$^3$). 2,3-Dichloro-5,6-dicyano-1,4-benzoquinone (0.681 g; 3.0 mmol) was added and the mixture was stirred at reflux for 30 minutes to afford a dark blue solution. The mixture was rota evaporated to dryness. The brown residue was triturated with methanol and the brown solid was collected by suction filtration then was chromatographed on silica eluted with a mixture of 30% dichloromethane in petroleum ether 40-60° C. The pure was isolated as a purple-brown solid (0.188 g, 14.5%). $^1$H NMR (400 MHz, Chloroform-d) δ 6.88 (s, 1H), 6.80 (s, 1H), 1.83 (dddd, J=25.2, 17.9, 12.5, 4.9 Hz, 4H), 1.27-1.02 (m, 52H), 0.81 (t, J=6.7 Hz, 8H). $^{13}$C NMR (101 MHz, CDCl$_3$) δ 174.93, 172.35, 160.58, 149.37, 140.11, 119.30, 114.01, 113.73, 113.48, 69.09, 53.29, 39.20, 31.93, 29.72, 29.67, 29.60, 29.37, 29.32, 24.45, 22.70, 14.13.

Example 2

Compound 2 was prepared as follows.

2,8-Diiodo-6,6,12,12-tetra(4-hexadecyl-1-phenyl)-6,12-dihydro-dithieno[2,3-d:2',3'-d]-s-indaceno[1,2-b:5,6-b]dithiophene (2.1)

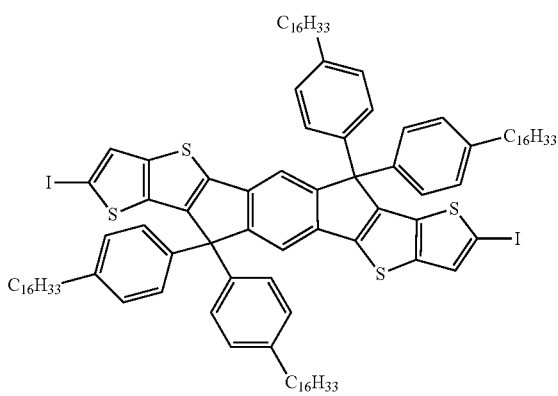

Iodine (0.335 g; 1.32 mmol) and diacetoxyiodo)benzene (0.473 g; 1.44 mmol) were added successively to a stirred solution of 6,6,12,12-tetra(4-hexadecyl-1-phenyl)-6,12-dihydro-dithieno[2,3-d:2',3'-d']-s-indaceno[1,2-b:5,6-b']dithiophene (1.897 g; 1.20 mmol) in anhydrous chloroform (50 cm$^3$) at 60° C. The mixture was stirred at this temperature for 2 hours. The red-brown solution was cooled to 20° C. Saturated sodium sulphite solution 5 cm$^3$ was added and the bilayer mixture was vigorously stirred for 30 minutes till the iodine colour was quenched. The solvent was removed by rota evaporation in vacuo and the residue was triturated with water. A pale-red solid was suction filtered off and washed with water, methanol and acetone. The solid was dissolved in hot cyclohexane then filtered through a silica plugged. The eluent was concentrated to yield the pure product as a bright yellow solid (2.05 g, 93%). $^1$H NMR (400 MHz, Chloroform-d) δ 7.38 (s, 1H), 7.32 (s, 1H), 7.07-6.96 (m, 8H), 2.48 (t, J=7.8 Hz, 4H), 1.51 (q, J=7.4 Hz, 4H), 1.18 (s, 52H), 0.80 (t, J=6.6 Hz, 6H).

2,8-Dicyanomethylene-6,6,12,12-tetra(4-hexadecyl-1-phenyl)-6,12-dihydro-dithieno[2,3-d:2',3'-d]-s-indaceno[1,2-b:5,6-b]dithiophenequinone (2)

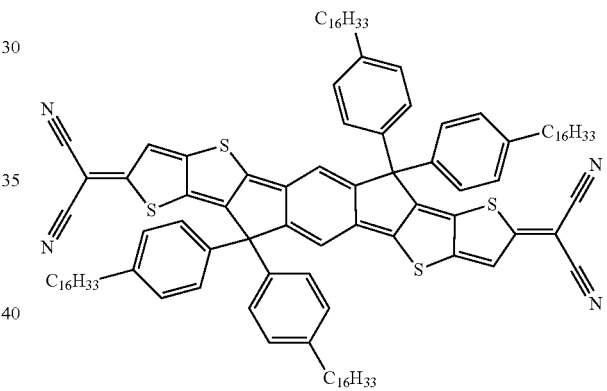

To a solution of malononitrile (0.495 g; 7.50 mmol) in N,N-dimethylformamide anhydrous (40 cm$^3$) was added sodium hydride 60% dispersion (0.30 g; 7.50 mmol) solid in small fractions. The mixture was degassed and stirred at 20° C. for 20 minutes. 2,8-Diiodo-6,6,12,12-tetra(4-hexadecyl-1-phenyl)-6,12-dihydro-dithieno[2,3-d:2',3'-d']-s-indaceno[1,2-b:5,6-b']dithiophene (1.374 g; 0.75 mmol) and tetrakis(triphosphino)palladium (87 mg; 0.075 mmol) were added under nitrogen. The yellow suspension was further degassed for an additional 10 minutes then stirred at 110° C. for 16 hours. The temperature was increased to 150° C. (external) and the mixture was stirred for 3 hours. The solution was cooled to 20° C. and 10% HCl (50 cm$^3$) was added slowly. The orange precipitate was collected by suction filtration, washed with water and methanol. The solid was dissolved in dichloromethane (50 cm$^3$) and 2,3-Dichloro-5,6-dicyano-1,4-benzoquinone (0.511 g; 2.25 mmol) was added under stirring. The purple mixture was stirred at 20° C. for 1 hour the rota evaporated to dryness. The brown residue was triturated with methanol and a red-brown solid was collected by suction filtration. The solid was chromatographed on silica eluted with 1:1 chloroform-petroleum ether 40-60° C. The product was isolated as a dark-green powder (0.50 g, 39%). $^1$H NMR (400 MHz, Chloroform-d) δ 7.12-7.07 (m, 4H), 7.06-7.17 (br, 2H) 7.03-6.97 (m, 4H), 2.52 (dd, J=9.1, 6.7 Hz, 4H), 1.53 (t, J=7.6 Hz, 4H), 1.18 (s, 52H), 0.86-0.73 (m, 6H). MS (APPI, m/z): found 1706.1; calc for C114H152N4S4 1706.

The invention claimed is:

1. A compound of formula I

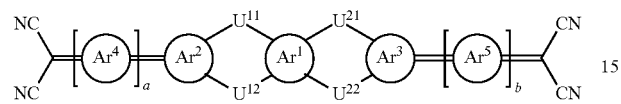

I wherein the individual radicals, independently of each other and on each occurrence identically or differently, have the following meanings one of $U^{11}$ and $U^{12}$ is a C=C double bond and the other is $CR^1R^2$, one of $U^{21}$ and $U^{22}$ is a C=C double bond and the other is $CR^3R^4$, $Ar^{1-5}$, $Ar^4$, $Ar^5$ a quinoidal alicyclic or heterocyclic group that has 5 to 30 ring atoms, is mono- or polycyclic, optionally contains fused rings, and is unsubstituted or substituted by one or more identical or different groups $R^1$ or L, $Ar^2$ and $Ar^3$ are selected from the following formulae and their mirror images:

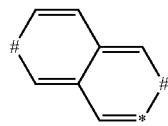

(1C)

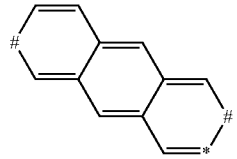

(2C)

(3C)

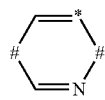

(4C)

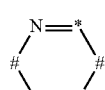

(5C)

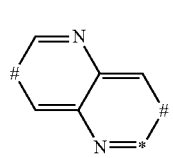

(6C)

-continued

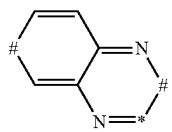

(7C)

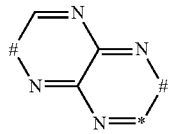

(8C)

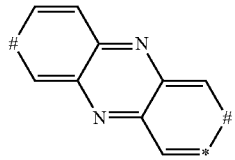

(9C)

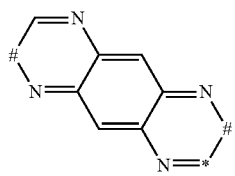

(10C)

(11C)

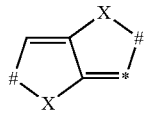

(12C)

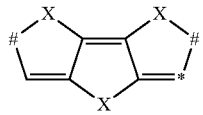

(13C)

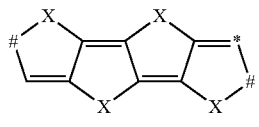

(14C)

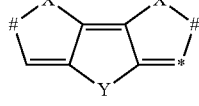

(15C)

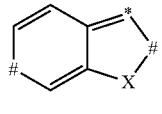

(16C)

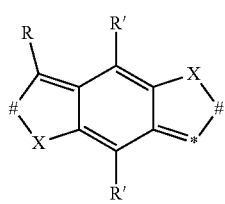

(17C)

-continued
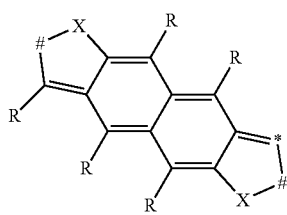
(18C)
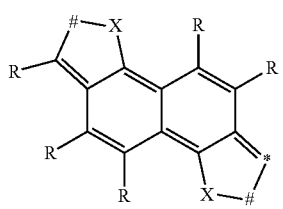
(19C)
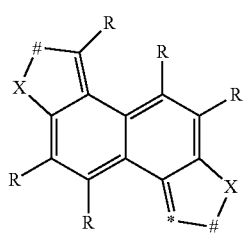
(20C)
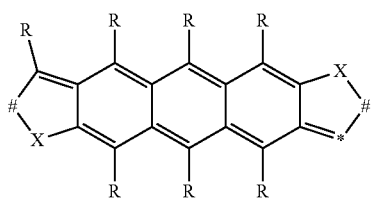
(21C)
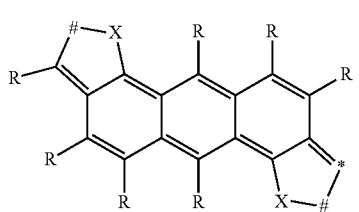
(22C)
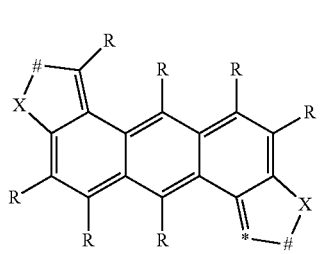
(23C)
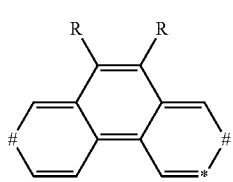
(24C)
-continued
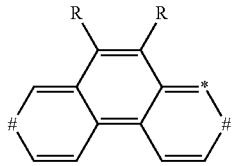
(25C)
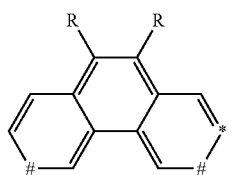
(26C)
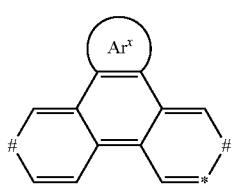
(27C)
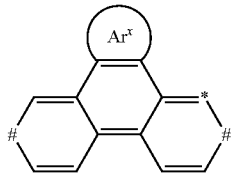
(28C)
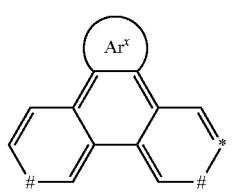
(29C)
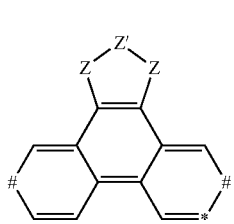
(30C)
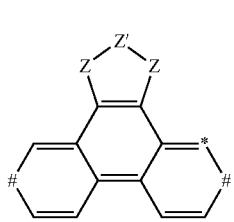
(31C)
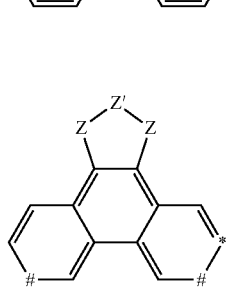
(32C)

-continued (33C)
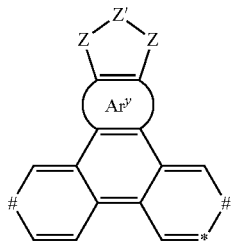

(34C)
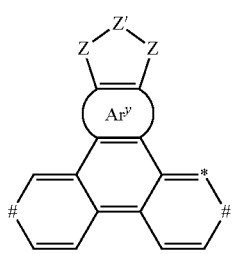

(35C)
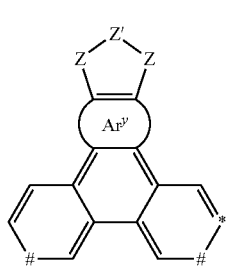

X O, S, Se or Te,
R, R' One of the meanings of $R^1$ of L as defined for formula I,
an $sp^2$ carbon that is linked to the adjacent group in formula I via a C=C double bond, and
* an $sp^2$ carbon atom that is linked to the adjacent group in formula I via a C—C single bond,
Z, Z' O, S, C(=O), NR, =N— or =CR—, wherein at least one of Z and Z' is different from =N— and =CR—,
$Ar^x$, $Ar^y$ a fused 5- or 6-membered aromatic ring wherein one or more CH groups are optionally replaced by —O—, —S—, Se, Te, =N—, —NR— or —C(=O)—, and one or more H atoms are optionally replaced by $R^1$ or L,
Y $CR^1R^2$, $SiR^1R^2$, $GeR^1R^2$, NR, C(=O) or S(=O),
$R^{1-4}$ H, F, Cl, CN, straight-chain, branched or cyclic alkyl with 1 to 40 C atoms in which one or more $CH_2$ groups are optionally replaced by —O—, —S—, —C(=O)—, —C(=S)—, —C(=O)—O—, —O—C(=O)—, —$NR^o$—, —$SiR^oR^{oo}$—, —$CF_2$—, —$CR^o$=$CR^{oo}$—, —$CY^1$=$CY^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group,
or straight-chain, branched or cyclic silyl with 1 to 40 Si atoms,
or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, L F, Cl, —$NO_2$, —CN, —NC, —NCO, —NCS, —OCN, —SCN, $R^o$, $OR^o$, $SR^o$, —C(=O)$X^o$, —C(=O)$R^o$, —C(=O)—$OR^o$, —O—C(=O)—$R^o$, —$NH_2$, —$NHR^o$, —$NR^oR^{oo}$, —C(=O)$NHR^o$, —C(=O)$NR^oR^{oo}$, —$SO_3R^o$, —$SO_2R^o$, —OH, —$NO_2$, —$CF_3$, —$SF_5$, or optionally substituted silyl with 1 to 20 Si atoms, or carbyl or hydrocarbyl with 1 to 30 C atoms that is optionally substituted and optionally comprises one or more hetero atoms, $R^o$, $R^{oo}$ H or straight-chain or branched alkyl with 1 to 40 C atoms that is optionally fluorinated, $X^o$ halogen, a, b 0 or an integer from 1 to 10.

2. The compound according to claim 1, which is selected from the following formulae IA
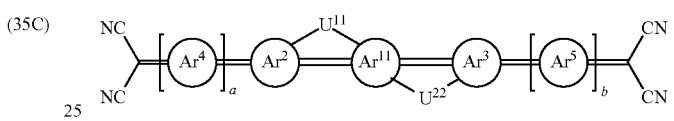

IB
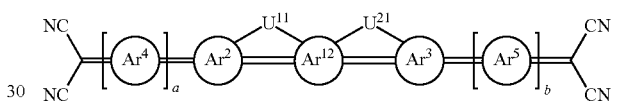

wherein $Ar^{1-5}$, $U^{11}$, $U^{21}$, $U^{22}$, a, b have the meanings for formula I, and $Ar^{11}$ and $Ar^{12}$ have one of the meanings given for $Ar^1$.

3. The compound according to claim 1, wherein $Ar^1$ in formula I is selected from the following formulae and their mirror images:

(1A)
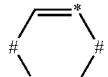

(2A)
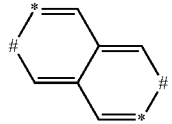

(3A)
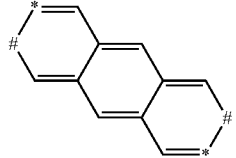

(4A)
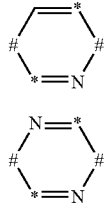

(5A)

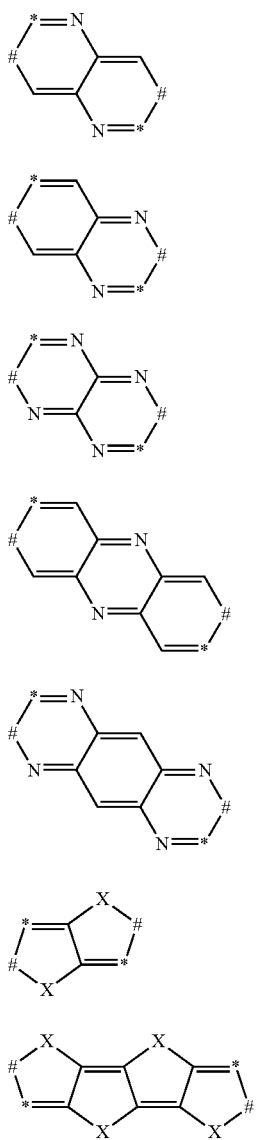
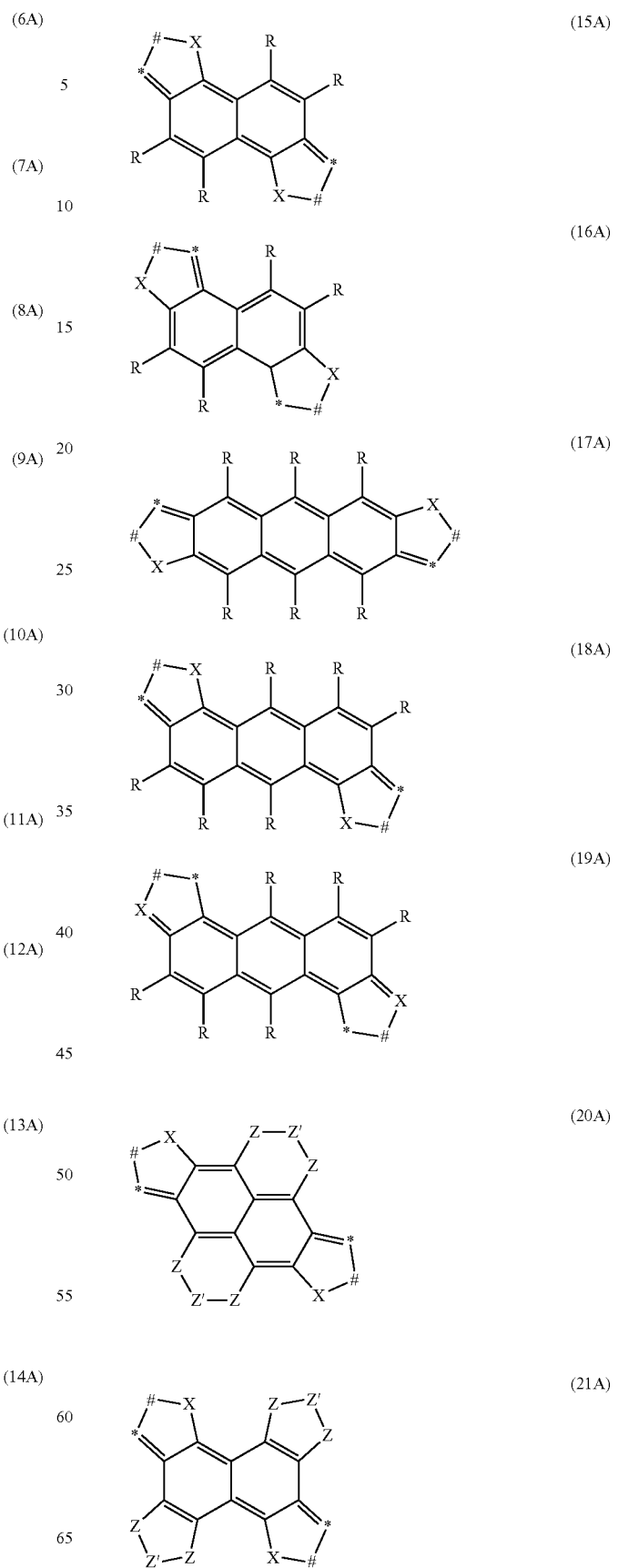

-continued

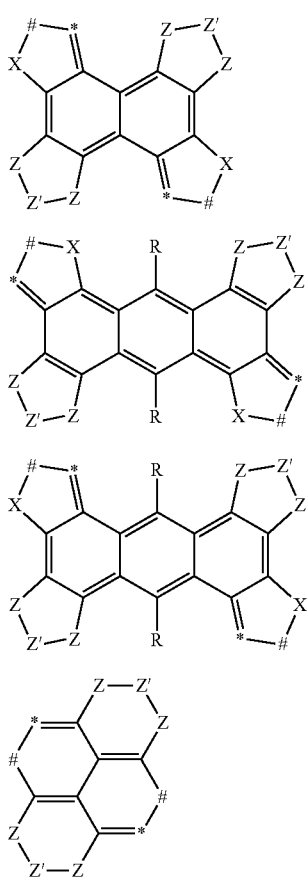

(22A)

(23A)

(24A)

(25A)

wherein the individual radicals, independently of each other and on each occurrence identically or differently, have the following meanings
X  O, S, Se or Te,
R, R' one of the meanings of $R^1$ or L as defined for formula I,
an $sp^2$ carbon atom that is linked to the adjacent group in formula I via a C=C double bond, and
* an $sp^2$ carbon atom that is linked to the adjacent group in formula I via a C—C single bond,
Z, Z' O, S, C(=O), NR, =N— or =CR—, wherein at least one of Z and Z' is different from =N— and =CR—.

4. The compound according to claim 1, wherein $Ar^1$ in formula I are selected from the following formulae and their mirror images:

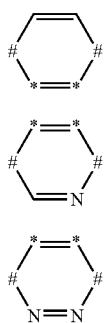

(1B)

(2B)

(3B)

-continued

(4B)

(5B)

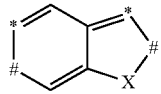

(6B)

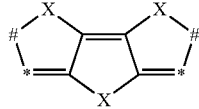

(7B)

(8B)

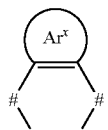

(9B)

(10B)

(11B)

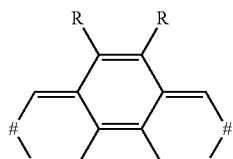

(12B)

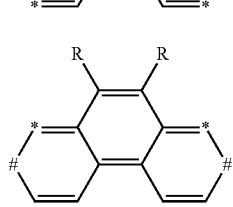

(13B)

-continued (14B)
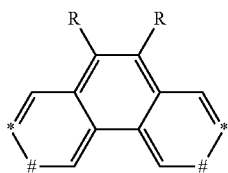

(15B)
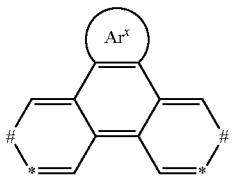

(16B)
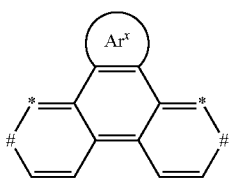

(17B)
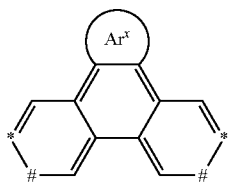

(18B)
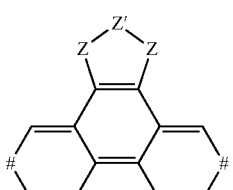

(19B)
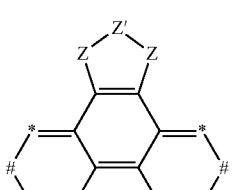

(20B)
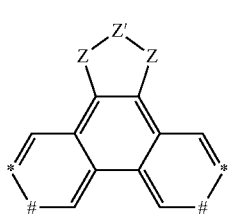

(21B)
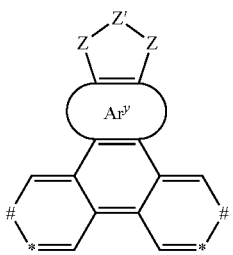

-continued (22B)
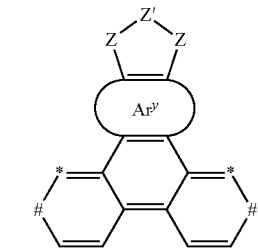

(23B)
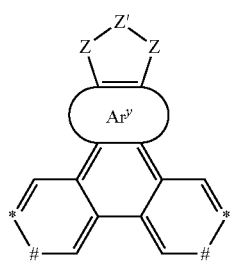

wherein the individual radicals, independently of each other and on each occurrence identically or differently, have the following meanings X O, S, Se or Te, R One of the meanings of $R^1$ of L as defined for formula I, \# an $sp^2$ carbon that is linked to the adjacent group in formula I via a C=C double bond, and \* an $sp^2$ carbon atom that is linked to the adjacent group in formula I via a C—C single bond, Z, Z' O, S, C(=O), NR, =N— or =CR—, wherein at least one of Z and Z' is different from =N— and =CR—, $Ar^x$, $Ar^y$ a fused 5- or 6-membered aromatic ring wherein one or more CH groups are optionally replaced by —O—, —S—, Se, Te, =N—, —NR— or —C(=O)—, and one or more H atoms are optionally replaced by $R^1$ or L, Y $CR^1R^2$, $SiR^1R^2$, $GeR^1R^2$, NR, C(=O) or S(=O), with L, $R^1$ and $R^2$ being as defined for formula I.

5. The compound according to claim 1, wherein $Ar^4$ and $Ar^5$ are selected from the following formulae and their mirror images:

(1D)
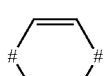

(2D)
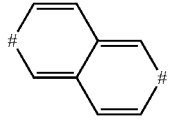

(3D)
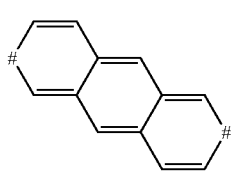

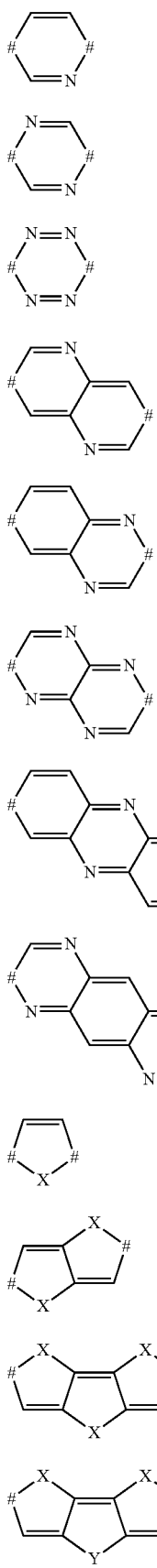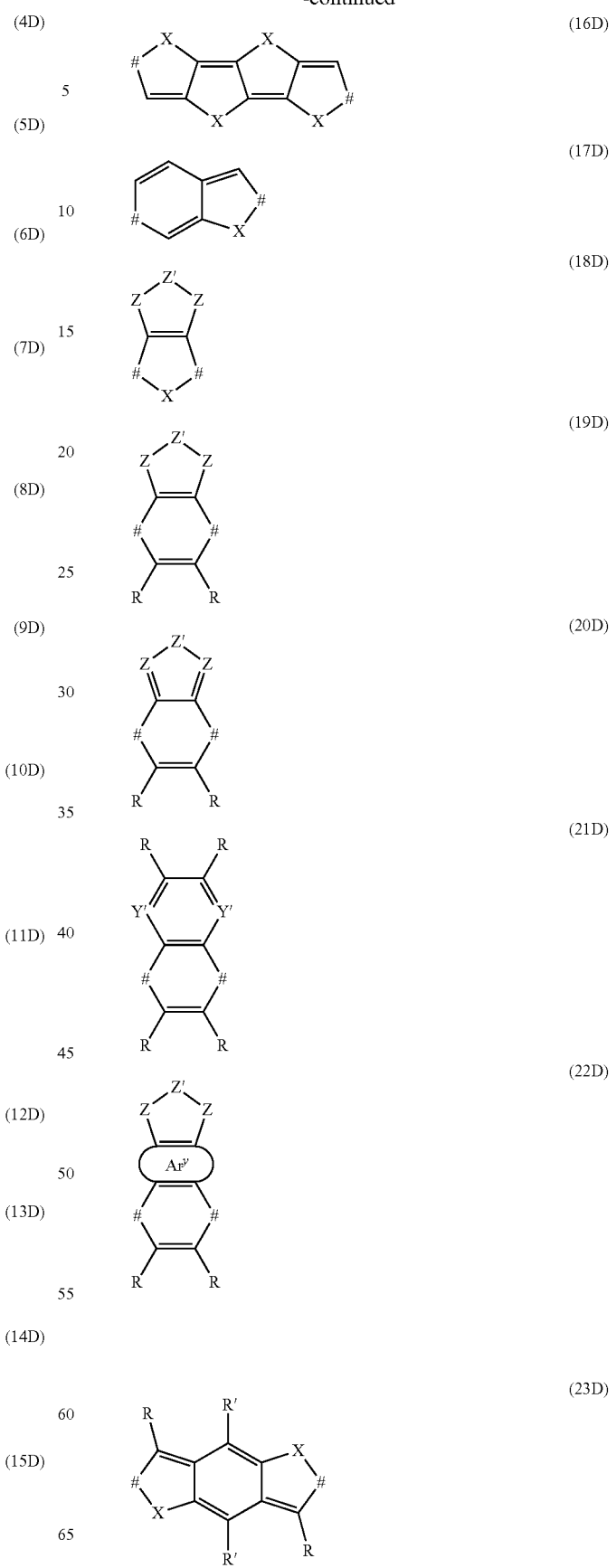

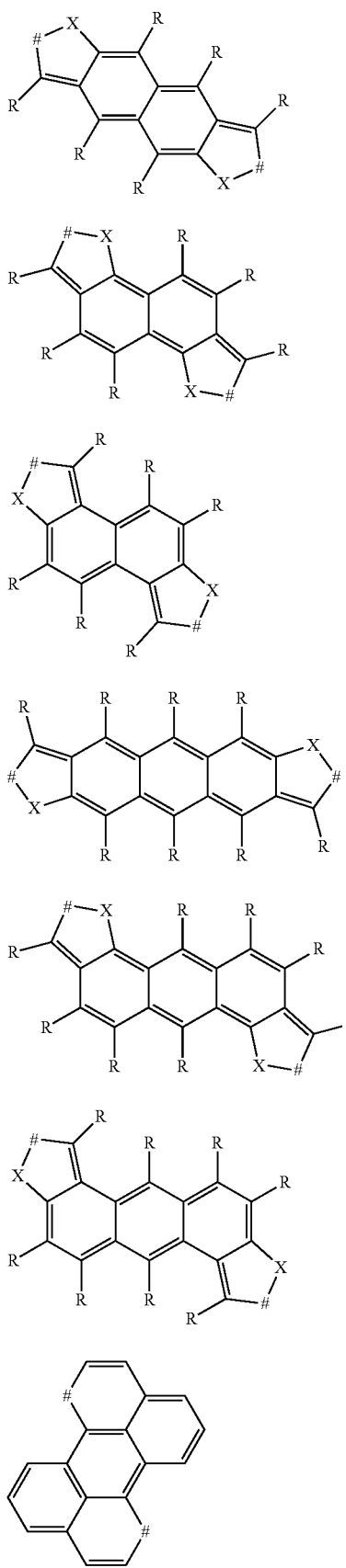
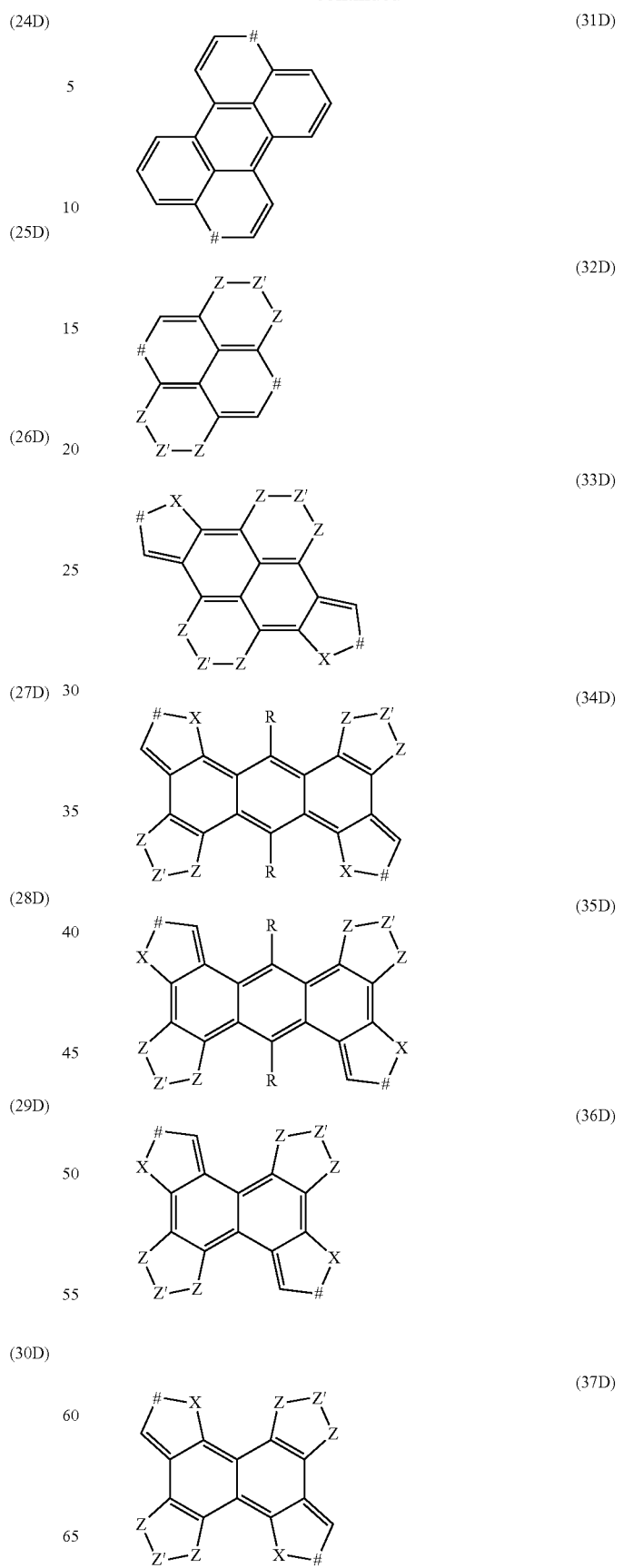

-continued

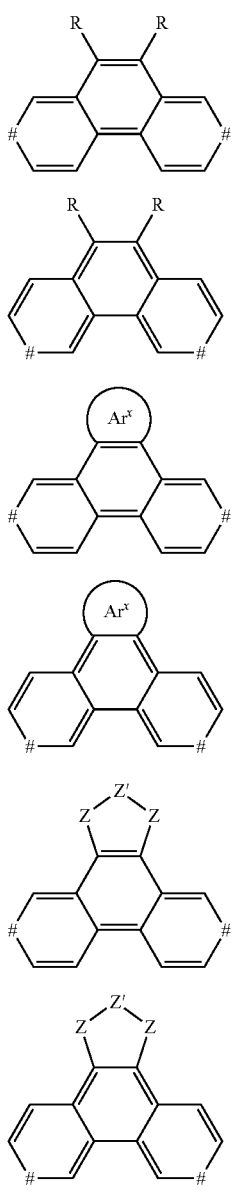

(38D)
(39D)
(40D)
(41D)
(42D)
(43D)

-continued (44D)
(45D)

Y' denotes N or CR

X O, S, Se or Te,

R, R' One of the meanings of $R^1$ of L as defined for formula I, an $sp^2$ carbon that is linked to the adjacent group in formula I via a C=C double bond, and

* an $sp^2$ carbon atom that is linked to the adjacent group in formula I via a C=C single bond, Z, Z' O, S, C(=O), NR, =N— or =CR—, wherein at least one of Z and Z' is different from =N— and =CR—, $Ar^x$, $Ar^y$ a fused 5- or 6-membered aromatic ring wherein one or more CH groups are optionally replaced by —O—, —S—, Se, Te, =N—, —NR— or —C(=O)—, and one or more H atoms are optionally replaced by $R^1$ or L, Y $CR^1R^2$, $SiR^1R^2$, $GeR^1R^2$, NR, C(=O) or S(=O), with L, $R^1$ and $R^2$ being as defined for formula I.

6. The compound according to claim 1, which is selected from the following formulae

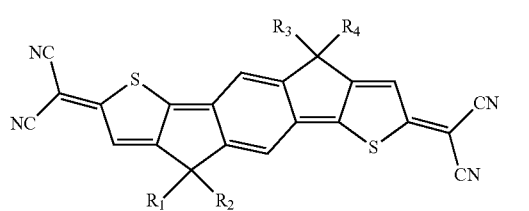

I1

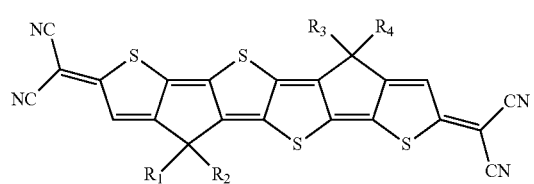

I2

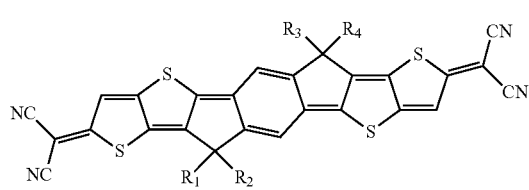

I3

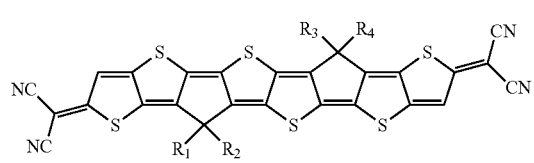

I4

-continued
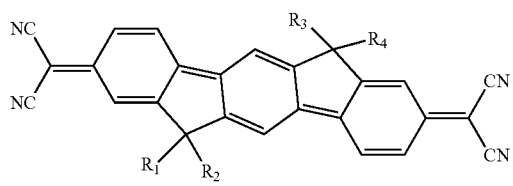
I5
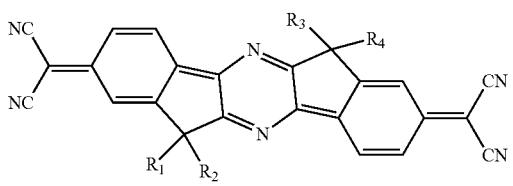
I6
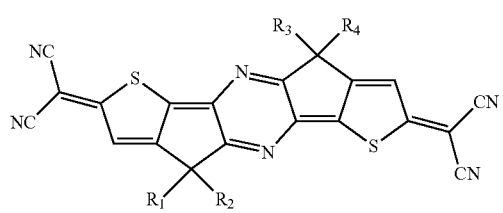
I7
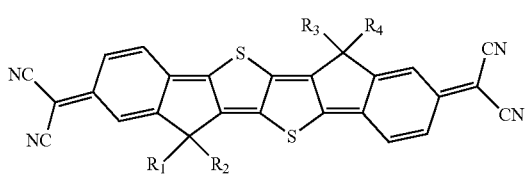
I8
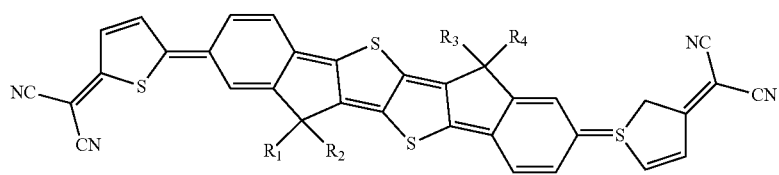
I9
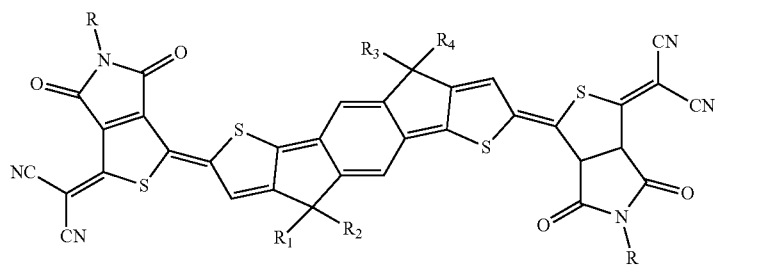
I10
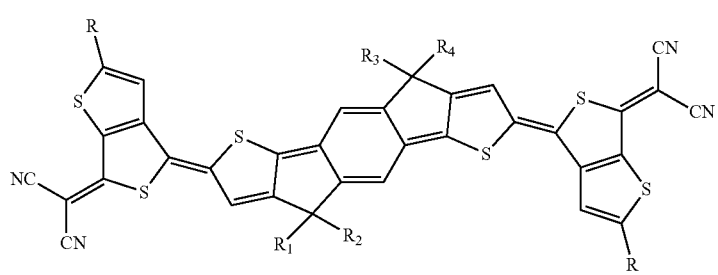
I11
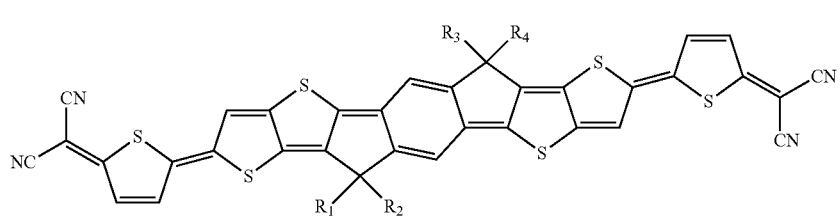
I12
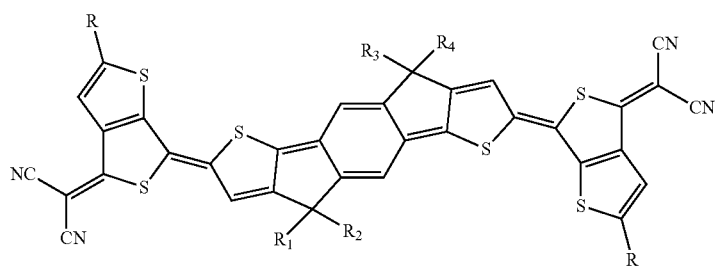
I13

I14
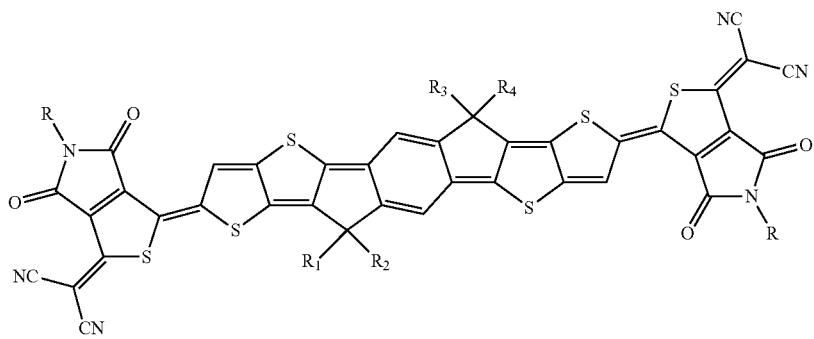
I15
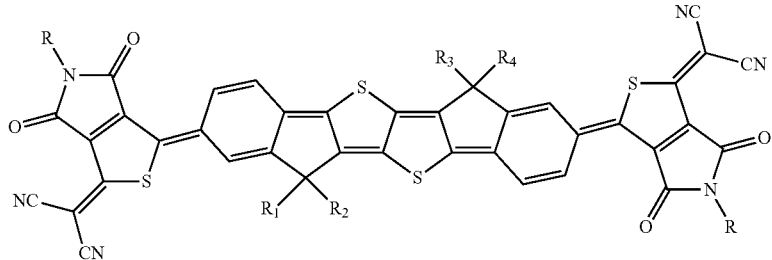
I16
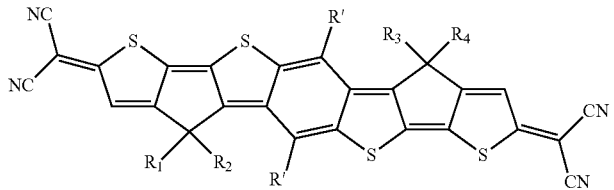
I17
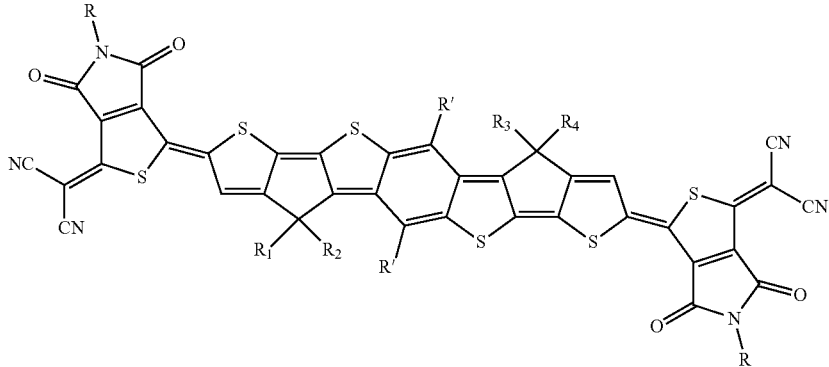
I18
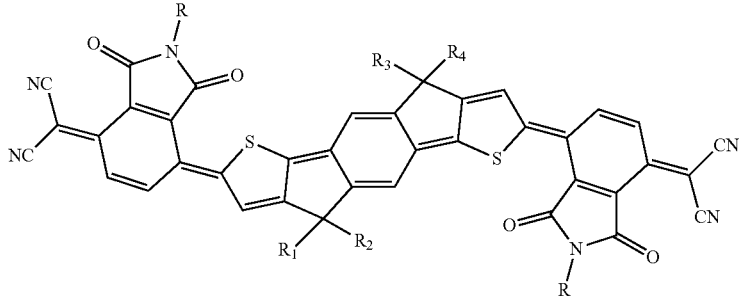

-continued

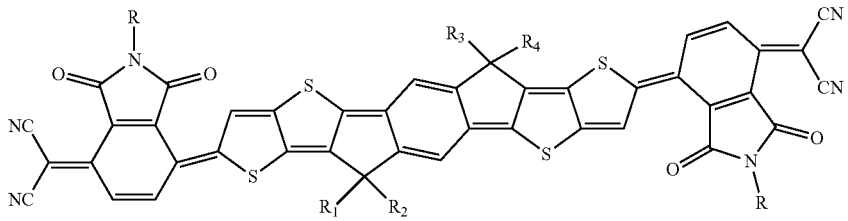

I19

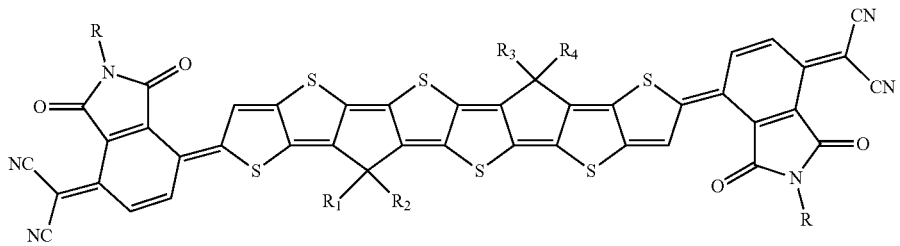

I20 wherein $R^{1-5}$, R and R' have the meanings given in claims 1 and 4, $R^{1-4}$ have the meanings given for formula I, and R, R' one of the meanings of $R^1$ or L as defined for formula I.

7. The compound according to claim 1, wherein $R^{1-4}$ are selected from alkyl or alkoxy with 1 to 40 C atoms which is optionally fluorinated, or aryl or heteroaryl having 4 to 30 ring atoms that is mono- or polycyclic, optionally contains fused rings, and is optionally substituted with one or more groups L as defined for formula I.

8. A composition comprising one or more compounds according to claim 1, and further comprising one or more compounds having one or more of a semiconducting, hole or electron transporting, hole or electron blocking, electrically conducting, photoconducting, photoactive or light emitting property, and/or a binder.

9. The composition of claim 8, comprising one or more n-type semiconductors, at least one of which is a compound of formula I, and further comprising one or more p-type semiconductors.

10. The composition of claim 8, comprising one or more p-type semiconductors selected from conjugated polymers.

11. A bulk heterojunction (BHJ) formed from a composition according to claim 8.

12. A formulation comprising one or more compounds according to claim 1, and one or more organic solvents.

13. An electronic or optoelectronic device, or a component thereof, or an assembly comprising it, which comprises a compound according to claim 1.

14. The electronic or optoelectronic device according to claim 13, which is selected from organic field effect transistors (OFET), organic thin film transistors (OTFT), organic light emitting diodes (OLED), organic light emitting transistors (OLET), organic light emitting electro-chemical cells (OLEC), organic photovoltaic devices (OPV), organic photodetectors (OPD), organic solar cells, dye-sensitized solar cells (DSSC), perovskite-based solar cells (PSC), organic photoelectrochemical cells (OPEC), laser diodes, Schottky diodes, photoconductors, photodetectors, thermoelectric devices and LC windows.

15. The component according to claim 13, which is selected from charge injection layers, charge transport layers, interlayers, planarising layers, antistatic films, polymer electrolyte membranes (PEM), conducting substrates and conducting patterns.

16. The assembly according to claim 13, which is selected from integrated circuits (IC), radio frequency identification (RFID) tags, security markings, security devices, flat panel displays, backlights of flat panel displays, electrophotographic devices, electrophotographic recording devices, organic memory devices, sensor devices, biosensors and biochips.

* * * * *